(12) United States Patent
Haury et al.

(10) Patent No.: US 11,491,318 B2
(45) Date of Patent: Nov. 8, 2022

(54) MULTIPLE FLUID DELIVERY SYSTEM WITH MULTI-USE DISPOSABLE SET AND FEATURES THEREOF

(71) Applicant: BAYER HEALTHCARE LLC, Whippany, NJ (US)

(72) Inventors: John Haury, Sewickly, PA (US); Michael Swantner, Saxonburg, PA (US); Richard Sokolov, Earlwood (AU); Benjamin James Cullen, Beecroft (AU); Alison Ruth Von Moger, Carnegie (AU); Ernesto Hueso Monis, Glen Huntly (AU); Kamman Law, Burwood (AU); Mark Silivio Profaca, West Pymble (AU); Patrick Spence, Gibsonia, PA (US); Michael Spohn, Fenelton, PA (US); Justin Angert, Gibsonia, PA (US); Brian Cain, Elizabeth, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 321 days.

(21) Appl. No.: 16/713,299

(22) Filed: Dec. 13, 2019

(65) Prior Publication Data

US 2020/0114138 A1 Apr. 16, 2020

Related U.S. Application Data

(62) Division of application No. 15/541,573, filed as application No. PCT/US2016/012434 on Jan. 7, 2016, now Pat. No. 10,507,319.

(Continued)

(51) Int. Cl.
*A61M 39/10* (2006.01)
*A61M 5/168* (2006.01)
(Continued)

(52) U.S. Cl.
CPC .......... *A61M 39/10* (2013.01); *A61M 5/1407* (2013.01); *A61M 5/1452* (2013.01);
(Continued)

(58) Field of Classification Search
CPC .............. A61M 5/1407; A61M 5/1408; A61M 5/1422; A61M 5/14216; A61M 5/14212;
(Continued)

(56) References Cited

U.S. PATENT DOCUMENTS

| | | | |
|---|---|---|---|
| 205,069 | A | 6/1878 | Farnsworth |
| 339,417 | A | 4/1886 | Horen |

(Continued)

FOREIGN PATENT DOCUMENTS

| | | | |
|---|---|---|---|
| CA | 1126117 | A | 6/1982 |
| CA | 2045070 | A1 | 2/1992 |

(Continued)

OTHER PUBLICATIONS

Asepti-Quik S Connector Catalog, May 2010.
(Continued)

*Primary Examiner* — Theodore J Stigell
(74) *Attorney, Agent, or Firm* — Joseph L. Kent; David Schramm; James R. Stevenson

(57) ABSTRACT

A multi-use disposable set (MUDS) has at least one syringe having a proximal end and a distal end spaced apart from the proximal end along a longitudinal axis. The MUDS further has a plunger reciprocally movable within a syringe interior between the proximal end and the distal end. A manifold is in fluid communication with the distal end of the at least one syringe. At least one valve is in fluid communication with the syringe interior. The at least one valve is operable between a filling position for filling the syringe interior with fluid and a delivery position for delivering the fluid from the syringe interior. At least one connection port is in fluid (Continued)

communication with the manifold and the syringe interior when the at least one valve is in the delivery position. A multi-fluid delivery system having the medical connector and MUDS is also provided. Various features of the MUDS system are also described.

6 Claims, 47 Drawing Sheets

Related U.S. Application Data

(60) Provisional application No. 62/242,090, filed on Oct. 15, 2015, provisional application No. 62/242,101, filed on Oct. 15, 2015, provisional application No. 62/101,752, filed on Jan. 9, 2015.

(51) Int. Cl.
*A61M 5/145* (2006.01)
*A61M 5/142* (2006.01)
*A61M 5/14* (2006.01)
*A61M 5/19* (2006.01)
*A61M 5/31* (2006.01)
*A61M 39/24* (2006.01)
*A61M 5/00* (2006.01)
*A61J 3/00* (2006.01)

(52) U.S. Cl.
CPC .... *A61M 5/14212* (2013.01); *A61M 5/16827* (2013.01); *A61M 5/16881* (2013.01); *A61M 5/19* (2013.01); *A61M 5/3146* (2013.01); *A61M 39/24* (2013.01); *A61J 3/002* (2013.01); *A61M 5/007* (2013.01); *A61M 2205/07* (2013.01); *A61M 2205/14* (2013.01); *A61M 2205/3306* (2013.01); *A61M 2205/502* (2013.01)

(58) Field of Classification Search
CPC .......... A61M 5/16827; A61M 5/16881; A61M 5/1452; A61M 39/24; A61M 39/10; A61M 5/19; A61M 5/3146; A61M 5/007; A61M 5/008; A61M 2205/07; A61M 2205/14; A61M 39/1011; A61M 2205/3306; A61M 2205/502; A61J 3/002
USPC ...................................... 417/477.2
See application file for complete search history.

(56) References Cited

U.S. PATENT DOCUMENTS

| | | |
|---|---|---|
| 372,093 A | 10/1887 | Struck |
| 373,292 A | 11/1887 | Jacobson et al. |
| 375,160 A | 12/1887 | Housel |
| 378,073 A | 2/1888 | Alexander |
| 388,876 A | 9/1888 | Humans |
| 503,778 A | 8/1893 | Trimble |
| 517,192 A | 3/1894 | Prior |
| 567,115 A | 9/1896 | Atkinson et al. |
| 660,040 A | 10/1900 | Baker |
| 711,128 A | 10/1902 | Schirmer |
| 726,069 A | 4/1903 | Josse |
| 783,317 A | 2/1905 | Salsman |
| 878,073 A | 2/1908 | Lancia |
| 921,691 A | 5/1909 | Friday |
| 926,755 A | 7/1909 | Locke |
| 1,085,963 A | 2/1914 | Bresnahan |
| 1,103,212 A | 7/1914 | Kraemer |
| 1,234,684 A | 7/1917 | Neibling |
| 1,324,654 A | 12/1919 | Ferguson |
| 1,346,127 A | 7/1920 | Janes |
| 1,383,997 A | 7/1921 | Pease |
| 1,452,318 A | 4/1923 | Spiker et al. |
| 1,511,962 A | 10/1924 | Hanson |
| 1,516,032 A | 11/1924 | White |
| 1,531,698 A | 3/1925 | Janes |
| 1,590,940 A | 6/1926 | Hallett |
| 1,595,688 A | 8/1926 | Porter |
| 1,614,389 A | 1/1927 | Rainer |
| 1,689,419 A | 10/1928 | Bronander |
| 1,703,389 A | 2/1929 | Coles |
| 1,708,112 A | 4/1929 | Wheary |
| 1,716,127 A | 6/1929 | Hamlin |
| 1,748,810 A | 2/1930 | Wandel |
| 1,805,741 A | 5/1931 | Prestage |
| 1,845,882 A | 2/1932 | Litschge |
| 1,850,273 A | 3/1932 | Thayer |
| 1,866,217 A | 7/1932 | Mayer |
| 1,873,304 A | 8/1932 | De Mooy |
| 1,973,351 A | 9/1934 | Meeker |
| 2,019,402 A | 10/1935 | Duffy |
| 2,028,161 A | 1/1936 | Mann |
| 2,038,155 A | 4/1936 | Aldridge |
| 2,062,285 A | 12/1936 | Bergman |
| 2,086,162 A | 7/1937 | Janicke |
| 2,102,121 A | 12/1937 | Janicke |
| 2,114,565 A | 4/1938 | Kovach |
| 2,160,687 A | 5/1939 | Stubbs |
| 2,169,807 A | 8/1939 | Lyon |
| 2,183,318 A | 12/1939 | Burton |
| 2,206,816 A | 7/1940 | Levitt |
| 2,258,055 A | 10/1941 | Holloway et al. |
| 2,287,746 A | 6/1942 | Morton |
| 2,306,364 A | 12/1942 | Skaredoff |
| 2,335,085 A | 11/1943 | Roberts |
| 2,409,650 A | 10/1946 | Wiggins |
| 2,412,597 A | 12/1946 | Brewer |
| 2,417,250 A | 3/1947 | Harvey |
| 2,435,361 A | 2/1948 | Mallory |
| 2,485,842 A | 10/1949 | Pennington |
| 2,486,185 A | 10/1949 | Mallory |
| 2,642,258 A | 6/1953 | Stone et al. |
| 2,648,290 A | 8/1953 | Ashton et al. |
| 2,702,008 A | 2/1955 | Stockard |
| 2,728,550 A | 12/1955 | Sinkler |
| 2,731,053 A | 1/1956 | Lockhart |
| 2,776,104 A | 1/1957 | Sinkler |
| 2,780,243 A | 2/1957 | Williams et al. |
| 2,783,713 A | 3/1957 | Klein et al. |
| 2,793,593 A | 5/1957 | Klein et al. |
| 2,798,487 A | 7/1957 | Ferguson |
| 2,821,926 A | 2/1958 | Miller et al. |
| 2,842,124 A | 7/1958 | James |
| 2,853,982 A | 9/1958 | Bachle et al. |
| 2,867,375 A | 1/1959 | Petersen |
| 2,876,985 A | 3/1959 | Birchall, Jr. et al. |
| 2,938,238 A | 5/1960 | Gewecke et al. |
| 2,946,606 A | 7/1960 | Smith |
| 2,985,192 A | 5/1961 | Taylor et al. |
| 2,997,043 A | 8/1961 | Flynn |
| 3,013,394 A | 12/1961 | Musser |
| 3,038,694 A | 6/1962 | Dunbeck et al. |
| 3,048,191 A | 8/1962 | Crang |
| 3,057,350 A | 10/1962 | Cowley |
| 3,075,473 A | 1/1963 | Finley |
| 3,083,895 A | 4/1963 | Welles, Jr. |
| 3,093,359 A | 6/1963 | De Woody |
| 3,142,474 A | 7/1964 | Nelson |
| 3,145,660 A | 8/1964 | Bush |
| 3,146,775 A | 9/1964 | Moore et al. |
| 3,157,201 A | 11/1964 | Littmann |
| 3,164,279 A | 1/1965 | Towns |
| 3,168,872 A | 2/1965 | Pinkerton |
| 3,181,895 A | 5/1965 | Cator |
| 3,185,179 A | 5/1965 | Harautuneian |
| 3,202,062 A | 8/1965 | Burden |
| 3,206,163 A | 9/1965 | Freed |
| 3,229,640 A | 1/1966 | Williams |
| 3,245,698 A | 4/1966 | Fromknecht |
| 3,249,052 A | 5/1966 | Karlak |
| 3,256,821 A | 6/1966 | Brederhoff |

(56) References Cited

U.S. PATENT DOCUMENTS

| | | | |
|---|---|---|---|
| 3,268,203 | A | 8/1966 | Gilmont et al. |
| 3,276,472 | A | 10/1966 | Jinkens et al. |
| 3,277,922 | A | 10/1966 | Eisel |
| 3,313,291 | A | 4/1967 | Marshall |
| 3,349,713 | A | 10/1967 | Fassbender |
| 3,394,954 | A | 7/1968 | Sarns |
| 3,395,925 | A | 8/1968 | Dreiding |
| 3,411,534 | A | 11/1968 | Rose |
| 3,434,691 | A | 3/1969 | Hamilton |
| 3,435,819 | A | 4/1969 | Reynolds et al. |
| 3,447,468 | A | 6/1969 | Kinne |
| 3,447,479 | A | 6/1969 | Rosenberg |
| 3,450,152 | A | 6/1969 | Ouellette |
| 3,464,359 | A | 9/1969 | King et al. |
| 3,471,079 | A | 10/1969 | Myers |
| 3,484,077 | A | 12/1969 | Porter |
| 3,485,265 | A | 12/1969 | Buono |
| 3,489,158 | A | 1/1970 | Mackay et al. |
| 3,523,523 | A | 8/1970 | Reich et al. |
| 3,548,827 | A | 12/1970 | Abel |
| 3,552,393 | A | 1/1971 | Willgerodt |
| 3,554,488 | A | 1/1971 | Alexander |
| 3,556,691 | A | 1/1971 | Buri |
| 3,569,903 | A | 3/1971 | Brishka |
| 3,582,040 | A | 6/1971 | Gutierrez |
| 3,586,049 | A | 6/1971 | Adamson |
| 3,586,129 | A | 6/1971 | Cass |
| 3,597,113 | A | 8/1971 | Dumoulin et al. |
| 3,614,060 | A | 10/1971 | Freed et al. |
| 3,623,474 | A | 11/1971 | Heilman et al. |
| 3,638,973 | A | 2/1972 | Poletti |
| 3,658,061 | A | 4/1972 | Hall |
| 3,678,960 | A | 7/1972 | Leibinsohn |
| 3,687,416 | A | 8/1972 | Mueller |
| 3,695,788 | A | 10/1972 | Loomans |
| 3,701,345 | A | 10/1972 | Heilman |
| 3,718,409 | A | 2/1973 | Brandenberg et al. |
| 3,731,679 | A | 5/1973 | Wilhelmson et al. |
| 3,739,943 | A | 6/1973 | Wilhelmson et al. |
| 3,755,655 | A | 8/1973 | Senegal |
| 3,768,476 | A | 10/1973 | Raitto |
| 3,793,600 | A | 2/1974 | Grosbard |
| 3,812,843 | A | 5/1974 | Wootten et al. |
| 3,828,775 | A | 8/1974 | Armel |
| 3,834,372 | A | 9/1974 | Turney |
| 3,835,862 | A | 9/1974 | Villari |
| 3,838,948 | A | 10/1974 | McCorvey |
| 3,855,129 | A | 12/1974 | Abrahams et al. |
| 3,865,134 | A | 2/1975 | Holcomb |
| 3,866,957 | A | 2/1975 | Norton |
| 3,882,899 | A | 5/1975 | Ginsberg et al. |
| 3,888,239 | A | 6/1975 | Rubinstein |
| 3,895,220 | A | 7/1975 | Nelson et al. |
| 3,898,983 | A | 8/1975 | Elam |
| 3,909,910 | A | 10/1975 | Rowe et al. |
| 3,916,931 | A | 11/1975 | Shaw et al. |
| 3,916,943 | A | 11/1975 | Hester et al. |
| 3,927,955 | A | 12/1975 | Spinosa et al. |
| 3,932,065 | A | 1/1976 | Ginsberg et al. |
| 3,935,971 | A | 2/1976 | Papoff et al. |
| 3,940,325 | A | 2/1976 | Hirao |
| 3,941,126 | A | 3/1976 | Dietrich et al. |
| 3,949,746 | A | 4/1976 | Wallach |
| 3,957,082 | A | 5/1976 | Fuson et al. |
| 3,958,103 | A | 5/1976 | Oka et al. |
| 3,958,898 | A | 5/1976 | Abrahams et al. |
| 3,968,195 | A | 7/1976 | Bishop |
| 3,974,810 | A | 8/1976 | Yajima |
| 3,976,311 | A | 8/1976 | Spendlove |
| 3,981,620 | A | 9/1976 | Abrahams et al. |
| 3,985,133 | A * | 10/1976 | Jenkins ............ A61M 5/172 604/152 |
| 3,986,508 | A | 10/1976 | Barrington |
| 3,987,930 | A | 10/1976 | Fuson |
| 3,990,727 | A | 11/1976 | Gallagher |
| 3,991,975 | A | 11/1976 | Sibrava |
| 3,993,061 | A | 11/1976 | O'Leary |
| 3,993,065 | A | 11/1976 | Szabo et al. |
| 3,994,294 | A | 11/1976 | Knute |
| 3,995,381 | A | 12/1976 | Manfred et al. |
| 3,997,195 | A | 12/1976 | Bartholomew |
| 4,001,549 | A | 1/1977 | Corwin |
| 4,008,003 | A | 2/1977 | Pinkerton |
| 4,010,611 | A | 3/1977 | Zachery |
| 4,014,467 | A | 3/1977 | Ferguson |
| 4,014,514 | A | 3/1977 | Priese et al. |
| 4,014,629 | A | 3/1977 | Elsworth |
| 4,019,512 | A | 4/1977 | Tenczar |
| 4,022,205 | A | 5/1977 | Tenczar |
| 4,026,581 | A | 5/1977 | Pasbrig |
| 4,030,494 | A | 6/1977 | Tenczar |
| 4,030,495 | A | 6/1977 | Virag |
| 4,032,263 | A | 6/1977 | Pareja |
| 4,038,981 | A | 8/1977 | LeFevre et al. |
| 4,044,757 | A | 8/1977 | McWhorter et al. |
| 4,044,758 | A | 8/1977 | Patel |
| 4,049,295 | A | 9/1977 | Piers |
| 4,061,142 | A | 12/1977 | Tuttle |
| 4,063,553 | A | 12/1977 | Karsh |
| 4,065,230 | A | 12/1977 | Gezari |
| 4,067,668 | A | 1/1978 | Nimell |
| 4,071,039 | A | 1/1978 | Goof |
| 4,072,056 | A | 2/1978 | Lee |
| 4,090,502 | A | 5/1978 | Tajika |
| 4,106,654 | A | 8/1978 | Jones |
| 4,121,622 | A | 10/1978 | Forberg |
| 4,123,091 | A | 10/1978 | Cosentino et al. |
| 4,127,360 | A | 11/1978 | Carpenter |
| 4,136,708 | A | 1/1979 | Cosentino et al. |
| 4,137,011 | A | 1/1979 | Rock |
| 4,147,184 | A | 4/1979 | Jess |
| 4,151,845 | A | 5/1979 | Clemens |
| 4,161,949 | A | 7/1979 | Thanawalla |
| 4,177,835 | A | 12/1979 | Paley |
| 4,178,240 | A | 12/1979 | Pinkerton |
| 4,181,223 | A | 1/1980 | Millet |
| 4,187,057 | A | 2/1980 | Xanthopoulos |
| 4,187,846 | A | 2/1980 | Lolachi et al. |
| 4,191,183 | A | 3/1980 | Mendelson |
| 4,194,509 | A | 3/1980 | Pickering et al. |
| 4,198,080 | A | 4/1980 | Carpenter |
| 4,199,000 | A | 4/1980 | Edstrom |
| 4,207,871 | A | 6/1980 | Jenkins |
| 4,207,923 | A | 6/1980 | Giurtino |
| 4,215,847 | A | 8/1980 | Hoos |
| 4,223,675 | A | 9/1980 | Williams |
| 4,225,290 | A | 9/1980 | Allington |
| 4,227,615 | A | 10/1980 | Flick |
| 4,230,151 | A | 10/1980 | Jonsson |
| 4,230,231 | A | 10/1980 | Burnett et al. |
| 4,233,156 | A | 11/1980 | Tsukada et al. |
| 4,236,880 | A | 12/1980 | Archibald |
| 4,245,963 | A | 1/1981 | Hutchins et al. |
| 4,252,126 | A | 2/1981 | Mandl |
| 4,253,501 | A | 3/1981 | Ogle |
| 4,259,985 | A | 4/1981 | Bergmann |
| 4,260,180 | A | 4/1981 | Halushka et al. |
| 4,262,824 | A | 4/1981 | Hrynewycz |
| 4,262,880 | A | 4/1981 | Danko et al. |
| 4,274,327 | A | 6/1981 | Olsgaard |
| 4,275,868 | A | 6/1981 | Crone |
| 4,280,494 | A | 7/1981 | Cosgrove, Jr. et al. |
| 4,284,073 | A | 8/1981 | Krause et al. |
| 4,306,705 | A | 12/1981 | Svensson |
| 4,310,420 | A | 1/1982 | Konishi et al. |
| 4,311,586 | A | 1/1982 | Baldwin et al. |
| 4,315,582 | A | 2/1982 | Micallef |
| 4,319,568 | A | 3/1982 | Tregoning |
| 4,326,697 | A | 4/1982 | Autage et al. |
| 4,328,833 | A | 5/1982 | Aurther |
| 4,328,834 | A | 5/1982 | Oates, Sr. et al. |
| 4,336,000 | A | 6/1982 | Jorgensen et al. |
| 4,340,148 | A | 7/1982 | Beckham |
| 4,340,153 | A | 7/1982 | Spivey |

(56) References Cited

U.S. PATENT DOCUMENTS

| | | |
|---|---|---|
| 4,341,153 A | 7/1982 | Bowser |
| 4,352,636 A | 10/1982 | Patterson et al. |
| 4,360,969 A | 11/1982 | Collier |
| 4,365,635 A | 12/1982 | Bowman |
| 4,366,816 A | 1/1983 | Bayard et al. |
| 4,369,779 A | 1/1983 | Spencer |
| 4,372,336 A | 2/1983 | Cornell et al. |
| 4,392,847 A | 7/1983 | Whitney et al. |
| 4,392,849 A | 7/1983 | Petre et al. |
| 4,396,385 A * | 8/1983 | Kelly ............... A61M 5/14216 604/152 |
| 4,398,757 A | 8/1983 | Floyd et al. |
| 4,402,310 A | 9/1983 | Kimura |
| 4,402,420 A | 9/1983 | Chernack |
| 4,405,294 A | 9/1983 | Albarda |
| 4,405,829 A | 9/1983 | Rivest et al. |
| 4,407,644 A | 10/1983 | Brotherston et al. |
| 4,409,966 A | 10/1983 | Lambrecht et al. |
| 4,410,003 A | 10/1983 | Sandling |
| 4,412,834 A | 11/1983 | Kulin et al. |
| 4,431,009 A | 2/1984 | Marino, Jr. et al. |
| 4,433,973 A | 2/1984 | Kurtz et al. |
| 4,434,822 A | 3/1984 | Bellamy et al. |
| 4,444,198 A | 4/1984 | Petre |
| 4,447,230 A | 5/1984 | Gula et al. |
| 4,450,624 A | 5/1984 | Collier |
| 4,453,927 A | 6/1984 | Sinko |
| 4,468,914 A | 9/1984 | Pestes |
| 4,469,121 A | 9/1984 | Moen |
| 4,469,935 A | 9/1984 | Candela |
| 4,470,771 A | 9/1984 | Hall et al. |
| 4,475,666 A | 10/1984 | Bilbrey et al. |
| 4,478,388 A | 10/1984 | George |
| 4,479,759 A | 10/1984 | Zeitz |
| 4,479,760 A | 10/1984 | Bilstad et al. |
| 4,479,761 A | 10/1984 | Bilstad et al. |
| 4,479,762 A | 10/1984 | Bilstad et al. |
| 4,479,792 A | 10/1984 | Lazarus et al. |
| 4,482,347 A | 11/1984 | Borsanyi |
| 4,484,599 A | 11/1984 | Hanover et al. |
| 4,491,156 A | 1/1985 | Lee, II |
| 4,494,730 A | 1/1985 | George |
| 4,503,333 A | 3/1985 | Kulin et al. |
| RE31,873 E | 4/1985 | Howes |
| 4,508,103 A | 4/1985 | Calisi |
| 4,508,367 A | 4/1985 | Oreopoulos et al. |
| 4,511,359 A | 4/1985 | Vaillancourt |
| 4,512,364 A | 4/1985 | Phillips |
| 4,512,764 A | 4/1985 | Wunsch |
| 4,525,165 A | 6/1985 | Fischell |
| 4,535,820 A | 8/1985 | Raines |
| 4,536,140 A | 8/1985 | Guthrie |
| 4,544,949 A | 10/1985 | Kurihara |
| 4,551,133 A | 11/1985 | Zegers de Beyl et al. |
| 4,551,146 A | 11/1985 | Rogers |
| 4,552,513 A | 11/1985 | Miller et al. |
| 4,559,036 A | 12/1985 | Wunsch |
| 4,559,043 A | 12/1985 | Whitehouse et al. |
| 4,560,327 A | 12/1985 | Bez et al. |
| 4,563,175 A | 1/1986 | LaFond |
| 4,572,231 A | 2/1986 | Katayama |
| 4,575,317 A | 3/1986 | Lindner |
| 4,579,823 A | 4/1986 | Ryder |
| 4,585,009 A | 4/1986 | Barker et al. |
| 4,585,941 A | 4/1986 | Bergner |
| 4,595,495 A | 6/1986 | Yotam et al. |
| 4,595,595 A | 6/1986 | Gunnerson et al. |
| 4,604,093 A | 8/1986 | Brown et al. |
| 4,610,670 A | 9/1986 | Spencer |
| 4,610,790 A | 9/1986 | Reti et al. |
| 4,613,325 A | 9/1986 | Abrams |
| 4,624,664 A | 11/1986 | Peluso et al. |
| 4,633,307 A | 12/1986 | Honda |
| 4,634,426 A | 1/1987 | Kamen |
| 4,636,144 A | 1/1987 | Abe et al. |
| 4,636,204 A | 1/1987 | Christopherson et al. |
| 4,637,817 A | 1/1987 | Archibald et al. |
| 4,655,197 A | 4/1987 | Atkinson |
| 4,655,762 A | 4/1987 | Rogers |
| 4,662,906 A | 5/1987 | Matkovich et al. |
| 4,673,395 A | 6/1987 | Phillips |
| 4,681,513 A | 7/1987 | Saito et al. |
| 4,682,170 A | 7/1987 | Kubota et al. |
| 4,684,102 A | 8/1987 | Dykstra |
| 4,687,408 A | 8/1987 | Klambauer |
| 4,687,472 A | 8/1987 | Gross |
| 4,695,276 A | 9/1987 | Shinno et al. |
| 4,708,605 A | 11/1987 | Orlita |
| 4,710,166 A | 12/1987 | Thompson et al. |
| 4,723,945 A | 2/1988 | Theiling |
| 4,734,011 A | 3/1988 | Hall, Jr. |
| 4,737,148 A | 4/1988 | Blake |
| 4,750,643 A | 6/1988 | Wortrich |
| 4,752,292 A | 6/1988 | Lopez et al. |
| 4,754,786 A | 7/1988 | Roberts |
| 4,756,706 A | 7/1988 | Kerns et al. |
| 4,758,235 A | 7/1988 | Tu |
| 4,775,173 A | 10/1988 | Sauer |
| 4,775,369 A | 10/1988 | Schwartz |
| 4,778,152 A | 10/1988 | Logman |
| 4,778,447 A | 10/1988 | Velde et al. |
| 4,781,687 A | 11/1988 | Wall |
| 4,783,273 A | 11/1988 | Knutsson et al. |
| 4,790,728 A | 12/1988 | Dwyer |
| 4,795,426 A | 1/1989 | Jones |
| 4,795,441 A | 1/1989 | Bhatt |
| 4,797,207 A | 1/1989 | Honganen et al. |
| 4,798,590 A | 1/1989 | O'Leary et al. |
| 4,807,666 A | 2/1989 | Morse |
| 4,808,077 A | 2/1989 | Kan et al. |
| 4,810,168 A | 3/1989 | Nogami et al. |
| 4,810,241 A | 3/1989 | Rogers |
| 4,813,210 A | 3/1989 | Masuda et al. |
| 4,819,637 A | 4/1989 | Dormandy, Jr. et al. |
| 4,820,288 A | 4/1989 | Isono |
| 4,821,996 A | 4/1989 | Bellotti et al. |
| 4,823,833 A | 4/1989 | Hogan et al. |
| 4,824,342 A | 4/1989 | Buck |
| 4,828,557 A | 5/1989 | Persidsky |
| 4,834,108 A | 5/1989 | Vaillancourt |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,838,860 A | 6/1989 | Groshong et al. |
| 4,840,620 A | 6/1989 | Kobayashi et al. |
| 4,844,052 A | 7/1989 | Iwakoshi et al. |
| 4,844,413 A | 7/1989 | Weber et al. |
| 4,846,797 A | 7/1989 | Howson et al. |
| 4,850,972 A | 7/1989 | Schulman et al. |
| 4,850,980 A | 7/1989 | Lentz et al. |
| 4,853,521 A | 8/1989 | Claeys et al. |
| 4,854,301 A | 8/1989 | Nakajima |
| 4,854,324 A | 8/1989 | Hirschman et al. |
| 4,854,836 A | 8/1989 | Borsanyi |
| 4,857,056 A | 8/1989 | Talonn |
| 4,874,359 A | 10/1989 | White et al. |
| 4,874,378 A | 10/1989 | Hillstead |
| 4,875,718 A | 10/1989 | Marken |
| 4,879,880 A | 11/1989 | Harrison |
| 4,880,014 A | 11/1989 | Zarowitz et al. |
| 4,883,409 A | 11/1989 | Strohmeier et al. |
| 4,883,641 A | 11/1989 | Wicks et al. |
| 4,887,208 A | 12/1989 | Schneider et al. |
| 4,887,554 A | 12/1989 | Whitford |
| 4,890,817 A | 1/1990 | Uri |
| 4,898,579 A | 2/1990 | Groshong et al. |
| 4,904,245 A | 2/1990 | Chen et al. |
| 4,909,783 A | 3/1990 | Morrison |
| 4,913,624 A | 4/1990 | Seki et al. |
| 4,915,591 A | 4/1990 | Funke |
| 4,915,688 A | 4/1990 | Bischof et al. |
| 4,925,444 A | 5/1990 | Orkin et al. |
| 4,929,818 A | 5/1990 | Bradbury et al. |
| 4,935,005 A | 6/1990 | Haines |

(56) References Cited

U.S. PATENT DOCUMENTS

| | | |
|---|---|---|
| 4,936,753 A | 6/1990 | Kozumplik, Jr. et al. |
| 4,936,832 A | 6/1990 | Vaillancourt |
| 4,941,308 A | 7/1990 | Grabenkort et al. |
| 4,941,809 A | 7/1990 | Pinkerton |
| 4,943,279 A | 7/1990 | Samiotes et al. |
| 4,946,047 A | 8/1990 | Kurokawa et al. |
| 4,946,256 A | 8/1990 | Woodruff |
| 4,946,434 A | 8/1990 | Plaisted et al. |
| 4,946,439 A | 8/1990 | Eggers |
| 4,947,856 A | 8/1990 | Beard |
| 4,950,245 A | 8/1990 | Brown et al. |
| 4,950,260 A | 8/1990 | Bonaldo |
| 4,954,129 A | 9/1990 | Giuliani et al. |
| 4,954,239 A | 9/1990 | Mueller |
| 4,966,199 A | 10/1990 | Rusch |
| 4,966,579 A | 10/1990 | Polaschegg |
| 4,967,797 A | 11/1990 | Manska |
| 4,969,879 A | 11/1990 | Lichte |
| 4,976,687 A | 12/1990 | Martin |
| 4,978,335 A | 12/1990 | Arthur, III |
| 4,981,467 A | 1/1991 | Bobo, Jr. et al. |
| 4,981,469 A | 1/1991 | Whitehouse et al. |
| 4,982,760 A | 1/1991 | Mustaklem |
| 4,987,335 A | 1/1991 | Yamamoto et al. |
| 4,993,546 A | 2/1991 | Southard |
| 4,994,035 A | 2/1991 | Mokros |
| 5,002,055 A | 3/1991 | Merki et al. |
| 5,004,472 A | 4/1991 | Wallace et al. |
| 5,009,654 A | 4/1991 | Minshall et al. |
| 5,014,494 A | 5/1991 | George |
| 5,015,157 A | 5/1991 | Pinkerton et al. |
| 5,020,980 A | 6/1991 | Pinkerton |
| 5,024,587 A | 6/1991 | Maurer |
| 5,029,973 A | 7/1991 | Rink |
| 5,032,112 A | 7/1991 | Fairchild et al. |
| 5,033,650 A | 7/1991 | Colin et al. |
| 5,033,777 A | 7/1991 | Blenkush |
| 5,037,067 A | 8/1991 | Ray |
| 5,044,889 A | 9/1991 | Pinkerton |
| 5,044,900 A | 9/1991 | Cavallaro |
| 5,044,902 A | 9/1991 | Malbec |
| 5,047,012 A | 9/1991 | Leuschner et al. |
| 5,047,021 A | 9/1991 | Utterberg |
| 5,048,537 A | 9/1991 | Messinger |
| 5,049,047 A | 9/1991 | Polaschegg et al. |
| 5,053,002 A | 10/1991 | Barlow |
| 5,053,003 A | 10/1991 | Dadson et al. |
| 5,057,076 A | 10/1991 | Polaschegg |
| 5,057,088 A | 10/1991 | Narayanan et al. |
| 5,059,173 A | 10/1991 | Sacco |
| 5,061,243 A | 10/1991 | Winchell et al. |
| 5,062,774 A | 11/1991 | Kramer et al. |
| 5,066,282 A | 11/1991 | Wijay et al. |
| 5,074,334 A | 12/1991 | Onodera |
| 5,078,580 A | 1/1992 | Miller et al. |
| 5,078,683 A | 1/1992 | Sancoff et al. |
| 5,084,031 A | 1/1992 | Todd et al. |
| 5,087,086 A | 2/1992 | Snedeker |
| 5,088,981 A | 2/1992 | Howson et al. |
| 5,088,984 A | 2/1992 | Fields |
| 5,092,037 A | 3/1992 | Pinkerton |
| 5,097,840 A | 3/1992 | Wallace et al. |
| 5,098,395 A | 3/1992 | Fields |
| 5,098,407 A | 3/1992 | Okamura |
| 5,100,103 A | 3/1992 | Conley et al. |
| 5,100,380 A | 3/1992 | Epstein et al. |
| 5,102,253 A | 4/1992 | Pugliesi-Conti et al. |
| 5,104,158 A | 4/1992 | Meyer et al. |
| 5,104,374 A | 4/1992 | Bishko et al. |
| 5,104,387 A | 4/1992 | Pokorney et al. |
| 5,108,365 A | 4/1992 | Woods, Jr. |
| 5,113,904 A | 5/1992 | Aslanian |
| 5,113,906 A | 5/1992 | Hoegner |
| 5,116,086 A | 5/1992 | Psajd |
| 5,117,870 A | 6/1992 | Goodale et al. |
| 5,128,121 A | 7/1992 | Berg et al. |
| 5,133,336 A | 7/1992 | Savitt et al. |
| 5,135,000 A | 8/1992 | Akselrod et al. |
| 5,135,026 A | 8/1992 | Manska |
| 5,135,500 A | 8/1992 | Zdeb |
| 5,143,257 A | 9/1992 | Austin et al. |
| RE34,114 E | 10/1992 | Lindner |
| 5,153,827 A | 10/1992 | Coutre et al. |
| 5,156,538 A | 10/1992 | Lee |
| 5,163,909 A | 11/1992 | Stewart |
| 5,165,728 A | 11/1992 | Mayer |
| 5,171,229 A | 12/1992 | McNeil et al. |
| 5,176,415 A | 1/1993 | Choksi |
| 5,180,896 A | 1/1993 | Gibby et al. |
| 5,184,742 A | 2/1993 | DeCaprio et al. |
| 5,188,603 A | 2/1993 | Vaillancourt |
| 5,190,071 A | 3/1993 | Sule |
| 5,190,534 A | 3/1993 | Kendell |
| 5,191,878 A | 3/1993 | Iida et al. |
| 5,192,269 A | 3/1993 | Poli et al. |
| 5,196,007 A | 3/1993 | Ellman et al. |
| 5,196,197 A | 3/1993 | Talwar et al. |
| 5,197,438 A | 3/1993 | Kumano et al. |
| 5,199,604 A | 4/1993 | Palmer et al. |
| 5,205,322 A | 4/1993 | Merick et al. |
| 5,207,641 A | 5/1993 | Allton |
| 5,207,642 A | 5/1993 | Orkin et al. |
| 5,213,376 A | 5/1993 | Szabo |
| 5,213,483 A | 5/1993 | Flaherty et al. |
| 5,221,267 A | 6/1993 | Folden |
| 5,226,886 A | 7/1993 | Skakoon et al. |
| 5,230,614 A | 7/1993 | Zanger et al. |
| 5,234,193 A | 8/1993 | Neal, Jr. et al. |
| 5,237,309 A | 8/1993 | Frantz et al. |
| 5,242,390 A | 9/1993 | Goldrath |
| 5,243,982 A | 9/1993 | Moestl et al. |
| 5,246,347 A | 9/1993 | Davis |
| 5,246,354 A | 9/1993 | Pardinas |
| 5,249,579 A | 10/1993 | Hobbs et al. |
| 5,251,873 A | 10/1993 | Atkinson et al. |
| 5,254,101 A | 10/1993 | Trombley, III |
| 5,260,020 A | 11/1993 | Wilk et al. |
| 5,267,174 A | 11/1993 | Kaufman et al. |
| 5,267,964 A | 12/1993 | Karg |
| 5,269,756 A | 12/1993 | Dryden |
| 5,273,537 A | 12/1993 | Haskvitz et al. |
| 5,274,218 A | 12/1993 | Urata et al. |
| 5,280,809 A | 1/1994 | Tive |
| 5,281,111 A | 1/1994 | Plambeck et al. |
| 5,286,178 A | 2/1994 | Schaef |
| 5,288,290 A | 2/1994 | Brody |
| 5,292,308 A | 3/1994 | Ryan |
| 5,310,007 A | 5/1994 | Parikh |
| 5,310,997 A | 5/1994 | Roach et al. |
| 5,312,233 A | 5/1994 | Tanny et al. |
| 5,313,992 A | 5/1994 | Grabenkort |
| 5,314,416 A | 5/1994 | Lewis et al. |
| 5,317,506 A | 5/1994 | Coutre et al. |
| 5,318,328 A | 6/1994 | Dawson |
| 5,322,423 A | 6/1994 | Heck et al. |
| 5,328,463 A | 7/1994 | Barton et al. |
| 5,329,459 A | 7/1994 | Kaufman et al. |
| 5,334,163 A | 8/1994 | Sinnett |
| 5,339,799 A | 8/1994 | Kami et al. |
| 5,340,359 A | 8/1994 | Segura Badia |
| 5,346,470 A | 9/1994 | Hobbs et al. |
| 5,349,625 A | 9/1994 | Born et al. |
| 5,354,273 A | 10/1994 | Hagen |
| 5,361,761 A | 11/1994 | Van Lysel et al. |
| 5,362,291 A | 11/1994 | Williamson, IV |
| 5,362,948 A | 11/1994 | Morimoto |
| 5,368,562 A | 11/1994 | Blomquist et al. |
| 5,376,070 A | 12/1994 | Purvis et al. |
| 5,377,718 A | 1/1995 | Sand |
| 5,378,231 A | 1/1995 | Johnson et al. |
| 5,382,232 A | 1/1995 | Hague et al. |
| 5,382,242 A | 1/1995 | Horton et al. |
| 5,385,540 A | 1/1995 | Abbott et al. |
| 5,411,382 A | 5/1995 | Duensing |

(56) References Cited

U.S. PATENT DOCUMENTS

| | | |
|---|---|---|
| 5,411,485 A | 5/1995 | Tennican et al. |
| 5,411,490 A | 5/1995 | Tennican et al. |
| 5,413,280 A | 5/1995 | Taylor |
| 5,413,566 A | 5/1995 | Sevrain et al. |
| 5,415,528 A | 5/1995 | Ogden et al. |
| 5,417,213 A | 5/1995 | Prince |
| 5,417,667 A | 5/1995 | Tennican et al. |
| 5,419,354 A | 5/1995 | Krynicki |
| 5,423,323 A | 6/1995 | Orth |
| 5,429,485 A | 7/1995 | Dodge |
| 5,431,627 A | 7/1995 | Pastrone et al. |
| 5,443,453 A | 8/1995 | Walker et al. |
| 5,445,621 A | 8/1995 | Poli et al. |
| 5,449,206 A | 9/1995 | Lockwood |
| 5,450,847 A | 9/1995 | Kaempfe et al. |
| 5,452,748 A | 9/1995 | Simmons et al. |
| 5,454,792 A | 10/1995 | Tennican et al. |
| 5,454,972 A | 10/1995 | Williams et al. |
| 5,458,128 A | 10/1995 | Polanyi et al. |
| 5,460,609 A | 10/1995 | O'Donnell |
| 5,462,251 A | 10/1995 | Kawabe |
| 5,464,391 A | 11/1995 | Devale |
| 5,466,228 A | 11/1995 | Evans |
| 5,468,240 A | 11/1995 | Gentelia et al. |
| 5,472,320 A | 12/1995 | Weisbrodt |
| 5,472,403 A | 12/1995 | Cornacchia et al. |
| 5,474,099 A | 12/1995 | Boehmer et al. |
| 5,474,683 A | 12/1995 | Bryant et al. |
| 5,478,338 A | 12/1995 | Reynard |
| 5,480,386 A | 1/1996 | Brohy et al. |
| 5,482,171 A | 1/1996 | Palmer |
| 5,482,448 A | 1/1996 | Atwater et al. |
| 5,485,831 A | 1/1996 | Holdsworth et al. |
| 5,489,196 A | 2/1996 | Lee |
| 5,489,265 A | 2/1996 | Montalvo et al. |
| 5,492,535 A | 2/1996 | Reed et al. |
| 5,494,036 A | 2/1996 | Uber, III et al. |
| 5,494,822 A | 2/1996 | Sadri |
| 5,496,273 A | 3/1996 | Pastrone et al. |
| 5,498,253 A | 3/1996 | Aswad et al. |
| 5,507,412 A | 4/1996 | Ebert et al. |
| 5,507,733 A | 4/1996 | Larkin et al. |
| 5,515,851 A | 5/1996 | Goldstein |
| 5,522,798 A | 6/1996 | Johnson et al. |
| 5,529,463 A | 6/1996 | Layer et al. |
| 5,531,679 A | 7/1996 | Schulman et al. |
| 5,531,697 A | 7/1996 | Olsen et al. |
| 5,531,698 A | 7/1996 | Olsen |
| 5,531,712 A | 7/1996 | Malcolm et al. |
| 5,533,978 A | 7/1996 | Teirstein |
| 5,547,470 A | 8/1996 | Johnson et al. |
| 5,551,850 A | 9/1996 | Williamson et al. |
| 5,552,130 A | 9/1996 | Kraus et al. |
| 5,553,619 A | 9/1996 | Prince |
| 5,558,669 A | 9/1996 | Reynard |
| 5,560,317 A | 10/1996 | Bunyan et al. |
| 5,569,181 A | 10/1996 | Heilman et al. |
| 5,569,208 A | 10/1996 | Woelpper et al. |
| 5,573,505 A | 11/1996 | Johnson et al. |
| 5,573,515 A | 11/1996 | Wilson et al. |
| 5,578,016 A | 11/1996 | Zinger |
| 5,579,767 A | 12/1996 | Prince |
| 5,580,530 A | 12/1996 | Kowatsch et al. |
| 5,583,902 A | 12/1996 | Bae |
| 5,588,816 A | 12/1996 | Abbott et al. |
| 5,590,654 A | 1/1997 | Prince |
| 5,592,940 A | 1/1997 | Kampfe et al. |
| 5,603,900 A | 2/1997 | Clark et al. |
| 5,609,572 A | 3/1997 | Lang |
| 5,616,124 A | 4/1997 | Hague et al. |
| 5,620,433 A | 4/1997 | Aswad et al. |
| 5,632,606 A | 5/1997 | Jacobsen et al. |
| 5,638,793 A | 6/1997 | Rapp et al. |
| 5,639,220 A | 6/1997 | Hayakawa |
| 5,645,538 A | 7/1997 | Richmond |
| 5,647,854 A | 7/1997 | Olsen et al. |
| 5,655,897 A | 8/1997 | Neftel et al. |
| 5,687,208 A | 11/1997 | Bae et al. |
| 5,697,899 A | 12/1997 | Hillman et al. |
| 5,704,914 A | 1/1998 | Stocking et al. |
| 5,714,060 A | 2/1998 | Kenley et al. |
| 5,718,568 A | 2/1998 | Neftel et al. |
| 5,718,569 A | 2/1998 | Holst |
| 5,718,570 A | 2/1998 | Beckett et al. |
| 5,720,415 A | 2/1998 | Morningstar |
| 5,733,105 A | 3/1998 | Beckett et al. |
| 5,739,508 A | 4/1998 | Uber, III |
| 5,741,125 A | 4/1998 | Neftel et al. |
| 5,741,126 A | 4/1998 | Stearns et al. |
| 5,741,710 A | 4/1998 | Ek |
| 5,746,718 A | 5/1998 | Steyn |
| 5,749,854 A | 5/1998 | Shen |
| 5,755,683 A | 5/1998 | Houle et al. |
| 5,764,159 A | 6/1998 | Neftel |
| 5,768,405 A | 6/1998 | Makram-Ebeid |
| 5,772,585 A | 6/1998 | Lavin et al. |
| 5,779,675 A | 7/1998 | Reilly et al. |
| 5,782,611 A | 7/1998 | Neftel et al. |
| 5,785,691 A | 7/1998 | Vetter et al. |
| 5,788,669 A | 8/1998 | Peterson |
| 5,795,333 A | 8/1998 | Reilly et al. |
| 5,799,649 A | 9/1998 | Prince |
| 5,799,987 A | 9/1998 | Sampson |
| 5,800,397 A | 9/1998 | Wilson et al. |
| 5,803,510 A | 9/1998 | Dorsey, III |
| 5,803,712 A | 9/1998 | Davis et al. |
| 5,806,519 A | 9/1998 | Evans, III et al. |
| 5,808,203 A | 9/1998 | Nolan, Jr. et al. |
| 5,817,067 A | 10/1998 | Tsukada |
| 5,817,068 A | 10/1998 | Urrutia |
| 5,819,229 A | 10/1998 | Boppe |
| 5,822,544 A | 10/1998 | Chaco et al. |
| 5,827,262 A | 10/1998 | Neftel et al. |
| 5,830,195 A | 11/1998 | Peters et al. |
| 5,832,959 A | 11/1998 | Szymczakowski et al. |
| 5,840,026 A | 11/1998 | Uber, III et al. |
| RE35,997 E | 12/1998 | Pinkerton |
| 5,843,037 A | 12/1998 | Uber, III |
| 5,852,231 A | 12/1998 | Kaji |
| 5,853,096 A | 12/1998 | Bartur et al. |
| 5,865,797 A | 2/1999 | Zeeman |
| 5,873,861 A | 2/1999 | Hitchins et al. |
| 5,882,343 A | 3/1999 | Wilson et al. |
| 5,885,216 A | 3/1999 | Evans, III et al. |
| 5,901,745 A | 5/1999 | Buchtel |
| 5,901,944 A | 5/1999 | Ramakrishnan et al. |
| 5,911,687 A | 6/1999 | Sato et al. |
| 5,913,434 A | 6/1999 | Fukuhara et al. |
| 5,916,165 A | 6/1999 | Duchon et al. |
| 5,916,197 A | 6/1999 | Reilly et al. |
| 5,916,201 A | 6/1999 | Wilson, Jr. et al. |
| 5,920,054 A | 7/1999 | Uber, III |
| 5,924,074 A | 7/1999 | Evans |
| 5,927,885 A | 7/1999 | Duez et al. |
| 5,934,496 A | 8/1999 | Mogard et al. |
| 5,935,099 A | 8/1999 | Peterson et al. |
| 5,937,885 A | 8/1999 | Sampson |
| 5,947,935 A | 9/1999 | Kazousky et al. |
| 5,947,958 A | 9/1999 | Woodard et al. |
| 5,953,453 A | 9/1999 | Fan et al. |
| 5,954,700 A | 9/1999 | Kovelman |
| 5,961,303 A | 10/1999 | King |
| 5,964,485 A | 10/1999 | Hame et al. |
| 5,964,583 A | 10/1999 | Danby |
| 5,968,014 A | 10/1999 | Neftel et al. |
| 5,972,292 A | 10/1999 | Demeo |
| 5,980,501 A | 11/1999 | Gray |
| 5,984,378 A | 11/1999 | Ostrander et al. |
| 5,988,587 A | 11/1999 | Duchon et al. |
| 5,992,691 A | 11/1999 | Post et al. |
| 5,993,654 A | 11/1999 | Black |
| 6,022,053 A | 2/2000 | Hukuda |
| 6,036,458 A | 3/2000 | Cole et al. |
| 6,039,011 A | 3/2000 | Agalarov et al. |

(56) References Cited

U.S. PATENT DOCUMENTS

| | | |
|---|---|---|
| RE36,648 E | 4/2000 | Uber, III et al. |
| 6,047,259 A | 4/2000 | Campbell et al. |
| 6,068,617 A | 5/2000 | Richmond |
| 6,077,055 A | 6/2000 | Vilks |
| 6,077,259 A | 6/2000 | Caizza et al. |
| 6,079,691 A | 6/2000 | Dragone |
| 6,083,205 A | 7/2000 | Bourne et al. |
| 6,085,574 A | 7/2000 | Neftel et al. |
| 6,092,722 A | 7/2000 | Heinrichs et al. |
| 6,096,011 A | 8/2000 | Trombley, III et al. |
| 6,099,502 A | 8/2000 | Duchon et al. |
| 6,099,511 A | 8/2000 | Devos et al. |
| 6,105,829 A | 8/2000 | Snodgrass et al. |
| 6,106,498 A | 8/2000 | Friedli et al. |
| 6,110,152 A | 8/2000 | Kovelman |
| RE36,871 E | 9/2000 | Epstein et al. |
| 6,113,068 A | 9/2000 | Ryan |
| 6,120,490 A | 9/2000 | Neftel |
| 6,123,686 A | 9/2000 | Olsen et al. |
| 6,146,109 A | 11/2000 | Davis et al. |
| 6,149,627 A | 11/2000 | Uber, III |
| 6,155,307 A | 12/2000 | Vanneste |
| 6,155,607 A | 12/2000 | Hewitt et al. |
| 6,157,914 A | 12/2000 | Seto et al. |
| 6,158,467 A | 12/2000 | Loo |
| 6,164,044 A | 12/2000 | Porfano et al. |
| 6,164,279 A | 12/2000 | Tweedle |
| 6,189,704 B1 | 2/2001 | Dennehey et al. |
| 6,197,000 B1 | 3/2001 | Reilly et al. |
| 6,200,111 B1 | 3/2001 | Foss |
| 6,210,361 B1 | 4/2001 | Kamen et al. |
| 6,220,487 B1 | 4/2001 | Srivastava et al. |
| 6,221,045 B1 | 4/2001 | Duchon et al. |
| 6,224,346 B1 | 5/2001 | Denenburg |
| 6,244,838 B1 | 6/2001 | Couillard et al. |
| 6,250,052 B1 | 6/2001 | Porfano et al. |
| 6,260,021 B1 | 7/2001 | Wong et al. |
| 6,261,270 B1 | 7/2001 | Gault et al. |
| 6,263,641 B1 | 7/2001 | Odell et al. |
| 6,269,704 B1 | 8/2001 | Ziv et al. |
| 6,270,478 B1 | 8/2001 | Mernoee |
| 6,272,469 B1 | 8/2001 | Koritzinsky et al. |
| 6,280,430 B1 | 8/2001 | Neftel et al. |
| 6,283,761 B1 | 9/2001 | Joao |
| 6,285,285 B1 | 9/2001 | Mongrenier |
| 6,293,756 B1 | 9/2001 | Andersson |
| 6,305,724 B1 | 10/2001 | Sampson |
| 6,306,117 B1 | 10/2001 | Uber, III |
| 6,312,227 B1 | 11/2001 | Davis |
| 6,317,623 B1 | 11/2001 | Griffiths et al. |
| 6,319,236 B1 | 11/2001 | Boeck |
| 6,339,718 B1 | 1/2002 | Zatezalo et al. |
| 6,344,030 B1 | 2/2002 | Duchon et al. |
| RE37,602 E | 3/2002 | Uber, III et al. |
| 6,361,051 B1 | 3/2002 | Babin |
| 6,364,279 B1 | 4/2002 | Neftel et al. |
| 6,366,206 B1 | 4/2002 | Ishikawa et al. |
| 6,368,080 B1 | 4/2002 | Sipin |
| 6,371,444 B1 | 4/2002 | Hahn et al. |
| 6,385,483 B1 | 5/2002 | Uber, III et al. |
| 6,397,098 B1 | 5/2002 | Uber, III et al. |
| 6,398,513 B1 | 6/2002 | Amsler et al. |
| 6,402,717 B1 | 6/2002 | Reilly et al. |
| 6,418,966 B2 | 7/2002 | Loo |
| 6,428,518 B1 | 8/2002 | Brengle et al. |
| 6,436,072 B1 | 8/2002 | Kullas et al. |
| 6,440,107 B1 | 8/2002 | Trombley, III et al. |
| 6,442,418 B1 | 8/2002 | Evans, III et al. |
| 6,443,496 B2 | 9/2002 | Campau |
| 6,454,162 B1 | 9/2002 | Teller |
| 6,457,488 B2 | 10/2002 | Loo |
| 6,468,261 B1 | 10/2002 | Small et al. |
| 6,468,424 B1 | 10/2002 | Doenig et al. |
| 6,471,671 B1 | 10/2002 | Urick et al. |
| 6,471,674 B1 | 10/2002 | Emig et al. |
| 6,475,192 B1 | 11/2002 | Reilly et al. |
| 6,488,660 B1 | 12/2002 | Futterknecht |
| 6,491,189 B2 | 12/2002 | Friedman |
| 6,501,068 B1 | 12/2002 | Eisenhauer |
| 6,502,937 B2 | 1/2003 | Yang |
| 6,503,225 B1 | 1/2003 | Kirsch et al. |
| 6,511,459 B1 | 1/2003 | Fago |
| 6,511,472 B1 | 1/2003 | Hayman et al. |
| 6,519,569 B1 | 2/2003 | White et al. |
| 6,520,930 B2 | 2/2003 | Critchlow et al. |
| 6,530,907 B1 | 3/2003 | Sugahara et al. |
| 6,536,742 B2 | 3/2003 | Lotz et al. |
| RE38,074 E | 4/2003 | Recinella et al. |
| 6,540,486 B2 | 4/2003 | Amsler et al. |
| 6,544,228 B1 | 4/2003 | Heitmeier |
| 6,558,125 B1 | 5/2003 | Futterknecht |
| 6,558,343 B1 | 5/2003 | Neftel |
| 6,568,923 B2 | 5/2003 | Ikuta |
| 6,575,930 B1 | 6/2003 | Trombley, III et al. |
| 6,607,179 B2 | 8/2003 | Moretti et al. |
| 6,616,000 B1 | 9/2003 | Renz |
| 6,623,455 B2 | 9/2003 | Small et al. |
| 6,626,355 B2 | 9/2003 | Sasse et al. |
| 6,626,862 B1 | 9/2003 | Duchon et al. |
| 6,634,871 B2 | 10/2003 | Ikuta |
| 6,635,033 B1 | 10/2003 | Hill et al. |
| 6,638,258 B2 | 10/2003 | Schwartz et al. |
| 6,638,263 B1 | 10/2003 | Theeuwes et al. |
| 6,640,689 B2 | 11/2003 | Mitsui et al. |
| 6,643,537 B1 | 11/2003 | Zatezalo et al. |
| 6,648,017 B2 | 11/2003 | Lamas et al. |
| 6,649,829 B2 | 11/2003 | Garber et al. |
| 6,652,489 B2 | 11/2003 | Trocki et al. |
| 6,655,658 B2 | 12/2003 | Neal et al. |
| 6,656,157 B1 | 12/2003 | Duchon et al. |
| 6,666,839 B2 | 12/2003 | Utterberg et al. |
| 6,669,681 B2 | 12/2003 | Jepson et al. |
| 6,673,033 B1 | 1/2004 | Sciulli et al. |
| 6,676,104 B1 | 1/2004 | Tillander |
| 6,679,529 B2 | 1/2004 | Johnson et al. |
| 6,682,044 B2 | 1/2004 | Miller |
| 6,685,673 B2 | 2/2004 | Minezaki et al. |
| 6,685,831 B2 | 2/2004 | Donig et al. |
| 6,688,211 B1 | 2/2004 | Viet |
| 6,699,219 B2 | 3/2004 | Emig et al. |
| 6,702,557 B2 | 3/2004 | Kim et al. |
| 6,708,944 B2 | 3/2004 | Pfeil et al. |
| 6,708,948 B2 | 3/2004 | Nosel et al. |
| 6,716,193 B1 | 4/2004 | Neftel |
| 6,722,705 B2 | 4/2004 | Korkor |
| 6,726,656 B2 | 4/2004 | Kamen et al. |
| 6,731,971 B2 | 5/2004 | Evans et al. |
| 6,733,477 B2 | 5/2004 | Cowan et al. |
| 6,733,478 B2 | 5/2004 | Reilly et al. |
| 6,742,680 B2 | 6/2004 | Friedman |
| 6,742,992 B2 | 6/2004 | Davis |
| 6,743,202 B2 | 6/2004 | Hirschman et al. |
| 6,749,090 B2 | 6/2004 | Bailey |
| 6,749,402 B2 | 6/2004 | Hogan et al. |
| 6,755,630 B2 | 6/2004 | Kim et al. |
| 6,767,034 B2 | 7/2004 | Clinche et al. |
| 6,786,885 B2 | 9/2004 | Hochman et al. |
| 6,796,965 B2 | 9/2004 | Dumaresq-Lucas et al. |
| 6,814,726 B1 | 11/2004 | Lauer |
| 6,821,267 B2 | 11/2004 | Veillon, Jr. et al. |
| 6,857,617 B2 | 2/2005 | Forberg et al. |
| 6,861,954 B2 | 3/2005 | Levin |
| 6,869,425 B2 | 3/2005 | Briggs et al. |
| 6,871,660 B2 | 3/2005 | Hampsch |
| 6,874,759 B2 | 4/2005 | Aoshima et al. |
| 6,880,808 B2 | 4/2005 | McPeak et al. |
| 6,884,255 B1 | 4/2005 | Newton |
| 6,889,074 B2 | 5/2005 | Uber et al. |
| 6,892,996 B2 | 5/2005 | Starchevich |
| 6,897,374 B2 | 5/2005 | Garber et al. |
| 6,901,283 B2 | 5/2005 | Evans et al. |
| 6,908,118 B2 | 6/2005 | Fumioka |
| 6,911,025 B2 | 6/2005 | Miyahara |
| 6,918,893 B2 | 7/2005 | Houde et al. |

(56) References Cited

U.S. PATENT DOCUMENTS

| | | |
|---|---|---|
| 6,929,235 B1 | 8/2005 | Height et al. |
| 6,929,236 B1 | 8/2005 | Height et al. |
| 6,937,150 B2 | 8/2005 | Medema et al. |
| 6,939,302 B2 | 9/2005 | Griffiths et al. |
| 6,945,431 B2 | 9/2005 | Miller |
| 6,945,954 B2 | 9/2005 | Hochman et al. |
| 6,953,450 B2 | 10/2005 | Baldwin et al. |
| 6,953,453 B2 | 10/2005 | Recinella et al. |
| 6,958,058 B1 | 10/2005 | Hunter, Sr. et al. |
| 6,967,974 B1 | 11/2005 | Partyka |
| 6,972,001 B2 | 12/2005 | Emig et al. |
| 6,976,628 B2 | 12/2005 | Krupa |
| 6,981,960 B2 | 1/2006 | Cho et al. |
| 6,985,870 B2 | 1/2006 | Martucci et al. |
| 7,005,078 B2 | 2/2006 | Van Lintel et al. |
| 7,014,624 B2 | 3/2006 | Meythaler et al. |
| 7,017,800 B2 | 3/2006 | Ulrich et al. |
| 7,017,948 B2 | 3/2006 | Sunohara et al. |
| 7,022,256 B2 | 4/2006 | Uegami et al. |
| 7,040,598 B2 | 5/2006 | Raybuck |
| 7,041,081 B2 | 5/2006 | Minezaki et al. |
| 7,041,941 B2 | 5/2006 | Faries et al. |
| 7,047,058 B1 | 5/2006 | Dvorsky et al. |
| 7,047,984 B2 | 5/2006 | Blattner et al. |
| 7,047,994 B2 | 5/2006 | McPeak et al. |
| 7,048,193 B2 | 5/2006 | Tsukada et al. |
| 7,060,049 B2 | 6/2006 | Trombley et al. |
| 7,063,785 B2 | 6/2006 | Hiraku et al. |
| 7,070,589 B2 | 7/2006 | Lolachi et al. |
| 7,079,886 B2 | 7/2006 | Zatezalo et al. |
| 7,083,605 B2 | 8/2006 | Miyahara |
| 7,091,864 B2 | 8/2006 | Veitch et al. |
| 7,094,216 B2 | 8/2006 | Trombley, III et al. |
| 7,097,209 B2 | 8/2006 | Unger et al. |
| 7,097,690 B2 | 8/2006 | Usher et al. |
| 7,108,184 B2 | 9/2006 | Mase et al. |
| 7,115,113 B2 | 10/2006 | Evans et al. |
| 7,128,347 B2 | 10/2006 | Kerin |
| 7,137,974 B2 | 11/2006 | Almasian et al. |
| 7,144,382 B2 | 12/2006 | Broek et al. |
| 7,156,056 B2 | 1/2007 | Lemke et al. |
| 7,160,020 B2 | 1/2007 | Sand |
| 7,169,128 B2 | 1/2007 | Kriesel et al. |
| 7,169,135 B2 | 1/2007 | Duchon et al. |
| 7,172,572 B2 | 2/2007 | Diamond et al. |
| 7,174,923 B2 | 2/2007 | Schorn et al. |
| 7,178,515 B2 | 2/2007 | Carpenter et al. |
| 7,189,320 B2 | 3/2007 | Takao et al. |
| 7,193,519 B2 | 3/2007 | Root et al. |
| 7,195,624 B2 | 3/2007 | Lockwood et al. |
| 7,201,185 B2 | 4/2007 | Poppe et al. |
| 7,204,421 B2 | 4/2007 | Austin |
| 7,213,760 B2 | 5/2007 | Mase et al. |
| 7,213,767 B2 | 5/2007 | Tethrake et al. |
| 7,214,039 B2 | 5/2007 | Angove |
| 7,217,105 B2 | 5/2007 | Angove |
| 7,236,936 B2 | 6/2007 | White et al. |
| 7,241,285 B1 | 7/2007 | Dikeman |
| 7,252,308 B2 | 8/2007 | Thilly |
| 7,267,532 B2 | 9/2007 | Krebs |
| 7,278,778 B2 | 10/2007 | Sand |
| 7,309,014 B2 | 12/2007 | Truong et al. |
| 7,311,503 B2 | 12/2007 | Van Lintel et al. |
| 7,326,188 B1 | 2/2008 | Russell et al. |
| 7,331,770 B2 | 2/2008 | Oyaski |
| 7,337,538 B2 | 3/2008 | Moutafis et al. |
| 7,347,837 B2 | 3/2008 | Azzolini |
| 7,364,657 B2 | 4/2008 | Mandrusov et al. |
| 7,367,358 B2 | 5/2008 | Malcolm |
| 7,374,555 B2 | 5/2008 | Heinz et al. |
| 7,374,718 B2 | 5/2008 | Dhara et al. |
| 7,431,989 B2 | 10/2008 | Sakhrani et al. |
| 7,451,742 B2 | 11/2008 | Gibson et al. |
| 7,451,959 B2 | 11/2008 | Matzner |
| 7,452,349 B2 | 11/2008 | Miyahara |
| 7,481,795 B2 | 1/2009 | Thompson et al. |
| 7,497,840 B2 | 3/2009 | Neftel et al. |
| 7,531,098 B2 | 5/2009 | Robinson et al. |
| 7,553,304 B2 | 6/2009 | Neftel |
| 7,569,047 B2 | 8/2009 | Utterberg |
| 7,618,397 B2 | 11/2009 | Hicks |
| 7,618,412 B2 | 11/2009 | Chernack |
| 7,695,445 B2 | 4/2010 | Yuki |
| 7,713,250 B2 | 5/2010 | Harding et al. |
| 7,731,155 B2 | 6/2010 | Funamura et al. |
| 7,740,288 B2 | 6/2010 | Mantell |
| 7,762,989 B2 | 7/2010 | Simpson |
| 7,766,883 B2 | 8/2010 | Reilly et al. |
| 7,771,383 B2 | 8/2010 | Truitt et al. |
| 7,782,467 B2 | 8/2010 | Chappel |
| 7,887,308 B2 | 2/2011 | Navarro |
| 7,887,509 B2 | 2/2011 | Thiebaud et al. |
| 7,901,386 B2 | 3/2011 | Hishikawa et al. |
| 7,901,727 B2 | 3/2011 | Hofmann et al. |
| 7,905,861 B2 | 3/2011 | Rhinehart et al. |
| 7,918,243 B2 | 4/2011 | Diodati et al. |
| 7,935,077 B2 | 5/2011 | Thor et al. |
| 7,938,454 B2 | 5/2011 | Buchanan et al. |
| 7,951,112 B2 | 5/2011 | Patzer |
| 7,963,951 B2 | 6/2011 | Kitani et al. |
| 7,984,730 B2 | 7/2011 | Ziv et al. |
| 3,007,487 A1 | 8/2011 | Patrick et al. |
| 8,011,897 B2 | 9/2011 | Raleigh et al. |
| 8,012,144 B2 | 9/2011 | Moberg |
| 8,038,667 B2 | 10/2011 | Racz et al. |
| 8,061,687 B2 | 11/2011 | Anderson |
| 8,062,003 B2 | 11/2011 | Goertzen et al. |
| 8,062,009 B2 | 11/2011 | Cueni |
| 8,133,035 B2 | 3/2012 | Wolff |
| 8,133,205 B2 | 3/2012 | Rhinehart et al. |
| 8,140,274 B2 | 3/2012 | Gagel et al. |
| 8,147,464 B2 | 4/2012 | Spohn et al. |
| 8,157,547 B2 | 4/2012 | Hendrikus Oude Vrielink |
| 8,172,199 B2 | 5/2012 | Ushigusa et al. |
| 8,257,267 B2 | 9/2012 | Thornton |
| 8,287,724 B2 | 10/2012 | Slepicka et al. |
| 8,308,167 B2 | 11/2012 | Balsells et al. |
| 8,308,456 B2 | 11/2012 | Moubayed |
| 8,343,128 B2 | 1/2013 | Nagao et al. |
| 8,353,688 B2 | 1/2013 | Navarro |
| 8,360,757 B2 | 1/2013 | Knauper et al. |
| 8,382,712 B2 | 2/2013 | Kim |
| 8,425,463 B2 * | 4/2013 | Patrick .................. G16H 20/17 |
| | | 604/82 |
| 8,545,440 B2 * | 10/2013 | Patrick ................ A61M 5/1452 |
| | | 604/82 |
| 8,944,780 B2 | 2/2015 | Reilly |
| 9,044,542 B2 * | 6/2015 | Patrick .................. A61B 8/465 |
| 9,358,333 B2 | 6/2016 | Trombley, III et al. |
| 9,393,441 B2 | 7/2016 | Hoffman et al. |
| 9,408,971 B2 | 8/2016 | Carlyon |
| 9,480,791 B2 | 11/2016 | Reilly |
| 9,566,381 B2 | 2/2017 | Barron et al. |
| 10,046,106 B2 | 8/2018 | Cowan et al. |
| 10,420,902 B2 | 9/2019 | Cowan et al. |
| 10,549,084 B2 | 2/2020 | Sokolov et al. |
| 2001/0016704 A1 | 8/2001 | Zadno-Azizi et al. |
| 2002/0010437 A1 | 1/2002 | Lopez et al. |
| 2002/0025267 A1 | 2/2002 | Lieber et al. |
| 2002/0026148 A1 | 2/2002 | Uber et al. |
| 2002/0061375 A1 | 5/2002 | Cartledge et al. |
| 2002/0084437 A1 | 7/2002 | Nitsche et al. |
| 2002/0093192 A1 | 7/2002 | Matkovich |
| 2002/0099334 A1 | 7/2002 | Hanson et al. |
| 2002/0115933 A1 | 8/2002 | Duchon et al. |
| 2002/0123716 A1 | 9/2002 | Vandiver et al. |
| 2002/0123737 A1 | 9/2002 | Hart et al. |
| 2002/0139088 A1 | 10/2002 | Woodworth et al. |
| 2002/0143294 A1 | 10/2002 | Duchon et al. |
| 2002/0144429 A1 | 10/2002 | Cowan et al. |
| 2002/0172615 A1 | 11/2002 | Woodworth et al. |
| 2002/0188259 A1 | 12/2002 | Hickle et al. |
| 2002/0191487 A1 | 12/2002 | Sand |
| 2003/0050556 A1 | 3/2003 | Uber et al. |

(56) References Cited

U.S. PATENT DOCUMENTS

| | | |
|---|---|---|
| 2003/0071233 A1 | 4/2003 | Stewart et al. |
| 2003/0140929 A1 | 7/2003 | Wilkes et al. |
| 2003/0155385 A1 | 8/2003 | Sohoel et al. |
| 2003/0171670 A1 | 9/2003 | Gumb et al. |
| 2003/0216643 A1 | 11/2003 | Zatezalo et al. |
| 2004/0008123 A1 | 1/2004 | Carrender et al. |
| 2004/0021120 A1 | 2/2004 | Turnau, III et al. |
| 2004/0064041 A1 | 4/2004 | Lazzaro et al. |
| 2004/0074281 A1 | 4/2004 | Lobdell et al. |
| 2004/0092908 A1 | 5/2004 | Harper et al. |
| 2004/0104271 A1 | 6/2004 | Martucci et al. |
| 2004/0116862 A1 | 6/2004 | Ray |
| 2004/0122369 A1 | 6/2004 | Schriver et al. |
| 2004/0130438 A1 | 7/2004 | Garber |
| 2004/0143225 A1 | 7/2004 | Callan et al. |
| 2004/0171982 A1 | 9/2004 | Danchin |
| 2004/0193328 A1 | 9/2004 | Zaitsu et al. |
| 2004/0193453 A1 | 9/2004 | Butterfield et al. |
| 2004/0199075 A1 | 10/2004 | Evans et al. |
| 2004/0221904 A1 | 11/2004 | Usher et al. |
| 2004/0222180 A1 | 11/2004 | Wicks et al. |
| 2004/0241023 A1 | 12/2004 | Pinkerton et al. |
| 2005/0010175 A1 | 1/2005 | Beedon et al. |
| 2005/0019187 A1 | 1/2005 | Whitworth et al. |
| 2005/0019195 A1 | 1/2005 | Schnabl |
| 2005/0033232 A1 | 2/2005 | Kriesel |
| 2005/0057042 A1 | 3/2005 | Wicks |
| 2005/0070978 A1 | 3/2005 | Bek et al. |
| 2005/0075611 A1 | 4/2005 | Hetzler et al. |
| 2005/0082828 A1 | 4/2005 | Wicks et al. |
| 2005/0084410 A1 | 4/2005 | Meyer et al. |
| 2005/0089994 A1 | 4/2005 | Neftel |
| 2005/0090805 A1 | 4/2005 | Shaw et al. |
| 2005/0113763 A1 | 5/2005 | Reynolds |
| 2005/0118048 A1 | 6/2005 | Traxinger |
| 2005/0129569 A1 | 6/2005 | Zhao et al. |
| 2005/0139532 A1 | 6/2005 | Hershberger et al. |
| 2005/0194722 A1 | 9/2005 | Muratoglu et al. |
| 2005/0194723 A1 | 9/2005 | Muratoglu et al. |
| 2005/0211905 A1 | 9/2005 | Stark |
| 2005/0211934 A1 | 9/2005 | Garber et al. |
| 2005/0234394 A1 | 10/2005 | Ross |
| 2005/0245883 A1 | 11/2005 | Baldwin |
| 2005/0267418 A1 | 12/2005 | Fournie et al. |
| 2005/0277873 A1 | 12/2005 | Stewart et al. |
| 2005/0277890 A1 | 12/2005 | Stewart et al. |
| 2006/0009699 A1 | 1/2006 | Roteliuk et al. |
| 2006/0013849 A1 | 1/2006 | Strickler et al. |
| 2006/0016897 A1 | 1/2006 | Yasuda et al. |
| 2006/0049629 A1 | 3/2006 | Naumann et al. |
| 2006/0065739 A1 | 3/2006 | Falls, Jr. et al. |
| 2006/0069356 A1 | 3/2006 | Witowski |
| 2006/0076419 A1 | 4/2006 | Johnson |
| 2006/0086363 A1 | 4/2006 | Qin et al. |
| 2006/0091209 A1 | 5/2006 | He |
| 2006/0108008 A1 | 5/2006 | Guala |
| 2006/0116639 A1 | 6/2006 | Russell |
| 2006/0122555 A1 | 6/2006 | Hochman |
| 2006/0127252 A1 | 6/2006 | Caddell |
| 2006/0131423 A1 | 6/2006 | Truong |
| 2006/0153716 A1 | 7/2006 | Shoji et al. |
| 2006/0155248 A1 | 7/2006 | Hashimoto et al. |
| 2006/0167415 A1 | 7/2006 | Nemoto |
| 2006/0175832 A1 | 8/2006 | Mueller et al. |
| 2006/0184008 A1 | 8/2006 | Zatezalo et al. |
| 2006/0224128 A1 | 10/2006 | Lurvey et al. |
| 2006/0235297 A1 | 10/2006 | Kawamoto |
| 2006/0243804 A1 | 11/2006 | Christoffersen et al. |
| 2007/0049870 A1 | 3/2007 | Gray et al. |
| 2007/0053788 A1 | 3/2007 | Zhao |
| 2007/0055195 A1 | 3/2007 | Browne |
| 2007/0056871 A1 | 3/2007 | Griffiths et al. |
| 2007/0060874 A1 | 3/2007 | Nesbitt et al. |
| 2007/0071616 A1 | 3/2007 | Owen et al. |
| 2007/0073246 A1 | 3/2007 | Simon |
| 2007/0078203 A1 | 4/2007 | Gohill |
| 2007/0084524 A1 | 4/2007 | Py |
| 2007/0085049 A1 | 4/2007 | Houle et al. |
| 2007/0088268 A1 | 4/2007 | Edwards et al. |
| 2007/0088271 A1 | 4/2007 | Richards |
| 2007/0096906 A1 | 5/2007 | Lyons et al. |
| 2007/0100282 A1 | 5/2007 | Small et al. |
| 2007/0100315 A1 | 5/2007 | Traxinger |
| 2007/0100316 A1 | 5/2007 | Traxinger |
| 2007/0106264 A1 | 5/2007 | Proulx et al. |
| 2007/0112265 A1 | 5/2007 | Zatezalo et al. |
| 2007/0115125 A1 | 5/2007 | Lyon et al. |
| 2007/0119929 A1 | 5/2007 | Swan et al. |
| 2007/0123620 A1 | 5/2007 | Nayak et al. |
| 2007/0125870 A1 | 6/2007 | Mase et al. |
| 2007/0129680 A1 | 6/2007 | Hagg et al. |
| 2007/0148010 A1 | 6/2007 | Michels et al. |
| 2007/0159337 A1 | 7/2007 | Tethrake et al. |
| 2007/0167910 A1 | 7/2007 | Tennican et al. |
| 2007/0167919 A1 | 7/2007 | Nemoto et al. |
| 2007/0187475 A1 | 8/2007 | MacLeod |
| 2007/0191760 A1 | 8/2007 | Iguchi et al. |
| 2007/0196223 A1 | 8/2007 | Hogan et al. |
| 2007/0197974 A1 | 8/2007 | Gibson |
| 2007/0204612 A1 | 9/2007 | Klimowicz et al. |
| 2007/0213662 A1 | 9/2007 | Kalafut et al. |
| 2007/0225601 A1 | 9/2007 | Uber, III et al. |
| 2007/0237658 A1 | 10/2007 | Burns et al. |
| 2007/0244437 A1 | 10/2007 | Castillo et al. |
| 2007/0287954 A1 | 12/2007 | Zhao et al. |
| 2008/0014105 A1 | 1/2008 | Neftel et al. |
| 2008/0024310 A1 | 1/2008 | Baker et al. |
| 2008/0034959 A1 | 2/2008 | Vu |
| 2008/0045919 A1 | 2/2008 | Jakob et al. |
| 2008/0045925 A1* | 2/2008 | Stepovich ......... A61M 5/16827 604/82 |
| 2008/0058711 A1 | 3/2008 | Neftel et al. |
| 2008/0069970 A1 | 3/2008 | Wu |
| 2008/0071228 A1 | 3/2008 | Wu et al. |
| 2008/0089799 A1 | 4/2008 | O'Connell |
| 2008/0097342 A1 | 4/2008 | Gordin |
| 2008/0131300 A1 | 6/2008 | Junod et al. |
| 2008/0172002 A1 | 7/2008 | Bell et al. |
| 2008/0177250 A1 | 7/2008 | Howlett et al. |
| 2008/0213115 A1 | 9/2008 | Hilger et al. |
| 2008/0281265 A1 | 11/2008 | Hochman |
| 2008/0287887 A1 | 11/2008 | Mack et al. |
| 2008/0294029 A1 | 11/2008 | Piveteau et al. |
| 2008/0294040 A1 | 11/2008 | Mohiuddin et al. |
| 2008/0319401 A1 | 12/2008 | Funamura et al. |
| 2009/0012466 A1 | 1/2009 | Zhao et al. |
| 2009/0043253 A1 | 2/2009 | Podaima |
| 2009/0060764 A1 | 3/2009 | Mitzlaff et al. |
| 2009/0102192 A1 | 4/2009 | Ziman |
| 2009/0105629 A1 | 4/2009 | Grant et al. |
| 2009/0118695 A1 | 5/2009 | Neftel |
| 2009/0152098 A1 | 6/2009 | Hooper et al. |
| 2009/0173903 A1 | 7/2009 | Kaneko et al. |
| 2009/0182309 A1 | 7/2009 | Muffly |
| 2009/0187139 A1 | 7/2009 | Mastalli et al. |
| 2009/0199917 A1 | 8/2009 | Vallet et al. |
| 2009/0216192 A1 | 8/2009 | Schriver et al. |
| 2009/0240233 A1 | 9/2009 | Neftel |
| 2009/0277276 A1 | 11/2009 | Evering et al. |
| 2009/0324676 A1 | 12/2009 | Hofmann et al. |
| 2010/0012207 A1 | 1/2010 | Satoh et al. |
| 2010/0022968 A1 | 1/2010 | Kitani |
| 2010/0022988 A1 | 1/2010 | Wochner et al. |
| 2010/0028170 A1 | 2/2010 | Schneeberger et al. |
| 2010/0030070 A1 | 2/2010 | Duffour et al. |
| 2010/0049170 A1 | 2/2010 | Solomon et al. |
| 2010/0056975 A1 | 3/2010 | Dale et al. |
| 2010/0096302 A1 | 4/2010 | Astle et al. |
| 2010/0106012 A1 | 4/2010 | De Marco |
| 2010/0113924 A1 | 5/2010 | Hajicek et al. |
| 2010/0116365 A1 | 5/2010 | McCarty |
| 2010/0130918 A1 | 5/2010 | Elahi |
| 2010/0130922 A1 | 5/2010 | Borlaug et al. |
| 2010/0191106 A1 | 7/2010 | Koyama |

(56) References Cited

U.S. PATENT DOCUMENTS

| | | | |
|---|---|---|---|
| 2010/0256569 A1 | 10/2010 | Cachemaille et al. |
| 2010/0280458 A1 | 11/2010 | Cachemaille et al. |
| 2010/0286467 A1 | 11/2010 | Pesach et al. |
| 2010/0298699 A1 | 11/2010 | Reilly et al. |
| 2010/0305508 A1 | 12/2010 | Franks |
| 2010/0324504 A1 | 12/2010 | Chappel et al. |
| 2011/0002802 A1 | 1/2011 | Capone et al. |
| 2011/0024657 A1 | 2/2011 | Tower |
| 2011/0049866 A1 | 3/2011 | Trombley, III et al. |
| 2011/0054397 A1 | 3/2011 | Menot et al. |
| 2011/0054440 A1 | 3/2011 | Lewis |
| 2011/0132480 A1 | 6/2011 | Chappel |
| 2011/0142688 A1 | 6/2011 | Chappel et al. |
| 2011/0144585 A1 | 6/2011 | Bianchi et al. |
| 2011/0178493 A1 | 7/2011 | Okiyama |
| 2011/0196291 A1 | 8/2011 | Vischer et al. |
| 2011/0200456 A1 | 8/2011 | Patzer |
| 2011/0240158 A1 | 10/2011 | Py |
| 2011/0282302 A1 | 11/2011 | Lopez et al. |
| 2011/0308651 A1 | 12/2011 | Ziv et al. |
| 2011/0313394 A1 | 12/2011 | Bobo, Sr. |
| 2012/0046610 A1 | 2/2012 | Rankin |
| 2012/0116317 A1 | 5/2012 | Kassab et al. |
| 2012/0123257 A1 | 5/2012 | Stokes, Jr. et al. |
| 2012/0148415 A1 | 6/2012 | Brueckner |
| 2013/0072880 A1 | 3/2013 | Finke |
| 2013/0079581 A1 | 3/2013 | Agamaite et al. |
| 2013/0116620 A1 | 5/2013 | Rotem et al. |
| 2013/0123567 A1 | 5/2013 | Agamaite et al. |
| 2013/0131579 A1 | 5/2013 | Mantell et al. |
| 2013/0211248 A1 | 8/2013 | Cowan et al. |
| 2013/0245565 A1 | 9/2013 | Leak et al. |
| 2013/0331634 A1 | 12/2013 | Kaintz et al. |
| 2014/0107480 A1 | 4/2014 | Spohn et al. |
| 2014/0224829 A1 | 8/2014 | Capone et al. |
| 2014/0296786 A1 | 10/2014 | Servansky et al. |
| 2014/0342447 A1 | 11/2014 | Aviles et al. |
| 2015/0174338 A1 | 6/2015 | Takemoto |

FOREIGN PATENT DOCUMENTS

| | | | |
|---|---|---|---|
| CA | 2574551 A1 | 7/2008 |
| CN | 2829775 Y | 10/2006 |
| DE | 3726452 A1 | 2/1989 |
| DE | 3838689 C1 | 6/1990 |
| DE | 4037797 C1 | 2/1992 |
| DE | 4121568 A1 | 10/1992 |
| DE | 4336336 A1 | 5/1994 |
| DE | 4426387 A1 | 8/1995 |
| DE | 102013104018 A1 | 10/2014 |
| EP | 0068555 A1 | 1/1983 |
| EP | 0189491 A1 | 8/1986 |
| EP | 0204977 A1 | 12/1986 |
| EP | 0337924 A2 | 10/1989 |
| EP | 0343501 A2 | 11/1989 |
| EP | 0503670 A2 | 9/1992 |
| EP | 0600448 A2 | 6/1994 |
| EP | 0619122 A1 | 10/1994 |
| EP | 0650738 A1 | 5/1995 |
| EP | 0702966 A2 | 3/1996 |
| EP | 1331020 A1 | 7/2003 |
| EP | 1817499 A1 | 8/2007 |
| EP | 2409720 A1 | 1/2012 |
| EP | 1834664 B1 | 5/2013 |
| FR | 2493708 A1 | 5/1982 |
| FR | 2561949 A1 | 10/1985 |
| FR | 2594496 A1 | 8/1987 |
| FR | 2715310 A1 | 7/1995 |
| FR | 2847342 A1 | 5/2004 |
| GB | 511715 A | 8/1939 |
| GB | 884234 A | 12/1961 |
| GB | 1511715 A | 5/1978 |
| GB | 2020735 A | 11/1979 |
| GB | 2038929 A | 7/1980 |
| GB | 2044888 A | 10/1980 |
| GB | 2139708 A | 11/1984 |
| GB | 2207749 A | 2/1989 |
| GB | 2252656 A | 8/1992 |
| JP | S57102578 A | 6/1982 |
| JP | H04241778 A | 8/1992 |
| JP | H0521502 A | 1/1993 |
| JP | H05272685 A | 10/1993 |
| JP | H06142199 A | 5/1994 |
| JP | H06142200 A | 5/1994 |
| JP | 1997506316 | 6/1997 |
| JP | 2001145697 A | 5/2001 |
| JP | 2001512342 A | 8/2001 |
| JP | 2002510979 A | 4/2002 |
| JP | 2003210574 A | 7/2003 |
| JP | 2006528710 A | 12/2006 |
| JP | 2007014492 A | 1/2007 |
| JP | 2007113433 A | 5/2007 |
| JP | 4268658 B1 | 5/2009 |
| JP | 2010527273 A | 8/2010 |
| JP | 6184495 B2 | 8/2017 |
| NL | 9500612 A | 11/1996 |
| WO | 8001754 A1 | 9/1980 |
| WO | 8500292 A1 | 1/1985 |
| WO | 8803815 A1 | 6/1988 |
| WO | 9103404 A1 | 3/1991 |
| WO | 9320864 A1 | 10/1993 |
| WO | 9323740 A1 | 11/1993 |
| WO | 9415664 A1 | 7/1994 |
| WO | 9531643 A1 | 11/1995 |
| WO | 9611025 A1 | 4/1996 |
| WO | 9621151 A1 | 7/1996 |
| WO | 9632975 A1 | 10/1996 |
| WO | 9700093 A1 | 1/1997 |
| WO | 9702853 A1 | 1/1997 |
| WO | 9714493 A1 | 4/1997 |
| WO | 9716217 A1 | 5/1997 |
| WO | 9806446 A2 | 2/1998 |
| WO | 9820920 A2 | 5/1998 |
| WO | 9835712 A1 | 8/1998 |
| WO | 9924095 A2 | 5/1999 |
| WO | 9934846 A2 | 7/1999 |
| WO | 9938558 A1 | 8/1999 |
| WO | 0202164 A1 | 1/2002 |
| WO | 0204049 A1 | 1/2002 |
| WO | 0248589 A1 | 6/2002 |
| WO | 02096487 A1 | 12/2002 |
| WO | 03039646 A1 | 5/2003 |
| WO | 03044488 A1 | 5/2003 |
| WO | 03063929 A1 | 8/2003 |
| WO | 2005106251 A1 | 11/2005 |
| WO | 2005110007 A2 | 11/2005 |
| WO | 2006002817 A1 | 1/2006 |
| WO | 2006056828 A1 | 6/2006 |
| WO | 2007141681 A2 | 12/2007 |
| WO | 2008086349 A1 | 7/2008 |
| WO | 2008086631 A1 | 7/2008 |
| WO | 2008141337 A1 | 11/2008 |
| WO | 2009067200 A2 | 5/2009 |
| WO | 2009149367 A1 | 12/2009 |
| WO | 2011033440 A1 | 3/2011 |
| WO | 2012170961 A1 | 12/2012 |
| WO | 2013043868 A1 | 3/2013 |
| WO | 2013043881 A1 | 3/2013 |
| WO | 2013059563 A1 | 4/2013 |
| WO | 2013104665 A1 | 7/2013 |
| WO | 2015066506 A2 | 5/2015 |

OTHER PUBLICATIONS

AseptiQuik X Connector Catalog, Oct. 2012.
Catalog Valves, http://www.minivalve.com/newsite/index.php/en/home—last visited Sep. 23, 2016.
Colder; Products Company., "Asepti-Quik Product Catalog", accessed online on Oct. 11, 2013.
Connection Solutions for Biopharmaceutical Processes, May 2012.
Debiotech Switzerland, Sales Brochure, Lausanne 9, Switzerland, distributed week of Dec. 1, 1996 at the Radiological Society of North American in Chicago, Illinois.

(56) References Cited

OTHER PUBLICATIONS

DoseGuard Valved Bottle Adapter System Brochure.
Hadaway; Lynn., "Needleless Connectors: A Primer on Terminology", Journal of Infusion Nursing, Jan./Feb. 2010, 33(1), 22-31.
Pure Fit SC True Sterile Connections . . . Outside the Clean Room Catalog, Saint-Gobain Performance Plastics. 2008.
ReadyMate Disposable Aseptic Connectors, Operation Manual, Jul. 2009.
Single-Use Bags 50 to 500 Liters Catalog, Jun. 2010.
Site-Scrub IPA Device—last visited Sep. 23, 2016.
TakeOne Aseptic Sampling System Brochure, 2010.
UFP; Technologies., "BioShell Suspension Pack Brochure", accessed online on May 7, 2013.
"UltraPort Swabbable Port Stopcocks, B. Braun Sharing Expertise.", accessed online on Apr. 14, 2014.
"Supplementary European Search Report from EP Application No. EP12842335.", dated Feb. 16, 2015.
"Written Opinion and International Search Report from PCT Application No. PCT/US2016/012434", dated May 6, 2016.

\* cited by examiner

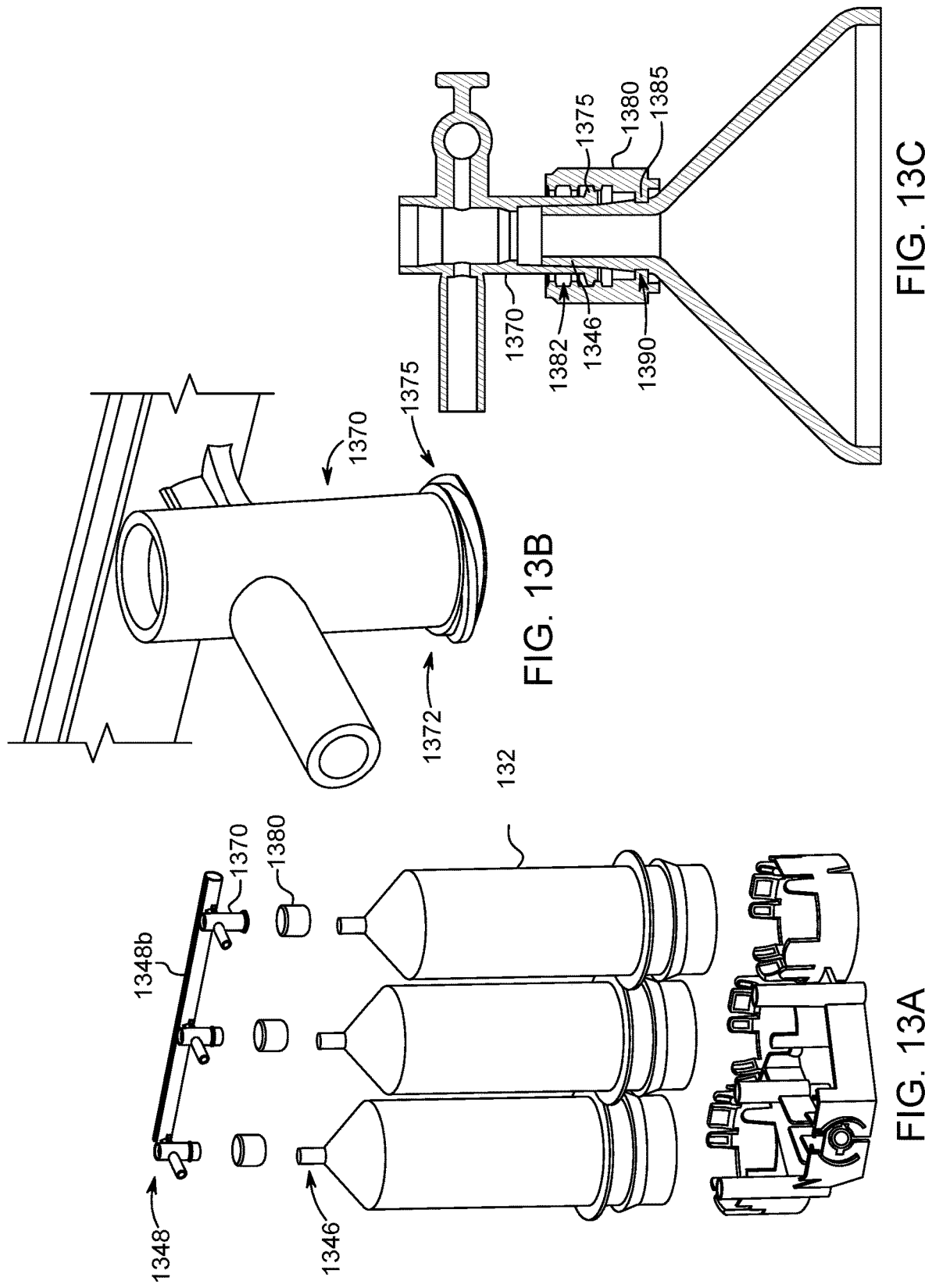

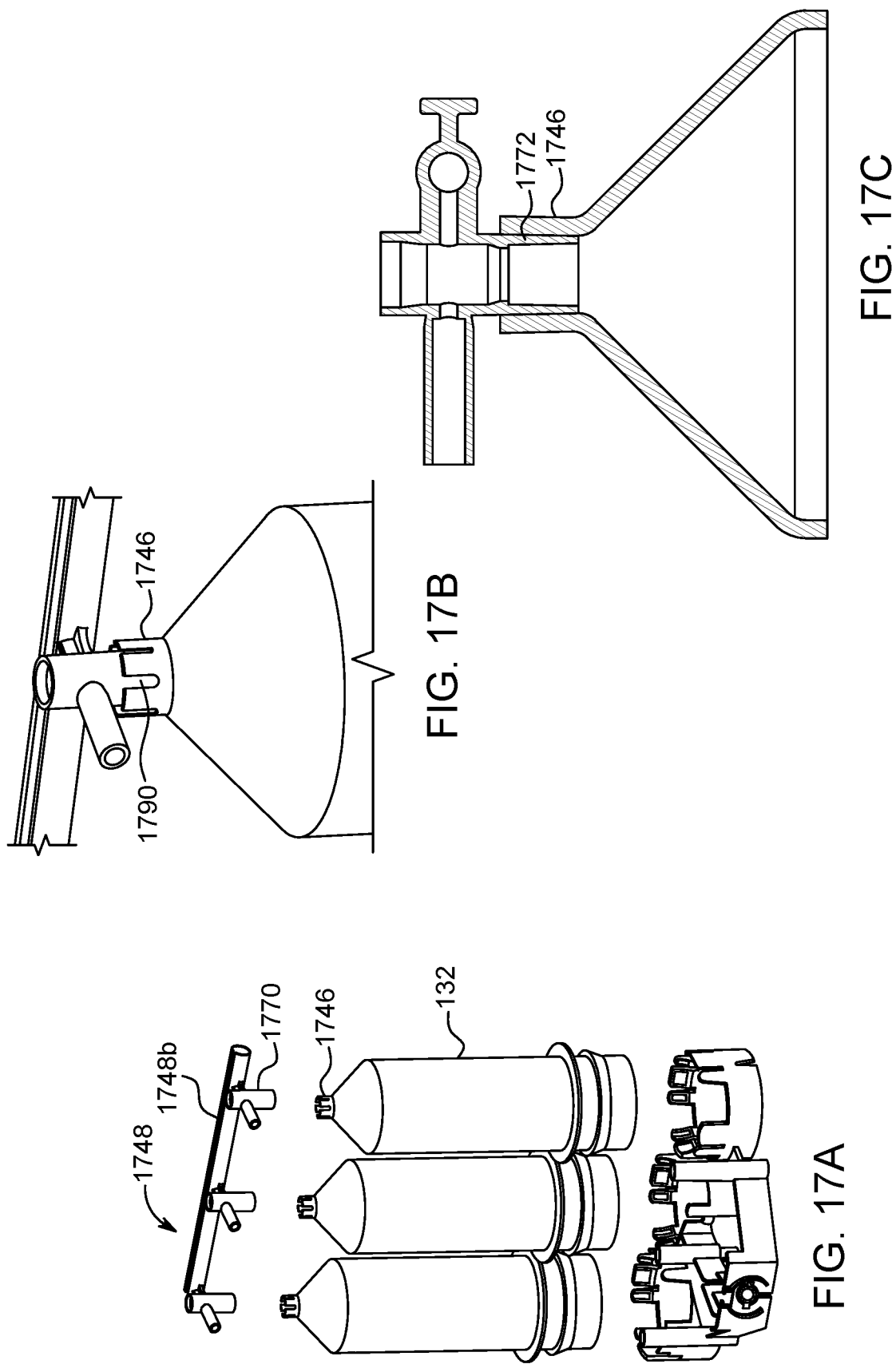

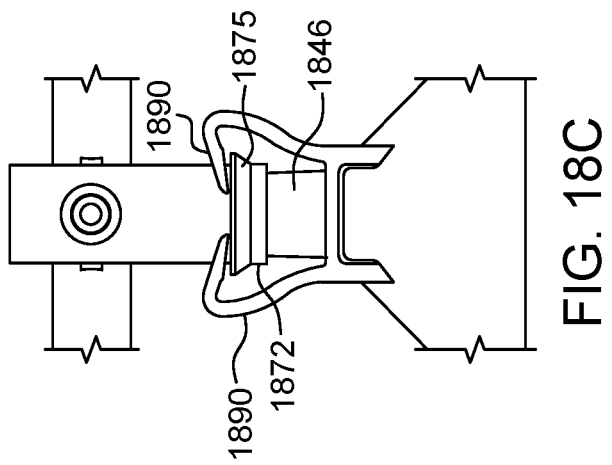
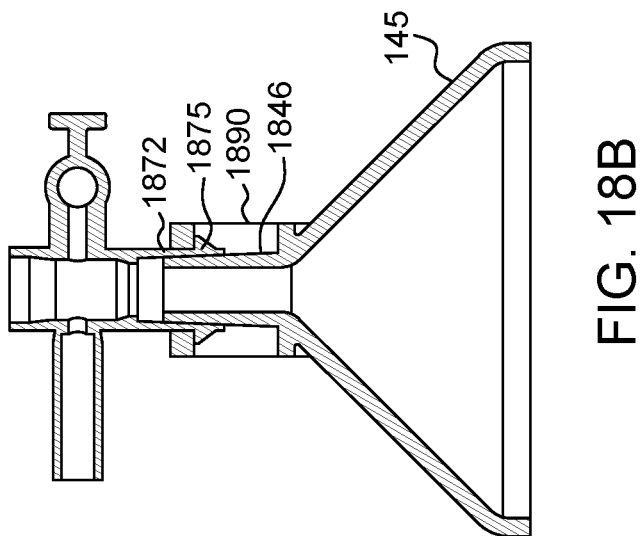
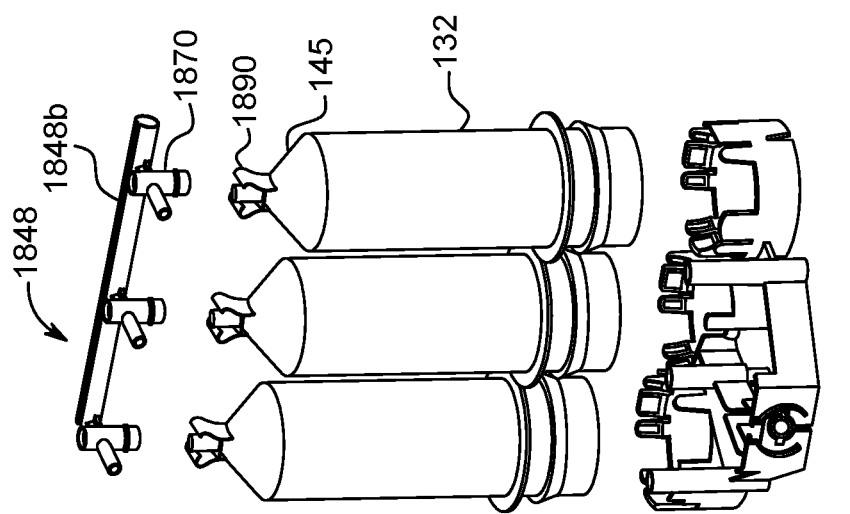
FIG. 18C
FIG. 18B
FIG. 18A

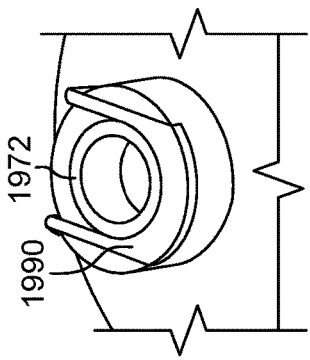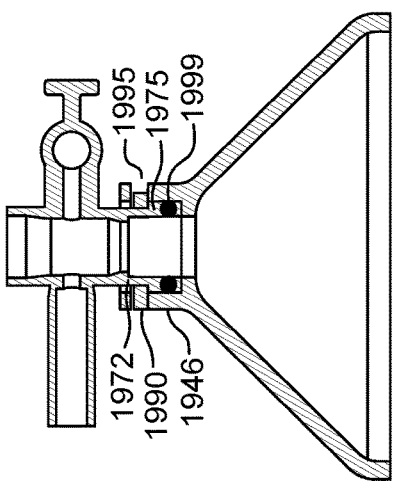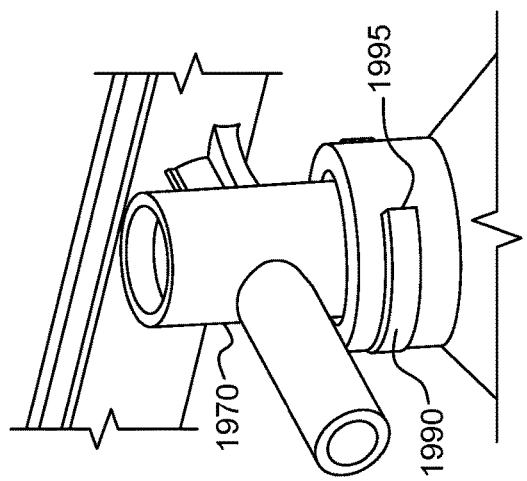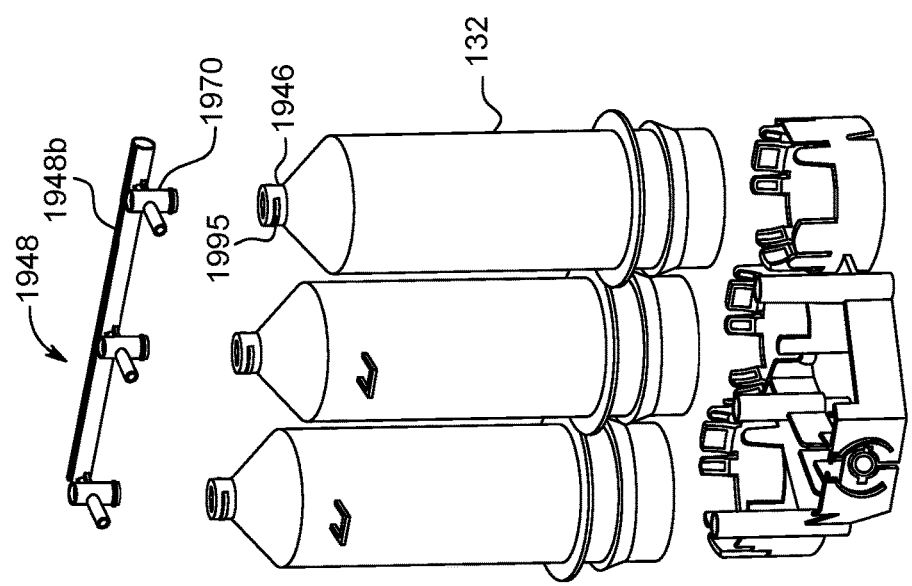
FIG. 19C
FIG. 19D
FIG. 19B
FIG. 19A

MULTIPLE FLUID DELIVERY SYSTEM WITH MULTI-USE DISPOSABLE SET AND FEATURES THEREOF

CROSS REFERENCE TO RELATED APPLICATIONS

The present application is a divisional of U.S. Nonprovisional application Ser. No. 15/541,573, filed Jul. 5, 2017, which is a U.S. national stage filing under 35 U.S.C. § 371 of International Application No. PCT/US2016/012434, filed Jan. 7, 2016, which claims priority to U.S. Provisional Application No. 62/242,090, entitled "Attachment Configurations for Syringe and Manifold," filed Oct. 15, 2015; U.S. Provisional Application No. 62/242,101, entitled "Rotatable Valve for Multiple Use Disposable System," filed Oct. 15, 2015; and U.S. Provisional Application No. 62/101,752, entitled "Multi-Fluid Delivery System and Single-Use Disposable Set Connector Therefor," filed Jan. 9, 2015, the disclosures of each of which are incorporated in their entirety herein by this reference.

BACKGROUND OF THE DISCLOSURE

Field of the Disclosure

This disclosure relates, in general, to the field of multi-fluid delivery systems and single-use disposable set (SUDS) connectors therefor, and, more particularly, to multi-fluid delivery systems having a multi-patient disposable set having a rotatable valve configured for delivering fluid to a patient using a SUDS connector.

Description of the Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these medical fluid delivery systems are designed to deliver a preset amount of fluid at a preset flow rate.

In some injection procedures, a medical practitioner places a catheter or needle into a vein or artery of the patient. The catheter or needle is connected to either a manual or an automatic fluid injector system by way of tubing and a connector that interfaces with the fluid injector system. Automatic fluid injector systems typically include at least one syringe connected to at least one fluid injector having, for example, a powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each. A single-use disposable set (SUDS) connector and associated tubing is connected to the fluid injector system for delivering one or more fluids to the patient.

While various manual and automatic fluid delivery systems are known in the medical field, improved multi-fluid delivery systems adapted for use in medical diagnostic and therapeutic procedures where one or more fluids are supplied to a patient during such procedures continue to be in demand Additionally, improved SUDS connectors that may be used with multi-fluid delivery systems for facilitating a delivery of one or more fluids to a patient are also desired in the medical field. The medical field continues to demand improved medical devices and systems used to supply fluids to patients during various medical procedures.

SUMMARY OF THE DISCLOSURE

In view of the foregoing, a need exists for a medical connector assembly for connecting a single-use portion of a medical assembly to a multi-use portion of the assembly. Further, there is a need for a fluid delivery system for delivery of multiple fluid doses to multiple patients using one or more multi-dose containers. The assembly should be configured to retain sterility of the fluid path through the single-use and multi-use portions of the assembly and, particularly, should maintain sterility of portions of the assembly which are reusable. Furthermore, the system should be arranged to permit automatic priming, defined as removing air from the fluid line, for easier fluid injections.

Therefore, a medical connector configured to address some or all of these needs is provided herein. In accordance with one aspect, a medical connector may include a fluid inlet port configured for removable engagement with a connection port of a multi-use disposable set (MUDS) to establish a fluid connection therewith, and a waste outlet port configured for removable engagement with a waste inlet port of the MUDS to establish a fluid connection therewith. A patient fluid line may be connected, at a first end, to the fluid inlet port and connected, at a second end, to the waste outlet port. Fluid flow through the patient fluid line may be unidirectional from the first end to the second end. The patient fluid line may be configured for being reversibly disconnected from the waste outlet port for delivering a fluid to a patient.

In another aspect, a locking mechanism may be provided for removably securing the medical connector to the MUDS. The fluid inlet port may include a shroud surrounding at least a portion of the fluid inlet port. The fluid inlet port may be shaped to prevent connection with the waste inlet port of the MUDS and wherein the waste outlet port is shaped to prevent connection with the connection port of the MUDS. The second end of the patient fluid line may have a connector configured for removable engagement with the waste outlet port. The medical connector may have a one-way valve configured for unidirectional flow through the fluid inlet port into the patient fluid line. Alternatively, a one-way valve may be located in the patient fluid line. At least one sensing element may be configured for interacting with at least one sensor on the MUDS or on the injector configured for detecting a presence or absence of the at least one sensing element indicating that the medical connector has been properly inserted or installed.

In another aspect, the at least one connection port may be provided on a frame connected to at least one of the plurality of syringes. The at least one connection port may be in fluid communication with the manifold through a delivery line. Each of the plurality of syringes may have a filling line with a spike configured for connection to a bulk fluid source. Each fluid line may be configured for filling the corresponding syringe interior through a filling port on the distal end of the syringe when the at least one valve is in the filling position. The at least one valve may have a slot for engagement with a corresponding blade on a powered injector that is configured to rotate the at least one valve between the filling position and the delivery position. The blade is designed for self-alignment and reversible engagement with the slot in a specific configuration by rotation of the blade relative to the slot until the blade seats into the slot when the blade and slot are in the correct rotational position.

In another aspect, a multi-fluid delivery system may include a powered injector comprising a housing enclosing a plurality of reciprocally operable piston elements. The housing may have a receiving space configured for removably receiving a plurality of syringes of a MUDS. The receiving space may have a bottom plate and a top plate spaced apart from the bottom plate by a rear sidewall such that the plurality of syringes of the MUDS are supported axially between the top plate and the bottom plate. At least one guide may be associated with the receiving space. The at least one guide may narrow in an insertion direction toward the rear sidewall to guide the MUDS into the receiving space.

In another aspect, a plurality of bulk fluid connectors may be configured for connecting the plurality of syringes of the MUDS with at least one bulk fluid source. The top plate may have a plurality of slots configured for receiving the distal end of at least one of the plurality of syringes of the MUDS. Each of the plurality of slots may have a mating recess for receiving a conical distal end of the at least one syringe such that the conical distal end engages the mating recess when the MUDS is received in the receiving space. The top plate may be movable between a first position configured for insertion and removal of the MUDS within the receiving space and a second position configured for locking the MUDS within the receiving space by securing the conical distal end of the at least one syringe in the corresponding mating recess. The top plate may have a latch for locking the top plate in the second position. In another aspect, the top plate may lock in the second position when an access door on the system is closed and optionally locked; and the top plate may move to the first position when the access door on the system is opened. At least one coupling may be configured for engaging at least one valve on at least one of the plurality of syringes of the MUDS. The at least one coupling is a rotatable coupling having a blade configured for self-alignment with a slot formed on the at least one valve on the MUDS.

The MUDS may include at least one syringe having a proximal end and a distal end spaced apart from the proximal end along a longitudinal axis, and a plunger reciprocally movable within a syringe interior between the proximal end and the distal end. The MUDS may further include a manifold in fluid communication with the distal end of the at least one syringe. At least one valve may be in fluid communication with the syringe interior. The at least one valve may be operable between a filling position for filling the syringe interior with fluid and a delivery position for delivering the fluid from the syringe interior. The MUDS may have at least one connection port in fluid communication with the manifold and the syringe interior when the at least one valve is in the delivery position.

In accordance with another aspect, the at least one valve may have a valve head with a slot recessed into the valve head. The slot may be shaped to receive at least a portion of a coupling mechanism for rotating the at least one valve between the filling position and the delivery position when the coupling mechanism engages the slot of the at least one valve. The slot may narrow in a direction from a distal end of the valve to a proximal end of the valve. The at least one valve may be rotatable within a valve receiving cavity at the distal end of the syringe between the filling position and the delivery position. In the filling position, the at least one valve may be operable for filling the syringe interior through a filling port in fluid communication with a bulk fluid source and delivering fluid from the syringe interior through a discharge outlet in fluid communication with the manifold. The at least one connection port may be provided on a frame connected to at least one of the plurality of syringes. The at least one connection port may be in fluid communication with the manifold through a delivery line. The at least one connection port may have a waste port in fluid communication with a waste reservoir. A filling line may have a spike for connection to a bulk fluid source. The fluid line may fill the syringe interior with fluid through the manifold when the at least one valve is in the filling position.

In accordance with another aspect, a multi-fluid injector system may include a powered injector having a housing enclosing at least one reciprocally operable piston element and MUDS having at least one syringe with a proximal end and a distal end spaced apart from the proximal end along a longitudinal axis, and a plunger reciprocally movable by the at least one piston element within a syringe interior between the proximal end and the distal end. A manifold may be in fluid communication with the distal end of the at least one syringe. At least one valve may be in fluid communication with the syringe interior. The at least one valve may be operable between a filling position for filling the syringe interior with fluid and a delivery position for delivering the fluid from the syringe interior. At least one connection port may be in fluid communication with the manifold and the syringe interior when the at least one valve is in the delivery position. A coupling mechanism may be provided for operating the at least one valve between the filling position and the delivery position.

In accordance with another aspect, the coupling mechanism may have a blade and the at least one valve may have a slot shaped to receive the blade of the coupling mechanism. When the blade of the coupling mechanism is received within the slot of the at least one valve, rotation of the coupling mechanism may cause the at least one valve to rotate. The coupling mechanism may self-align with the at least one valve to receive the blade of the coupling mechanism within the slot of the at least one valve. The coupling mechanism may be spring-loaded to maintain contact with the at least one valve as the blade of the coupling mechanism rotates into alignment with the slot of the at least one valve. When the blade of the coupling mechanism is aligned with the slot of the at least one valve, the blade may be urged into the slot under a restoring action of an elastically resilient member. A drive mechanism may be provided for operating the coupling mechanism. The drive mechanism may rotate the coupling mechanism. The blade may have at least one inclined surface that is angled relative to a longitudinal axis of the at least one valve.

In accordance with another aspect, a MUDS may include a plurality of syringes, each syringe having a proximal end and a distal end spaced apart from the proximal end along a longitudinal axis, and a plunger reciprocally movable within a syringe interior between the proximal end and the distal end. A manifold may be connected to the distal end of each of the plurality of syringes. At least one valve may be associated with the manifold. The at least one valve may be operable between a filling position for filling the syringe interior of at least one of the plurality of syringes through the manifold and a delivery position for delivering fluid from the syringe interior of at least one of the plurality of syringes through the manifold. At least one filling line may be in fluid communication with the interior and the syringe interior of at least one of the plurality of syringes when the at least one valve is in the filling position. At least one connection port may be in fluid communication with the manifold and the syringe interior of at least one of the plurality of syringes when the at least one valve is in the delivery position. The at least one valve may have a valve head with a slot recessed into the valve head. The slot may be shaped to receive at least a portion of a coupling mechanism for rotating the at least one valve between the filling position and the delivery position when the coupling mechanism engages the slot of the at least one valve.

In accordance with various other aspects, the MUDS may be characterized in accordance with one or more of the following clauses:

Claus 1. A multi-use disposable set (MUDS) comprising: a plurality of syringes, each syringe having a proximal end and a distal end spaced apart from the proximal end along a longitudinal axis, and a plunger reciprocally movable within a syringe interior between the proximal end and the distal end; a manifold in fluid communication with the distal end of each of the plurality of syringes; at least one valve in fluid communication with the distal end of at least one of the plurality of syringes, the at least one valve operable between a filling position for filling the syringe interior of at least one of the plurality of syringes through the manifold and a delivery position for delivering fluid from the syringe interior of at least one of the plurality of syringes through the manifold; and at least one connection port in fluid communication with the manifold when the at least one valve is in the delivery position.

Clause 2. The MUDS of clause 1, wherein the at least one connection port is provided on a frame connected to at least one of the plurality of syringes.

Clause 3. The MUDS of clause 1 or 2, wherein the at least one connection port is in fluid communication with the manifold through a delivery line.

Clause 4. The MUDS of any of clauses 1-3, further comprising a waste port in fluid connection with a waste reservoir.

Clause 5. The MUDS of any of clauses 1-4, wherein each of the plurality of syringes comprises a filling line with a spike configured for connection to a bulk fluid source, and wherein each fluid line is configured for filling the syringe interior through the manifold when the at least one valve is in the filling position.

Clause 6. The MUDS of any of clauses 1-5, wherein the at least one valve comprises a slot for engagement with a blade that rotates the slot between the filling position and the delivery position.

Clause 7. A multi-fluid injector system, comprising: a powered injector comprising a housing enclosing a plurality of reciprocally operable piston elements; a receiving space configured for removably receiving a plurality of syringes of a multi-use disposable set (MUDS), the receiving space comprising a bottom plate and a top plate spaced apart from the bottom plate by a rear sidewall such that the plurality of syringes of the MUDS are supported axially between the top plate and the bottom plate; and at least one guide associated with the receiving space, wherein the at least one guide narrows in an insertion direction toward the rear sidewall to guide the MUDS into the receiving space.

Clause 8. The multi-fluid injector system of clause 7, further comprising a plurality of bulk fluid connectors configured for connecting the MUDS with at least one bulk fluid source.

Clause 9. The multi-fluid injector system of clause 7 or 8, wherein the top plate defines a plurality of slots configured for receiving at least one of the plurality of syringes of the MUDS, and wherein each of the plurality of slots defines a mating recess for receiving a conical distal end of the at least one syringe such that the conical distal end engages the mating recess when the MUDS is received in the receiving space.

Clause 10. The multi-fluid injector system of any of clauses 7-9, wherein the top plate is movable between a first position configured for insertion and removal of the MUDS within the receiving space and a second position configured for locking the MUDS within the receiving space.

Clause 11. The multi-fluid injector system of clause 10, wherein the top plate comprises a latch for locking the top plate in the second position.

Clause 12. The multi-fluid injector system of any of clauses 7-11, further comprising at least one coupling configured for engaging at least one valve on the MUDS.

Clause 13. The multi-fluid injector system of clause 12, wherein the at least one coupling is a rotatable coupling having a blade configured for self-alignment with a slot formed on the at least one valve on the MUDS.

Clause 14. A MUDS comprising: at least one syringe having a proximal end and a distal end spaced apart from the proximal end along a longitudinal axis, and a plunger reciprocally movable within a syringe interior between the proximal end and the distal end; a manifold in fluid communication with the distal end of the at least one syringe; at least one valve in fluid communication with the syringe interior, the at least one valve operable between a filling position for filling the syringe interior with fluid and a delivery position for delivering the fluid from the syringe interior; and at least one connection port in fluid communication with the manifold and the syringe interior when the at least one valve is in the delivery position.

Clause 15. The MUDS according to clause 14, wherein the at least one valve has a valve head with a slot recessed into the valve head.

Clause 16. The MUDS according to clause 15, wherein the slot is shaped to receive at least a portion of a coupling mechanism for rotating the at least one valve between the filling position and the delivery position when the coupling mechanism engages the slot of the at least one valve.

Clause 17. The MUDS according to clauses 15 or 16, wherein the slot narrows in a direction from a distal end of the valve to a proximal end of the valve.

Clause 18. The MUDS according to any of clauses 14-17, wherein the at least one valve is rotatable within a valve receiving cavity at the distal end of the syringe between the filling position and the delivery position.

Clause 19. The MUDS according to any of clauses 14-18, wherein, in the filling position, the at least one valve is operable for filling the syringe interior through a filling port in fluid communication with a bulk fluid source and delivering fluid from the syringe interior through a discharge outlet in fluid communication with the manifold.

Clause 20. The MUDS according to any of clauses 14-19, wherein the at least one connection port is provided on a frame connected to at least one of the plurality of syringes.

Clause 21. The MUDS according to any of clauses 14-20, wherein the at least one connection port is in fluid communication with the manifold through a delivery line.

Clause 22. The MUDS according to any of clauses 14-21, wherein the at least one connection port has a waste port in fluid communication with a waste reservoir.

Clause 23. The MUDS according to any of clauses 14-22, further comprising a filling line having a spike for connection to a bulk fluid source, wherein the fluid line fills the syringe interior with fluid through the manifold when the at least one valve is in the filling position.

Clause 24. A multi-fluid injector system, comprising: a powered injector comprising a housing enclosing at least one reciprocally operable piston element; a MUDS connectable to the powered fluid injector, the MUDS comprising: at least one syringe having a proximal end and a distal end spaced apart from the proximal end along a longitudinal axis, and a plunger reciprocally movable by the at least one piston element within a syringe interior between the proximal end and the distal end; a manifold in fluid communication with the distal end of the at least one syringe; at least one valve in fluid communication with the syringe interior, the at least one valve operable between a filling position for filling the syringe interior with fluid and a delivery position for delivering the fluid from the syringe interior; and at least one connection port in fluid communication with the manifold and the syringe interior when the at least one valve is in the delivery position; and a coupling mechanism for operating the at least one valve between the filling position and the delivery position.

Clause 25. The multi-fluid injector system according to clause 24, wherein the coupling mechanism comprises a blade and wherein the at least one valve has a slot shaped to receive the blade of the coupling mechanism.

Clause 26. The multi-fluid injector system according to clause 25, wherein, when the blade of the coupling mechanism is received within the slot of the at least one valve, rotation of the coupling mechanism causes the at least one valve to rotate.

Clause 27. The multi-fluid injector system according to clauses 25-26, wherein the coupling mechanism self-aligns with the at least one valve to receive the blade of the coupling mechanism within the slot of the at least one valve.

Clause 28. The multi-fluid injector system according to any of clauses 25-27, wherein the coupling mechanism is spring-loaded to maintain contact with the at least one valve as the blade of the coupling mechanism rotates into alignment with the slot of the at least one valve.

Clause 29. The multi-fluid injector system according to any of clauses 25-28, wherein, when the blade of the coupling mechanism is aligned with the slot of the at least one valve, the blade is urged into the slot under a restoring action of an elastically resilient member.

Clause 30. The multi-fluid injector system according to any of clauses 24-29, further comprising a drive mechanism for operating the coupling mechanism.

Clause 31. The multi-fluid injector system according to any of clauses 24-30, wherein the drive mechanism rotates the coupling mechanism.

Clause 32. The multi-fluid injector system according to any of clauses 25-31, wherein the blade has at least one inclined surface that is angled relative to a longitudinal axis of the at least one valve.

Clause 33. A MUDS comprising: a plurality of syringes, each syringe having a proximal end and a distal end spaced apart from the proximal end along a longitudinal axis, and a plunger reciprocally movable within a syringe interior between the proximal end and the distal end; a manifold connected to the distal end of each of the plurality of syringes; the at least one valve associated with the manifold, the at least one valve operable between a filling position for filling the syringe interior of at least one of the plurality of syringes through the manifold and a delivery position for delivering fluid from the syringe interior of at least one of the plurality of syringes through the manifold; at least one filling line in fluid communication with the interior and the syringe interior of at least one of the plurality of syringes when the at least one valve is in the filling position; and at least one connection port in fluid communication with the manifold and the syringe interior of at least one of the plurality of syringes when the at least one valve is in the delivery position, wherein the at least one valve has a valve head with a slot recessed into the valve head, wherein the slot is shaped to receive at least a portion of a coupling mechanism for rotating the at least one valve between the filling position and the delivery position when the coupling mechanism engages the slot of the at least one valve.

In accordance with various other aspects, the present disclosure provides for attachment configurations between a syringe fluid port of at least one syringe and a conduit syringe attachment end of a manifold conduit of a manifold:

Clause 34. A syringe/manifold configuration comprising at least one syringe having a conical distal end having a syringe fluid port; and a manifold comprising at least one manifold conduit, wherein the manifold conduit is in fluid connection with a main fluid channel and a conduit syringe attachment end, wherein the conduit syringe attachment end is in fluid communication with the syringe fluid port of the at least one syringe, wherein the conduit syringe attachment end of the at least one manifold conduit is in fluid tight connection with the syringe fluid port of the at least one syringe.

Clause 35. The syringe/manifold configuration according to clause 34, wherein the at least one manifold conduit comprises a filling port configured for fluid communication with a MUDS fluid line, a discharge outlet in fluid communication with the main fluid channel, and a valve receiving cavity, wherein the discharge outlet and the filling port are in fluid communication with an interior of the at least one syringe through a valve assembly in a valve receiving cavity.

Clause 36. The syringe/manifold configuration according to clause 35, wherein the valve assembly is operable between a filling position for filling the syringe interior with fluid and a delivery position for delivering the fluid from the syringe interior.

Clause 37. The syringe/manifold configuration according to any of clauses 34 to 36, wherein the conduit syringe attachment end of the at least one manifold conduit is in fluid tight connection with the syringe fluid port by a swivel nut attachment mechanism.

Clause 38. The syringe/manifold configuration according to any of clauses 34 to 36, wherein the conduit syringe attachment end of the at least one manifold conduit comprises an overmolded polymer sheath that forms the fluid tight connection by a solvent bond with an inner surface of the syringe fluid port.

Clause 39. The syringe/manifold configuration according to any of clauses 34 to 36, wherein the syringe fluid port comprises an overmolded polymer sheath that forms the fluid tight connection by a solvent bond with an inner surface of the conduit syringe attachment end of the at least one manifold conduit.

Clause 40. The syringe/manifold configuration according to any of clauses 34 to 36, wherein an inner surface of the syringe fluid port and the inner surface of the conduit syringe attachment end each comprise a locking flange extending radially inward and the valve assembly comprises a syringe locking groove and a manifold locking groove configured to form locking engagements with the locking flanges of the syringe fluid port and the conduit syringe attachment end, respectively.

Clause 41. The syringe/manifold configuration according to any of clauses 34 to 36, wherein an outer circumferential surface of the conduit syringe attachment end is bonded to an inner circumferential surface of the syringe fluid port by a UV activated adhesive, and wherein the syringe fill port comprises a plurality of lateral slots to allow for expansion of the UV activated adhesive during a curing process.

Clause 42 provides: The syringe/manifold configuration according to any of clauses 34 to 36, wherein an outer circumferential surface of the syringe fluid port is bonded to an inner circumferential surface of the conduit syringe attachment end by a UV activated adhesive, and wherein the conduit syringe attachment end comprises a plurality of lateral slots to allow for expansion of the UV activated adhesive during a curing process.

Clause 43. The syringe/manifold configuration according to any of clauses 34 to 36, wherein the conical distal end of the syringe comprises a plurality of distally facing flexible clips configured to engage a radial flange on an outer circumference of the conduit syringe attachment end.

Clause 44. The syringe/manifold configuration according to any of clauses 34 to 36, wherein the syringe fluid port includes a longitudinal slot and the conduit syringe attachment end comprises a radial flange, wherein the conduit syringe attachment end is inserted into the syringe fluid port where the radial flange is immediately proximal to the longitudinal slot, and wherein connection between the conduit syringe attachment end and the syringe fluid port is maintained by a C-clip inserted into the longitudinal slot.

Clause 45. The syringe/manifold configuration according to any of clauses 34 to 36, wherein one of the syringe fluid port and the conduit syringe attachment end comprises a radial flange and the other of the syringe fluid port and the conduit syringe attachment end comprises a complementary radial receiving flange that receives the radial flange, and wherein the radial flange and the complementary radial receiving flange are connected by a laser weld.

Clause 46. The syringe/manifold configuration according to any of clauses 34 to 36, wherein one of the syringe fluid port and the conduit syringe attachment end comprises a circumferential receiving slot including an energy director and the other of the syringe fluid port and the conduit syringe attachment end comprises a terminal portion that engages and is received in the circumferential receiving slot, and wherein the terminal portion and the circumferential receiving slot are connected by an ultrasonic weld.

Clause 47. The syringe/manifold configuration according to any of clauses 34 to 36, wherein the syringe fluid port comprises a female luer connector which forms the fluid tight connection with a male luer connection on the conduit syringe attachment end, wherein the syringe fluid port further comprises a distal circumferential slot between the syringe fluid port and the conduit syringe attachment end configured for receiving a UV activated adhesive.

Clause 48. The syringe/manifold configuration according to any of clauses 34 to 36, wherein engagement between the syringe fluid port and the conduit syringe attachment end defines a tubular space between an inner surface of the syringe fluid port and an outer surface of the conduit syringe attachment end, wherein the tubular space is configured for receiving a UV activated adhesive.

Clause 49. The syringe/manifold configuration according to any of clauses 34 to 36, wherein engagement between the syringe fluid port and the conduit syringe attachment end defines a tubular space between an inner surface of the conduit syringe attachment end and an outer surface of the syringe fluid port, wherein the tubular space is configured for receiving a UV activated adhesive.

Clause 50. The syringe/manifold configuration according to any of clauses 34 to 36, wherein the syringe fluid port comprises a female luer connector which forms the fluid tight connection with a male luer connection on the conduit syringe attachment end, wherein the syringe fluid port is welded to the conduit syringe attachment end by a laser tack weld.

These and other features and characteristics of multi-fluid delivery systems and SUDS connectors therefor, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limits of the disclosure. As used in the specification and the claims, the singular form of "a", "an", and "the" include plural referents unless the context clearly dictates otherwise.

BRIEF DESCRIPTION OF THE DRAWINGS

FIGS. 13A-C illustrate aspects of a syringe/manifold connection configuration;

FIGS. 17A-C illustrate an aspect of a syringe/manifold connection configuration;

FIGS. 18A-C illustrate an aspect of a syringe/manifold connection configuration;

FIGS. 19A-D illustrate an aspect of a syringe/manifold connection configuration;

DETAILED DESCRIPTION

Figure 1A:
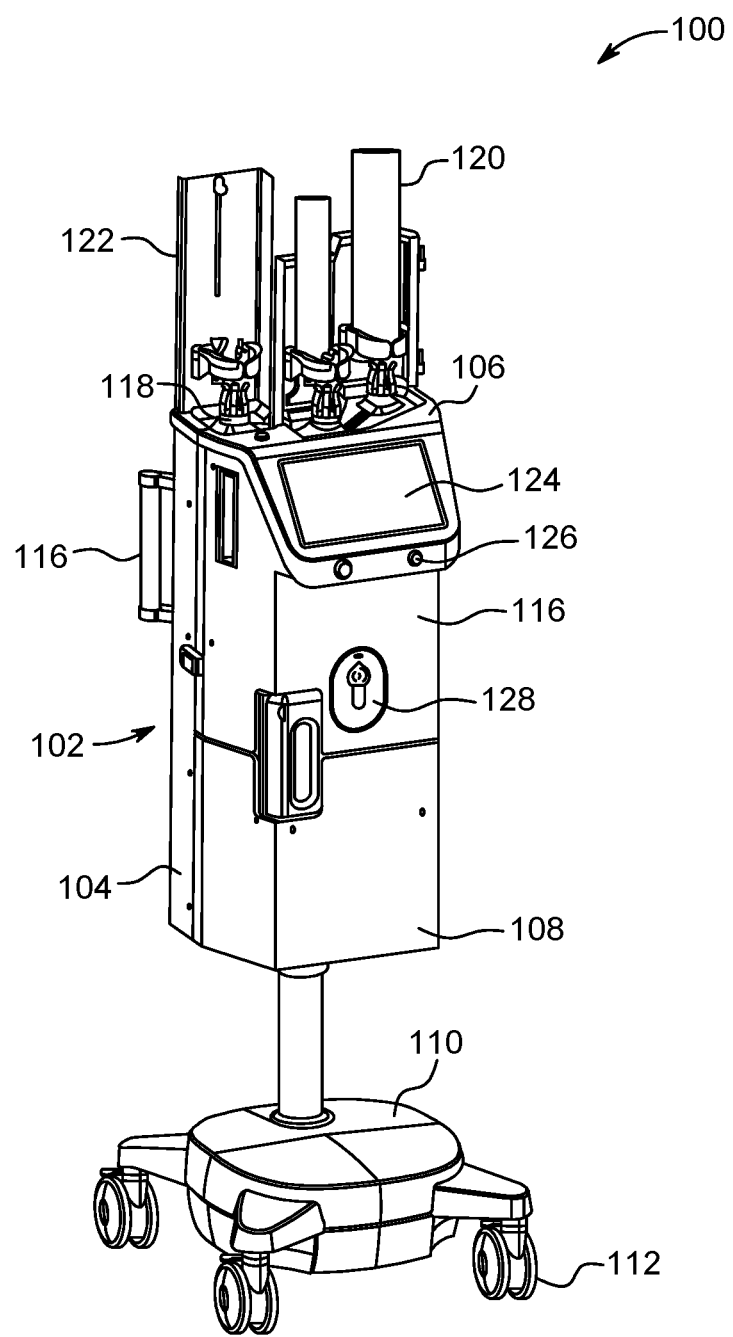
FIG. 1A is a perspective view of a multi-fluid delivery system, according to one aspect of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a MUDS, the term "proximal" refers to a portion of a syringe nearest a piston element for delivering fluid from a syringe. When used in relation to a SUDS connector, the term "proximal" refers to a portion of a SUDS connector nearest to a multi-fluid injector system when a SUDS connector is oriented for connecting with a multi-fluid injector system. When used in relation to a syringe of a MUDS, the term "distal" refers to a portion of a syringe nearest to a delivery nozzle. When used in relation to a SUDS connector, the term "distal" refers to a portion of a SUDS connector nearest to a user when a SUDS connector is oriented for connecting with a multi-fluid injector system. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

Referring to the drawings in which like reference characters refer to like parts throughout the several views thereof, the present disclosure is generally directed to a multi-fluid medical injector/injection system 100 (hereinafter "fluid injector system 100") having a MUDS 130 (shown in FIG. 1B) configured for delivering fluid to a patient using a SUDS 190 (shown in FIG. 8A). The fluid injector system 100 includes multiple components as individually described herein. Generally, the fluid injector system 100 has a powered injector administrator or device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein.

With reference to FIG. 1A, the fluid injector system 100 includes an injector housing 102 having opposed lateral sides 104, a distal or upper end 106, and a proximal or lower end 108. In some aspects, the housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other aspects, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements 103 (shown in FIG. 2) associated with the fluid injector system 100 described herein. Such piston elements 103 may be reciprocally operable via electro-mechanical drive components such as a ball screw shaft driven by a motor, a voice coil actuator, a rack-and-pinion gear drive, a linear motor, and the like. In some aspects, at least some of the mechanical drive components, electrical and power components, and control components may be provided on the base 110.

Figure 1B:
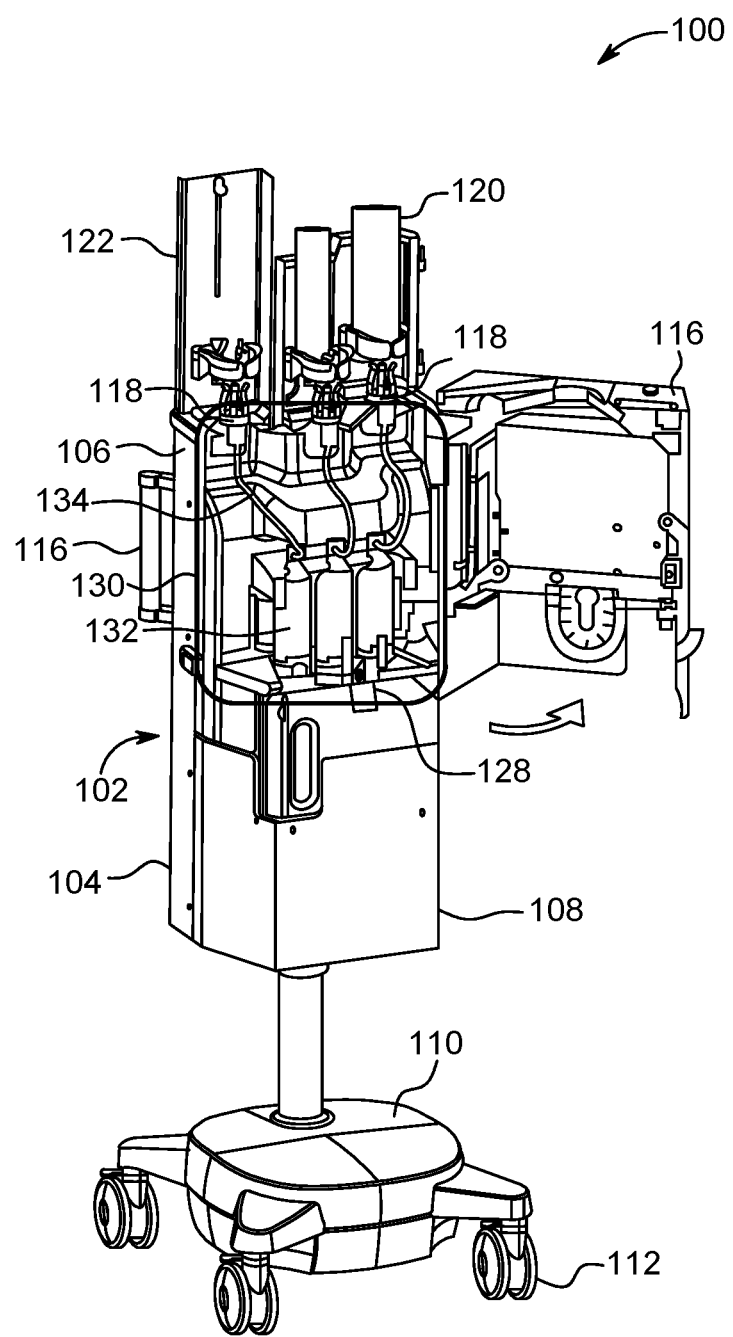
FIG. 1B is a perspective view of the multi-fluid delivery system of FIG. 1A with an access panel in an open position.

With reference to FIG. 1B, and with continued reference to FIG. 1A, the fluid injector system 100 has at least one door 116 that encloses at least some of the mechanical drive components, electrical and power components, and control components. The door 116 is desirably movable between an open position (shown in FIG. 1B) and a closed position (shown in FIG. 1A). In some aspects, the door 116 may be lockable.

The fluid injector system 100 further includes at least one bulk fluid connector 118 for connection with at least one bulk fluid source 120. In some aspects, a plurality of bulk fluid connectors 118 may be provided. For example, as shown in FIGS. 1A and 1B, three bulk fluid connectors 118 may be provided in a side-by-side or other arrangement. In some aspects, the at least one bulk fluid connector 118 may be a spike configured for removably connecting to the at least one bulk fluid source 120, such as a vial, a bottle, or a bag. The at least one bulk fluid connector 118 may have a reusable or non-reusable interface with each new bulk fluid source 120. The at least one bulk fluid connector 118 may be formed on the multi-patient disposable set, as described herein. The at least one bulk fluid source 120 may be configured for receiving a medical fluid, such as saline, contrast solution, or other medical fluid, for delivery to the fluid injector system 100. The housing 102 may have at least one support member 122 for supporting the at least one bulk fluid source 120 once it is connected to the fluid injector system 100.

With reference to FIG. 1A, the fluid injector system 100 includes one or more user interfaces 124, such as a graphical user interface (GUI) display window. The user interface 124 may display information pertinent to a fluid injection procedure involving fluid injector system 100, such as current flow rate, fluid pressure, and volume remaining in the at least one bulk fluid source 120 connected to the fluid injector system 100 and may be a touch screen GUI that allows an operator to input commands and/or data for operation of fluid injector system 100. While the user interface 124 is shown on the injector housing 102, such user interface 124 may also be in the form of a remote display that is wired or wirelessly linked to the housing 102 and control and mechanical elements of fluid injector system 100. In some aspects, the user interface 124 may be a tablet computer that is detachably connected to the housing 102 and is in wired or wirelessly linked communication with the housing 102. Additionally, the fluid injector system 100 and/or user interface 124 may include at least one control button 126 for tactile operation by an attendant operator of the fluid injector system 100. In certain aspects, the at least one control button may be part of a keyboard for inputting commands and/or data by the operator. The at least one control button 126 may be hard-wired or wirelessly connected to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) acknowledging that a multi-patient disposable set has been loaded or unloaded; (2) locking/unlocking of the multi-patient disposable set; (3) filling/purging of the fluid injector system 100; (4) inputting information and/or data related to the patient and/or injection procedure, and (5) initiating/stopping an injection procedure. The user interface 124 and/or any electronic processing units associated with the fluid injector system 100 may be wired or wirelessly connected to an operation and/or data storage system such as a hospital network system.

With reference to FIG. 1B, the fluid injector system includes a MUDS 130 that is removably connected to the fluid injector system 100 for delivering one or more fluids from the one or more bulk fluid sources 120 to the patient. The fluid injector system 100 includes at least one slot or access port 128 for releasably connecting a SUDS to the MUDS 130, as described herein. The MUDS 130 may include one or more syringes or pumps 132. In some aspects, the number of syringes 132 may correspond to the number of bulk fluid sources 120. For example, with reference to FIG. 1B, the MUDS 130 has three syringes 132 in a side-by-side arrangement such that each syringe 132 is fluidly connectable to one of the bulk fluid sources 120. Each syringe 132 may be fluidly connectable to one of the bulk fluid sources 120 by a corresponding bulk fluid connector 118 and an associated MUDS fluid path 134. The MUDS fluid path 134 may be formed as a flexible tube with a spike element at its terminal end that connects to the bulk fluid connector 118. In some aspects, the bulk fluid connector 118 may be provided directly on the MUDS 130.

Figure 2:
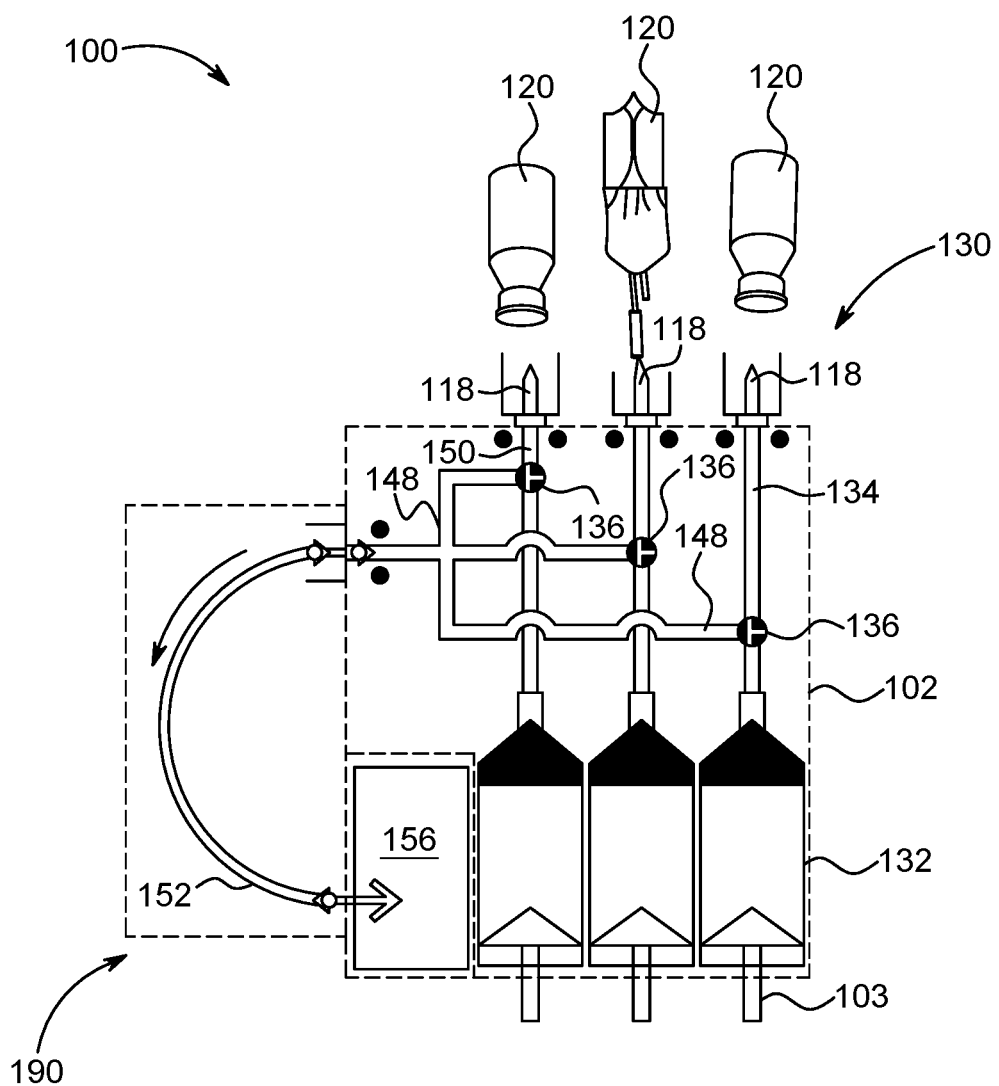
FIG. 2 is schematic view of various fluid paths within the multi-fluid delivery system of FIG. 1A.
Figure 3A:
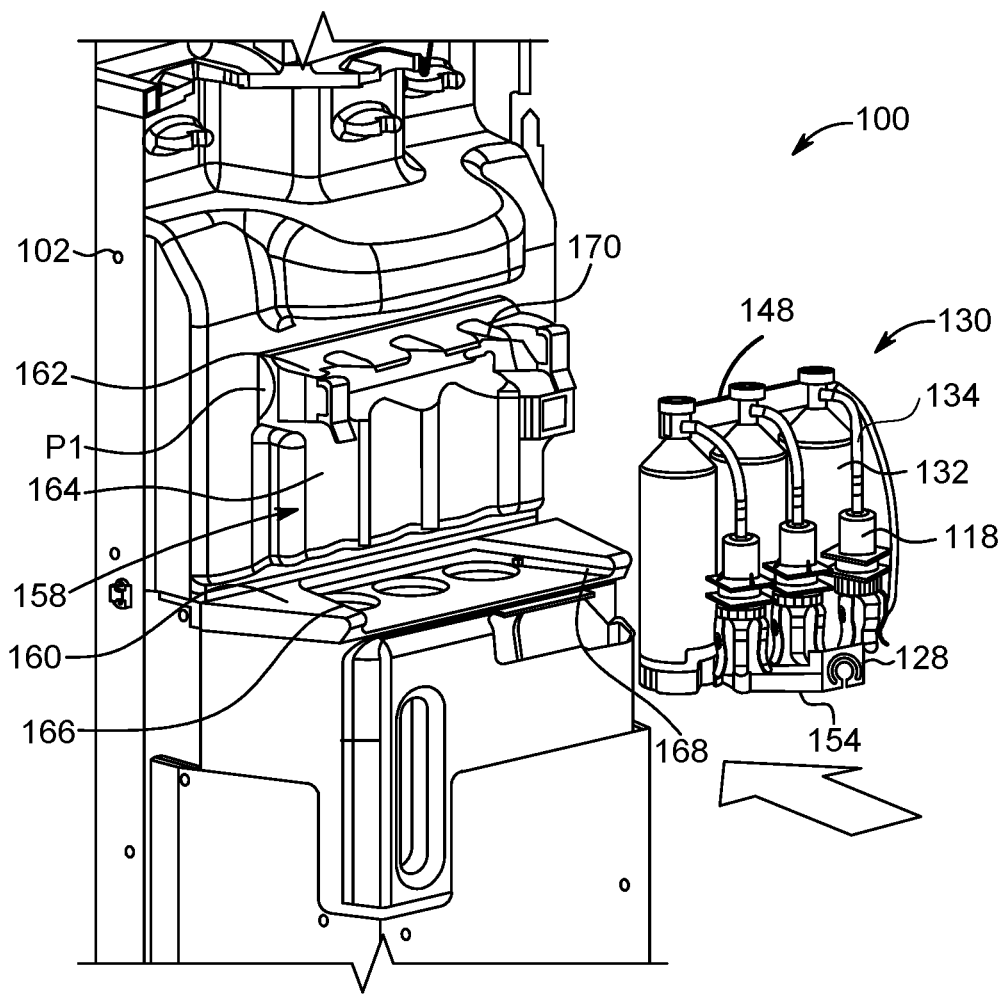
FIG. 3A is a perspective view of a MUDS as it is being inserted into a receiving slot on a multi-fluid delivery system.
Figure 3B:
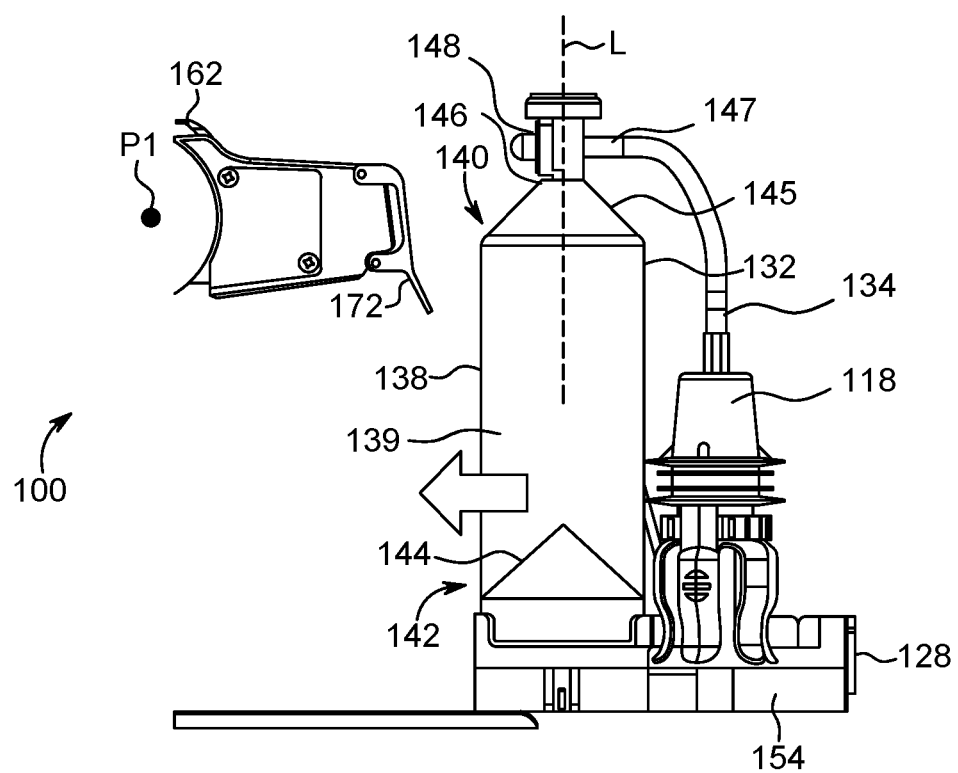
FIG. 3B is a side view of the MUDS of FIG. 3A.

With reference to FIGS. 2-3A, the MUDS 130 is removably connectable to the housing 102 of the fluid injector system 100. The MUDS 130 may include a frame 154 for supporting the one or more syringes 132. The syringes 132 may be removably or non-removably connected to the frame 154. In certain aspects, the at least one syringe 132 may be co-molded with the frame 154 or alternatively, adhered or welded to frame 154. With reference to FIG. 3B, each syringe 132 has an elongated, substantially cylindrical syringe body 138 having a front or distal end 140 and a rear or proximal end 142. A syringe plunger 144 is disposed within the syringe body 138 and is reciprocally movable within the syringe body 138 due to movement of a piston element associated with the fluid injector system 100. The distal end 140 of the syringe body 138 is generally conical-shaped and tapers to an apex or cone point 145 which is adapted to interface with a corresponding apex curve formed in the recess defined in the fluid injector system 100, as described herein. The syringe apex or cone point 145 is located along a central longitudinal axis L of the syringe body 138.

With continued reference to FIG. 3B, each syringe 132 may have a filling port 147 in fluid communication with the MUDS fluid path 134 for filling a syringe interior 139 with fluid from a bulk fluid source 120 (shown in FIG. 2). Each syringe 132 may further have discharge outlet or conduit 146 at the terminal end of the apex or cone point 145. The discharge outlet 146 of each syringe 132 is in fluid communication with a manifold 148. In some aspects, the manifold 148 may fluidly connect a plurality of syringes 132. In certain aspects, the manifold 148 may also provide support for the syringes 132 such that the syringes 132 can be handled as a single, unitary structure. In some aspects, the manifold 148 supports the distal end 140 of each syringe 132 while the frame 154 supports the proximal end 142 of each syringe 132. In some aspects, the at least a portion of the manifold 148 may be monolithically formed with at least one syringe 132. In other aspects, the manifold 148 may be formed separately from the plurality of syringes 132 and include a plurality of conduits 148a corresponding to each of the plurality of syringes 132, wherein the individual conduits 148a may be attached or adhered to the individual outlet ports 146 of each of the plurality of syringes 132, for example by an appropriate adhesive or welding. The syringes 132 may be arranged in a side-by-side orientation, or any other orientation that retains the relative positioning of the syringes 132.

Figure 10A:
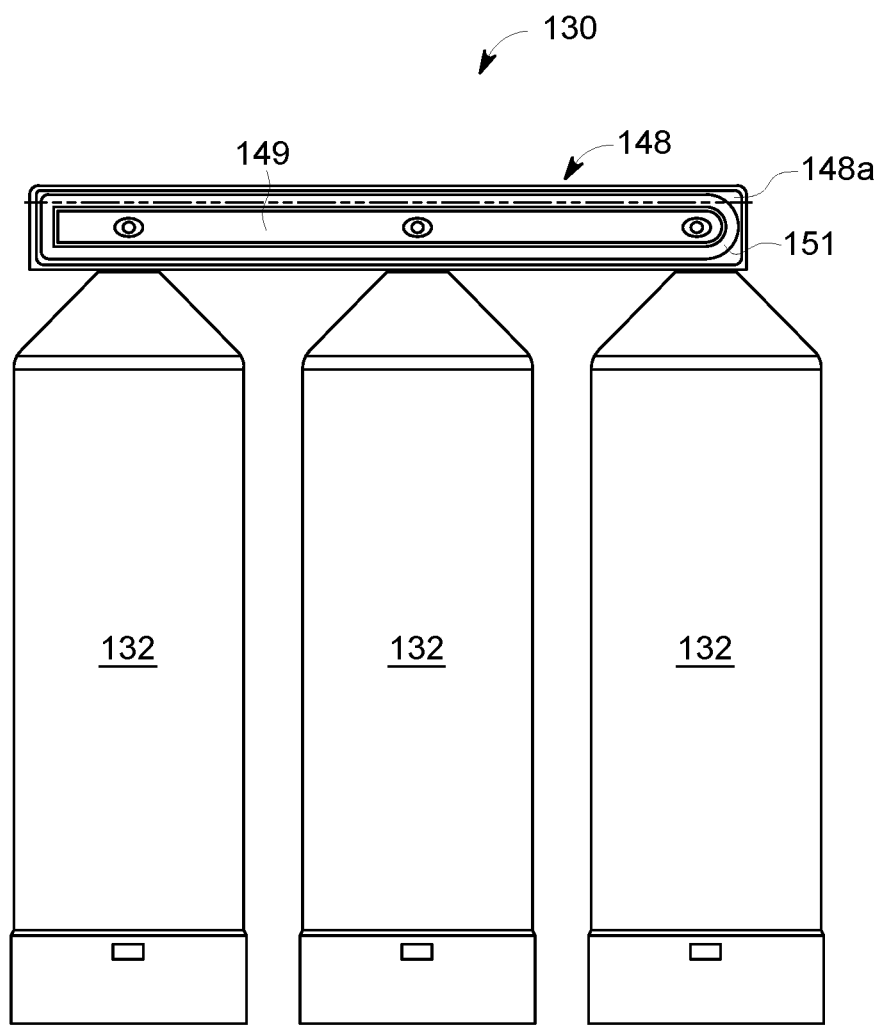
FIG. 10A is a side view of a MUDS in accordance with another aspect of the present disclosure.
Figure 10B:
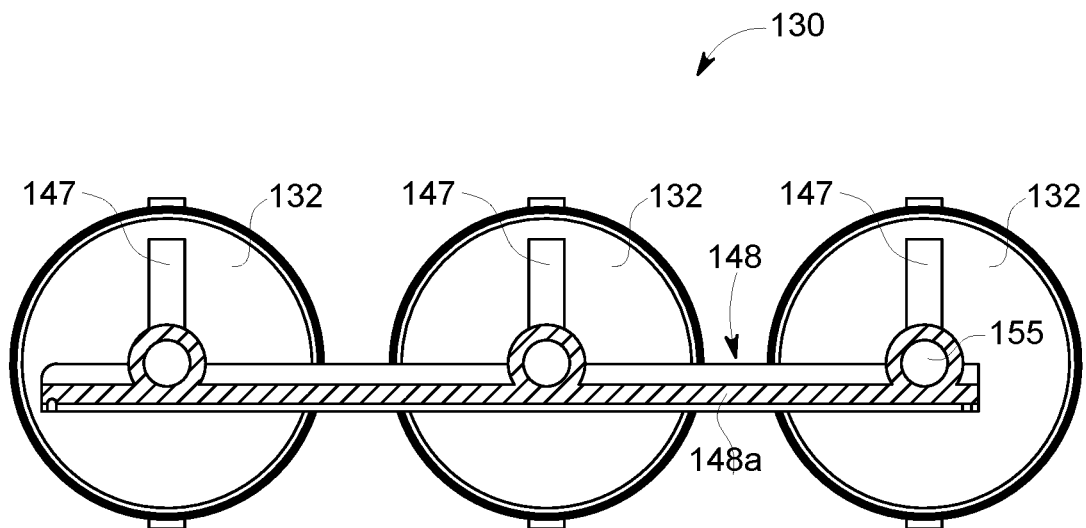
FIG. 10B is a top view of the MUDS shown in FIG. 10A.
Figure 10C:
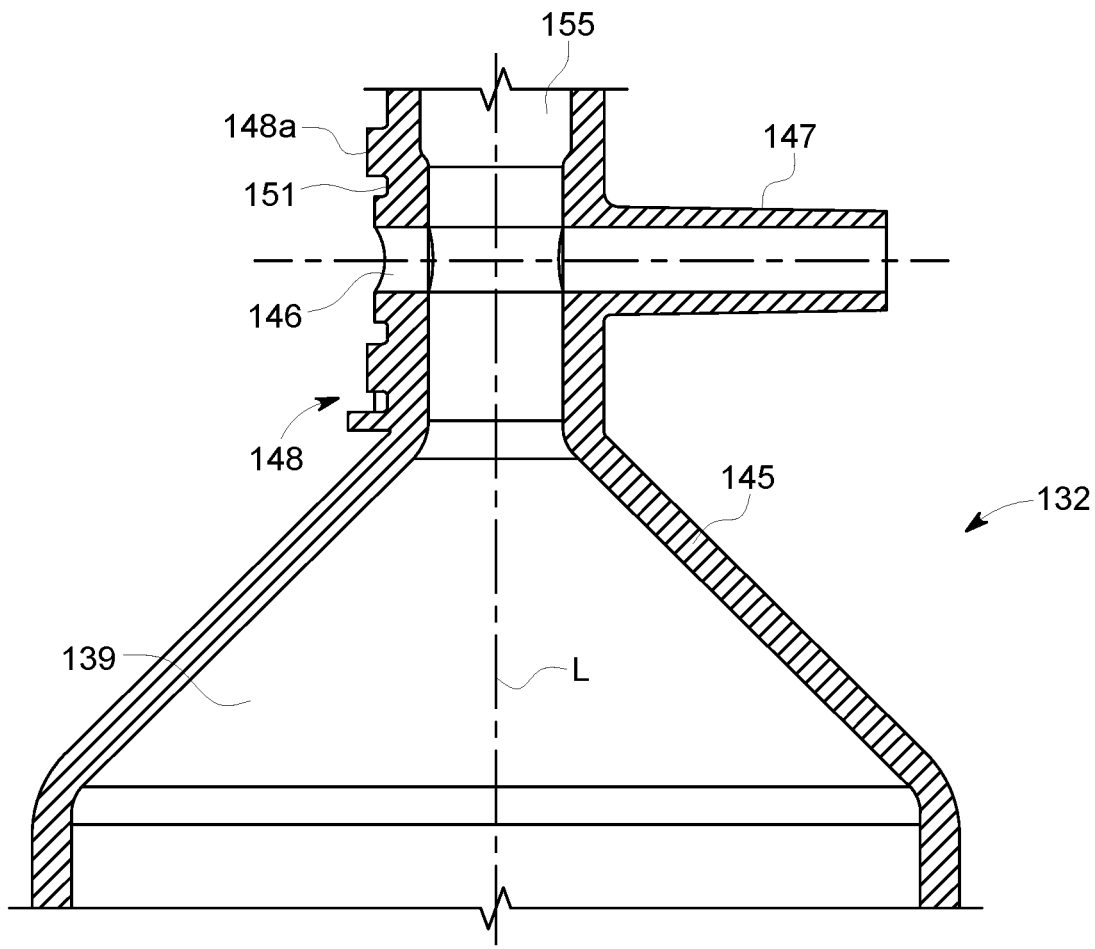
FIG. 10C is a cross-sectional side view of a syringe for use with the MUDS shown in FIG. 10A.

With reference to FIGS. 10A-10C, the MUDS 130 is illustrated in accordance with another aspect. The MUDS 130 may include a plurality of syringes 132 in a side-by-side, or other arrangement, with each syringe 132 being fluidly connectable to one of the bulk fluid sources 120 (shown in FIG. 2). Each syringe 132 may be in fluid communication with the manifold 148. The manifold 148 may include a plate-like structure that extends between the discharge outlets 146 of the syringes 132 such that the manifold 148 monolithically connects the syringes 132. The manifold 148 may have a fluid pathway 149 that is in fluid communication with each syringe 132. The fluid pathway 149 may be in fluid communication with one or more fluid outlet lines 152 (shown in FIG. 2). A first portion 148a of the manifold 148 may be monolithically formed with each syringe 132, such as by molding, adhesive means, or welding, while a second portion 148b (shown in FIG. 11) may be permanently or non-permanently connected to the first portion 148a. In some aspects, the first portion 148a of the manifold 148 may be connected to the second portion 148b by welding, adhesive, one or more fasteners, or any other connection means. The combination of the first portion 148a and the second portion 148b may create a fluid path within the manifold that fluidly connects the discharge ports 146 of each of the plurality of syringes 132 and the one or more fluid outlet lines 152. At least one of the first portion 148a and the second portion 148b may have a channel 151 extending around a circumference of the manifold 148 surrounding the discharge outlets 146. The channel 151 may be configured for receiving a gasket 153 (shown in FIG. 11) for sealing the interface between the first portion 148a and the second portion 148b. With reference to FIGS. 10B-10C, a valve receiving cavity 155 may be provided at the terminal end of the apex or cone point 145 of each syringe 132. The valve receiving cavity 155 may extend into the syringe interior 139 in a direction aligned with a longitudinal axis L of each syringe 132 (shown in FIG. 10C). In some aspects, the valve receiving cavity 155 is in fluid communication with the syringe interior 139, the filling port 147 and the discharge outlet 146. The valve receiving cavity 155 is configured for receiving a valve 136 (shown in FIG. 11). As described herein, at least a portion of the valve 136 may be rotatable about the longitudinal axis L and within the valve receiving cavity 155. The valve 136 may be operable between a filling position for filling the syringe interior 139 with fluid and a delivery position for delivering the fluid from the syringe interior 139. In some aspects, the valve 136 may be rotatable between a first position, where the filling port 147 is in fluid communication with the syringe interior 139 while the discharge outlet 146 is in fluid isolation from the syringe interior 139, and a second position, where the discharge outlet 146 is in fluid communication with the syringe interior 139 while the filling port 147 is in fluid isolation from the syringe interior 139. The valve 136 may have a third position where the interior of the syringe 139 is isolated from both the filling port 147 and the discharge outlet 146. In the first position, the valve 136 may be configured for filling the syringe interior 139 with fluid from a bulk fluid source 120 through the MUDS fluid path 134 while preventing fluid from being delivered to the manifold 148. In the second position, the valve 136 may be configured for delivering fluid from the syringe interior 139 to the manifold 148 through the discharge outlet 146 while preventing fluid from being delivered through the filling port 147. The valve 136 may also be configured for preventing fluid flow through the filling port 147 and the discharge outlet 146 such that fluid cannot be delivered into or from the syringe interior 139. In some aspects, the valve 136 may be rotatable to partially open or partially closed the discharge outlet 146 and/or the filling port 147. In various aspects, the valves 136 on each syringe 132 may be controlled independently of each other, for example, such that various medical fluids can be delivered into one or more syringes 132 and/or, simultaneously or sequentially, be delivered out of one or more other syringes 132. The valves 136 of the plurality of syringes 132 may be controlled, for example, through the electronic control device(s) associated with the fluid injector system 100

Figure 10D:
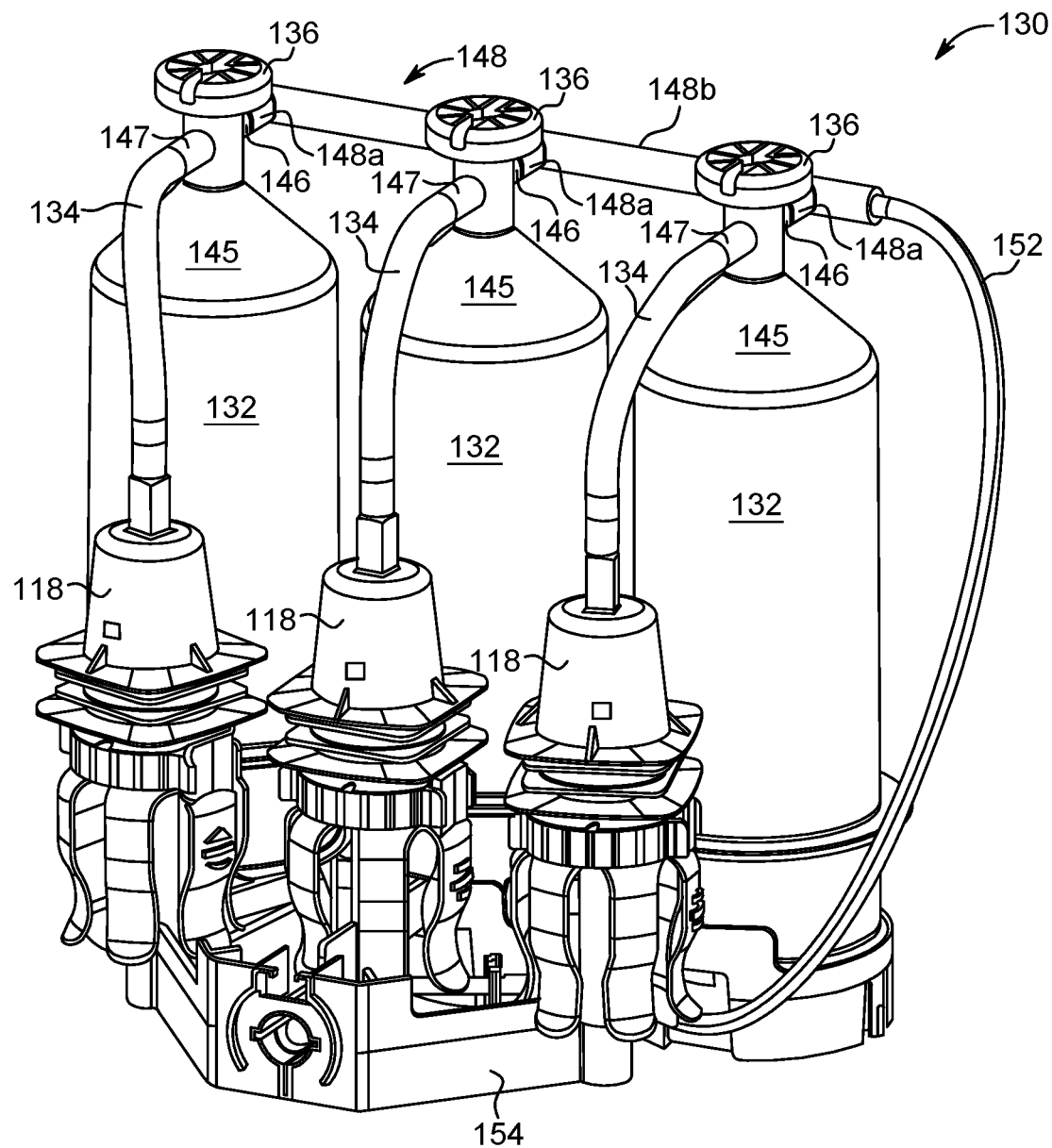
FIG. 10D is a side perspective view of a MUDS in accordance with another aspect of the present disclosure.

With reference to FIG. 10D, the MUDS 130 is illustrated in accordance with another aspect. The MUDS 130 may include a plurality of syringes 132 in a side-by-side, or other arrangement, with each syringe 132 being fluidly connectable to one of the bulk fluid sources 120 (shown in FIG. 2). The MUDS 130 may include a frame 154 for supporting the one or more syringes 132. The syringes 132 may be removably or non-removably connected to the frame 154. In some aspects, each syringe may be fluidly connectable to one of the bulk fluid sources 120 by way of the bulk fluid connector 118 and the MUDS fluid path 134. The apex or cone point 145 of each syringe 132 may have a discharge outlet 146, a filling port 147, and a valve receiving cavity 155. The valve receiving cavity 155 may extend into the syringe interior in a direction substantially parallel with a longitudinal axis L of each syringe 132 (see e.g., FIG. 11). The discharge outlet 146 and the filling port 147 may extend toward the syringe interior in a direction substantially perpendicular to the longitudinal axis L of each syringe 132. The discharge outlet 146 and the filling port 147 may be arranged opposite to one another around an outer circumference of the apex or cone point 145. In some aspects, the valve receiving cavity 155 is in fluid communication with the syringe interior, the filling port 147 and the discharge outlet 146.

With continued reference to FIG. 10D, the discharge outlet 146 of each syringe 132 may be connected to a manifold 148. Each syringe 132 may be formed separately and be independently connectable to the manifold 148. The manifold 148 may be a tubular structure having a one or more conduits 148a for connecting to the discharge outlets 146 of the syringes 132. In some aspects, the conduits 148a may be removably or non-removably connected to the discharge outlets 146. For example, each conduit 148a may be adhesively connected, laser or ultrasonic vibration welded, or permanently and non-removably fastened by one or more mechanical fasteners to the respective discharge outlet 146. Alternatively, each conduit 148a may be removably connected to the respective discharge outlet 146, such as, for example, an interference fit, one or more clips, or other mechanical connection means. The manifold 148 may have a main fluid channel 148b that is in fluid communication with each syringe 132 through the respective conduit 148a. In some aspects, the one or more conduits 148a are monolithically formed with the main fluid channel 148b. One end of the main fluid channel 148b may be in fluid communication with one or more fluid outlet lines 152 to deliver fluid from the syringes 132 to the patient, as described herein.

The valve receiving cavity 155 is configured for receiving the valve 136. As described herein, at least a portion of the valve 136 may be rotatable about the longitudinal axis L and within the valve receiving cavity 155. The valve 136 may be operable between a filling position for filling the syringe interior with fluid and a delivery position for delivering the fluid from the syringe interior. In some aspects, the valve 136 may be rotatable between a first position, where the filling port 147 is in fluid communication with the syringe interior while the discharge outlet 146 is in fluid isolation from the syringe interior, and a second position, where the discharge outlet 146 is in fluid communication with the syringe interior while the filling port 147 is in fluid isolation from the syringe interior. In the first position, the valve 136 may be configured for filling the syringe interior with fluid from a bulk fluid source 120 through the MUDS fluid path 134 while preventing fluid from being delivered to the manifold 148. In the second position, the valve 136 may be configured for delivering fluid from the syringe interior to the manifold 148 through the discharge outlet 146 while preventing fluid from being delivered through the filling port 147. The valve 136 may also be configured for preventing fluid flow through the filling port 147 and the discharge outlet 146 such that fluid cannot be delivered into or from the syringe interior. In some aspects, the valve 136 may be rotatable to partially open or partially close the discharge outlet 146 and/or the filling port 147. In various aspects, the valves 136 on each syringe 132 may be controlled independently of each other such that fluid can be delivered into one or more syringes 132 while, simultaneously or sequentially, being delivered out of one or more other syringes 132.

With further reference to FIG. 2, the MUDS 130 is removably connectable to the housing 102 of the fluid injector system 100. As will be appreciated by one having ordinary skill in the art, it may be desirable to construct at least a portion of the MUDS 130 from a clear medical grade plastic in order to facilitate visual verification that a fluid connection has been established with the fluid injector system 100. Visual verification is also desirable for confirming that no air bubbles are present within various fluid connections. Alternatively, at least a portion of the MUDS 130 and/or door 116 may include windows (not shown) for visualization of the connection between various components. Various optical sensors (not shown) may also be provided to detect and verify the connections. Additionally, various lighting elements (not shown), such as light emitting diodes (LEDs), may be provided to actuate one or more optical sensors and indicate that a suitable connection has been established between the various components.

With continued reference to FIG. 2, a schematic view of various fluid paths of the fluid injector system 100 is provided. The MUDS 130 may include one or more valves 136, such as stopcock valves, for controlling which medical fluid or combinations of medical fluids are withdrawn from the multi-dose bulk fluid source 120 and/or are delivered to a patient through each syringe 132. In some aspects, the one or more valves 136 may be provided on the distal end 140 of the plurality of syringes 132 or on the manifold 148. The manifold 148 may be in fluid communication via valves 136 and/or syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the one or more syringes 132, or it may be delivered from the one or more syringes 132. In a first position, such as during the filling of the syringes 132, the one or more valves 136 are oriented such that fluid flows from the bulk fluid source 120 into the desired syringe 132 through the MUDS fluid path 134. During the filling procedure, the one or more valves 136 are positioned such that fluid flow through one or more fluid outlet lines 152 or manifold 148 is blocked. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through the MUDS fluid path 134 is blocked. The one or more valves 136, the MUDS fluid path 134, and/or fluid outlet lines 152 may be integrated into the manifold 148. The one or more valves 136 may be selectively positioned to the first or second position by manual or automatic handling. For example, the operator may position the one or more valves 136 into the desired position for filling or fluid delivery. In other aspects, at least a portion of the fluid injector system 100 is operable for automatically positioning the one or more valves 136 into a desired position for filling or fluid delivery based on input by the operator, as described herein. Suitable examples of valve body structures are shown in International Application No. PCT/US2012/056355 and U.S. Application Publication No. 2014/0228762, each filed Sep. 20, 2012, the disclosures of which are incorporated by this reference.

With specific reference to FIG. 3B, the MUDS 130 further includes a frame 154 receiving at least a portion of the proximal end 142 of the at least one syringe 132. In some aspects, the frame 154 may be shaped to receive at least a portion of the proximal end 142 of each syringe 132. In some aspects, the fluid outlet line 152 may be connected to the frame 154. The frame 154, in some aspects, defines at least a portion of a connection port 192 for connecting a SUDS to the MUDS 130. The frame 154 may have a handle for grasping the MUDS 130 during insertion into and removal from the fluid injector system 100. In certain aspects, the connection port 192, may be formed as part of or adhered/welded to the frame 154 to form a single MUDS unit.

With reference to FIG. 2, in some aspects, the fluid outlet line 152 may also be connected to a waste reservoir 156 on the fluid injector system 100. The waste reservoir 156 is desirably separate from the syringes 132 to prevent contamination. In some aspects, the waste reservoir 156 is configured to receive waste fluid expelled from the syringes 132 during, for example, a priming operation. The waste reservoir 156 may be removable from the housing 102 in order to dispose of the contents of the waste reservoir 156. In other aspects, the waste reservoir 156 may have a draining port (not shown) for emptying the contents of the waste reservoir 156 without removing the waste reservoir 156 from the housing 102. In some aspects, the waste reservoir 156 is provided as a separate component from the MUDS 130.

With the foregoing description of the fluid injector system 100 and the MUDS 130 in mind, exemplary loading and unloading of MUDS 130 into a receiving space 158 (shown in FIG. 3A) on the housing 102 will now be described with reference to FIGS. 3A-5B. In the following discussion, it is assumed that the MUDS 130 may be connected to and removed from connection with the fluid injector system 100 for use with a single or multiple patients. Referring initially to FIG. 3A, the receiving space 158 has a bottom plate 160 separated from a top plate 162 by a rear sidewall 164. The bottom plate 160 has a plurality of openings 166 through which the piston elements 103 of the fluid injector system 100 extend to engage the respective plungers 144 of the MUDS 130. At least one bottom guide 168 is formed on the bottom plate 160 for guiding the frame 154 of the MUDS 130 as the MUDS 130 is loaded into the fluid injector system 100. In some aspects, the bottom guide 168 may be configured as a pair of walls raised relative to the bottom plate 160 and narrowing in an insertion direction toward the rear sidewall 164. During insertion, the bottom guide 168 defines a guiding surface that locates the frame 154 of the MUDS 130 and guides the frame 154 toward the rear sidewall 164 of the receiving space 158. In this manner, the MUDS 130 can be aligned into the receiving space 158 even when MUDS 130 is initially misaligned with the receiving space 158.

With reference to FIG. 3B, and with continued reference to FIG. 3A, the top plate 162 is configured to receive the distal end 140 of the at least one syringe 132. The top plate 162 has one or more syringe slots 170 (shown in FIG. 3A) that are shaped to receive at least a portion of the distal end 140 of the syringes 132. In some aspects, when the MUDS 130 is inserted into the receiving space 158, the syringe slots 170 of the top plate 162 may be disposed between the distal end 140 of the at least one syringe 132 and the manifold 148. The top plate 162 may be rotatable about a pivot point P1, shown in FIG. 3B, or it may be movable in a vertical direction relative to the MUDS 130. In a first position, such as during loading of the MUDS 130 into the receiving space 158, the top plate 162 may be raised such that the apex or cone point 145 of the at least one syringe 132 clears a lower surface of the top plate 162. In some aspects, the top plate 162 can default to the first position each time the MUDS 130 is removed from the receiving space 158, such as by a biasing mechanism. In other aspects, the top plate 162 can be urged to the first position as the apex or cone point 145 of the at least one syringe 132 engages the at least one syringe slot 170.

Figure 4A:
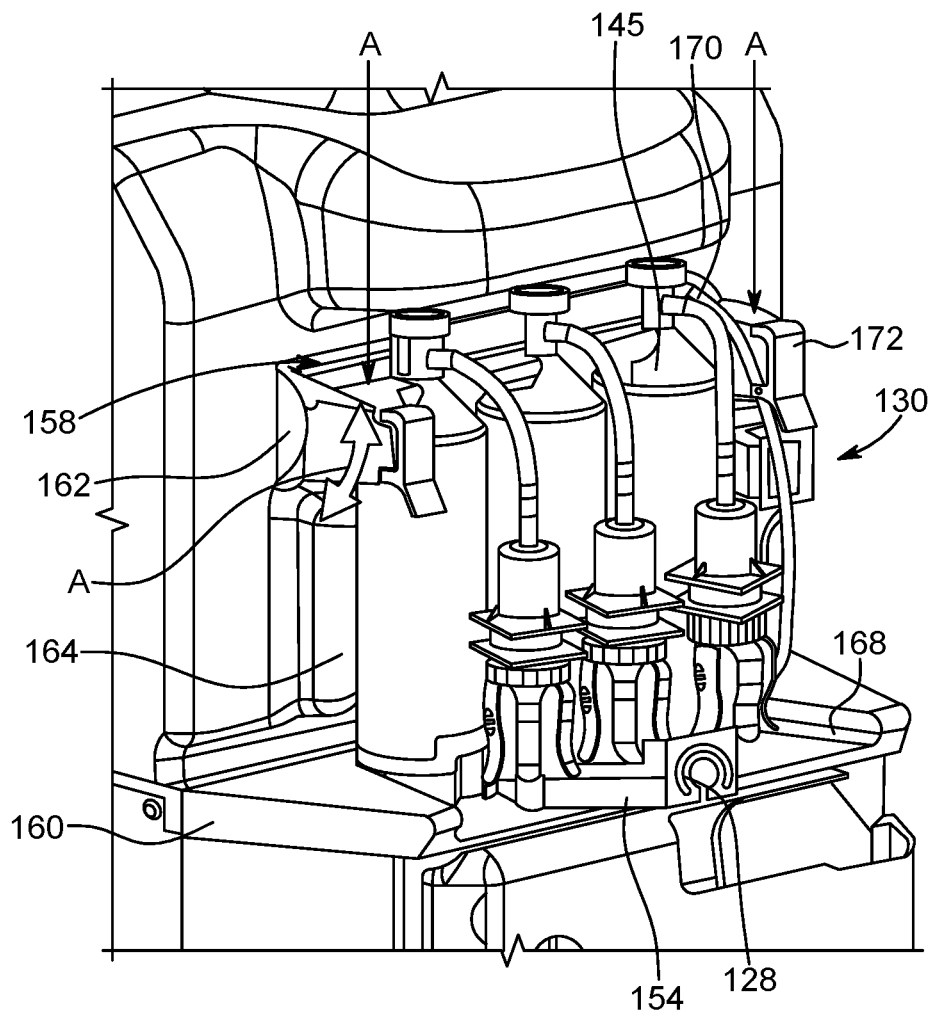
FIG. 4A is a perspective view of the MUDS installed into a receiving slot on the multi-fluid delivery system of FIG. 3A.
Figure 4B:
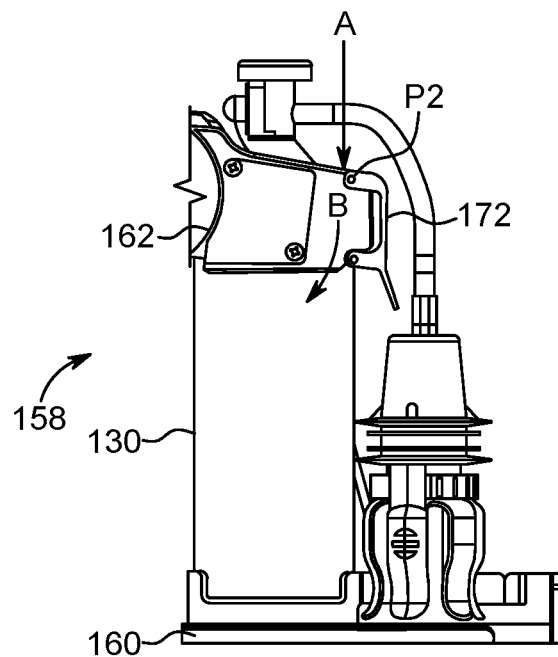
FIG. 4B is a side view of the MUDS of FIG. 4A.

As the MUDS 130 engages the rear sidewall 164, such as shown in FIG. 4A, the MUDS 130 can be locked in the receiving space 158 by moving the top plate 162 to a second position. In the second position, the top plate 162 is lowered such that the apex or cone point 145 of the at least one syringe 132 engages the lower surface of the top plate 162.

Figure 4C:
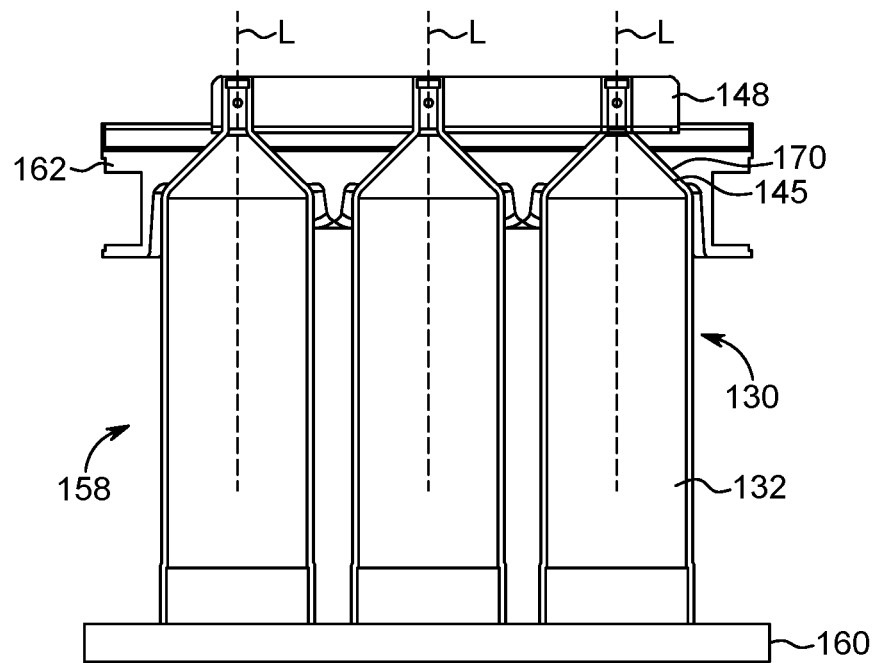
FIG. 4C is a front view of the MUDS of FIG. 4A.

In some aspects, the top plate 162 can be urged to the second position by a biasing mechanism (not shown). In other aspects, the top plate 162 can be manually moved to the second position by pivoting the top plate 162 in a direction of arrow A shown in FIGS. 4A-4B. The top plate 162 can be locked relative to the MUDS 130 to prevent removal of the MUDS 130 from the receiving space 158 by a latch 172. The latch 172 may be operable to prevent the top plate 162 from rotating about the pivot point P1. The latch 172 may be an over-center, spring-loaded latch that is pivotable about a pivot point P2 in a direction of arrow B shown in FIG. 4B. With reference to FIG. 4C, when the MUDS 130 is locked within the receiving space 158, the lower surface of the top plate 162 engages the apex or cone point 145 of the at least one syringe 132. In the locked position, the longitudinal axis L of each syringe 132 is aligned with a center of each syringe slot 170. Removal of the MUDS 130 from the receiving space 158 when the top plate 162 is in the locked position is prevented by the engagement of the lower surface of the top plate 162 with the apex or cone point 145 of the at least one syringe 132. Once locked, the top plate 162 retains the syringes 132 from moving axially during an injection procedure.

Figure 5A:
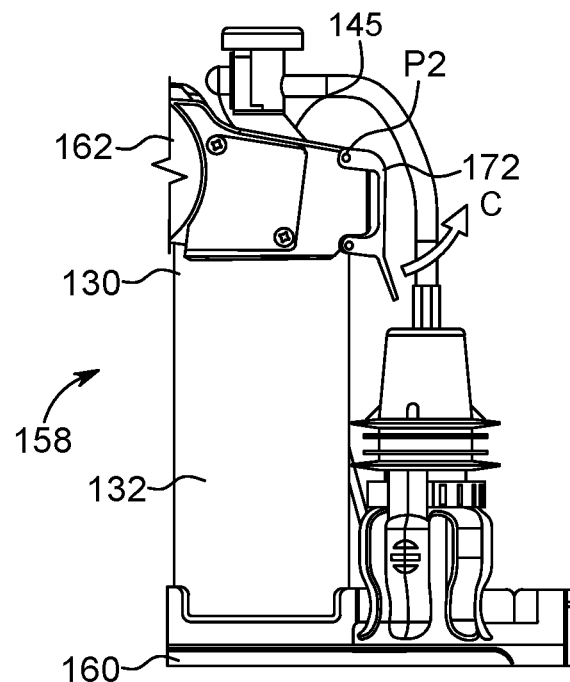
FIG. 5A is a side view of the MUDS prior to removal from the receiving slot on the multi-fluid delivery system of FIG. 3A.
Figure 5B:
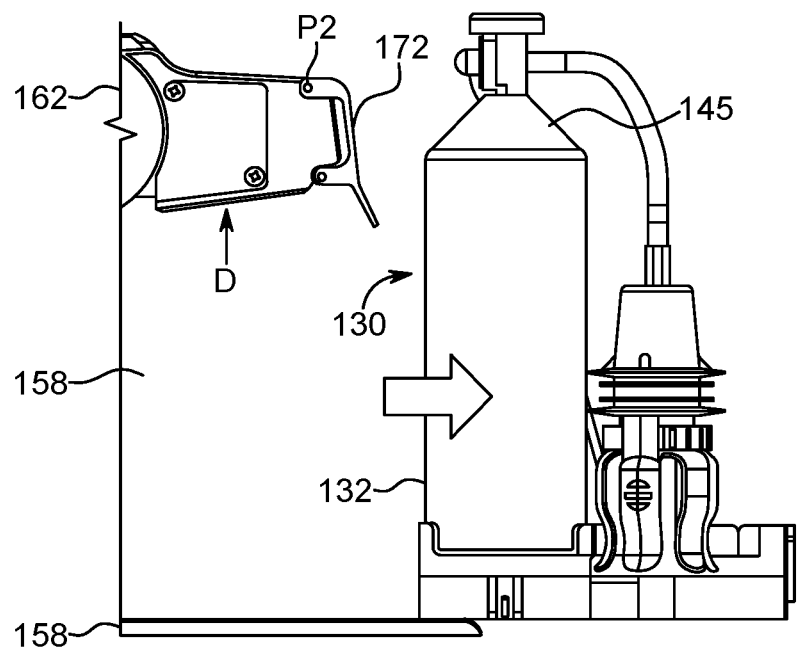
FIG. 5B is a side view of the MUDS after removal from the receiving slot on the multi-fluid delivery system of FIG. 3A.

With reference to FIGS. 5A-5B, the MUDS 130 is removed from the receiving space 158 by unlocking the top plate 162 from the apex or cone point or conical portion 145 of the at least one syringe 132. In the following discussion, it is assumed that the MUDS 130 may be removed from connection with the fluid injector system 100 and discarded as medical waste. In some aspects, the top plate 162 is unlocked by unlatching the latch 172 through a pivoting movement of the latch 172 about the pivot point P2 in a direction of arrow C shown in FIG. 5A. As the latch 172 is unlatched, the top plate 162 is pivoted upwards relative to the MUDS 130 in a direction of arrow D shown in FIG. 5B. By unlocking the top plate 162, the top plate 162 can be moved (i.e., pivoted or raised) relative to the MUDS 130 to allow the apex or cone point or conical portion 145 of the at least one syringe 132 to clear the syringe slot 170 (shown in FIG. 3A) of the top plate 162. The MUDS 130 can then be extracted in a direction opposite the insertion direction by moving the MUDS 130 away from the rear sidewall 164 (shown in FIG. 3A).

Figure 6:
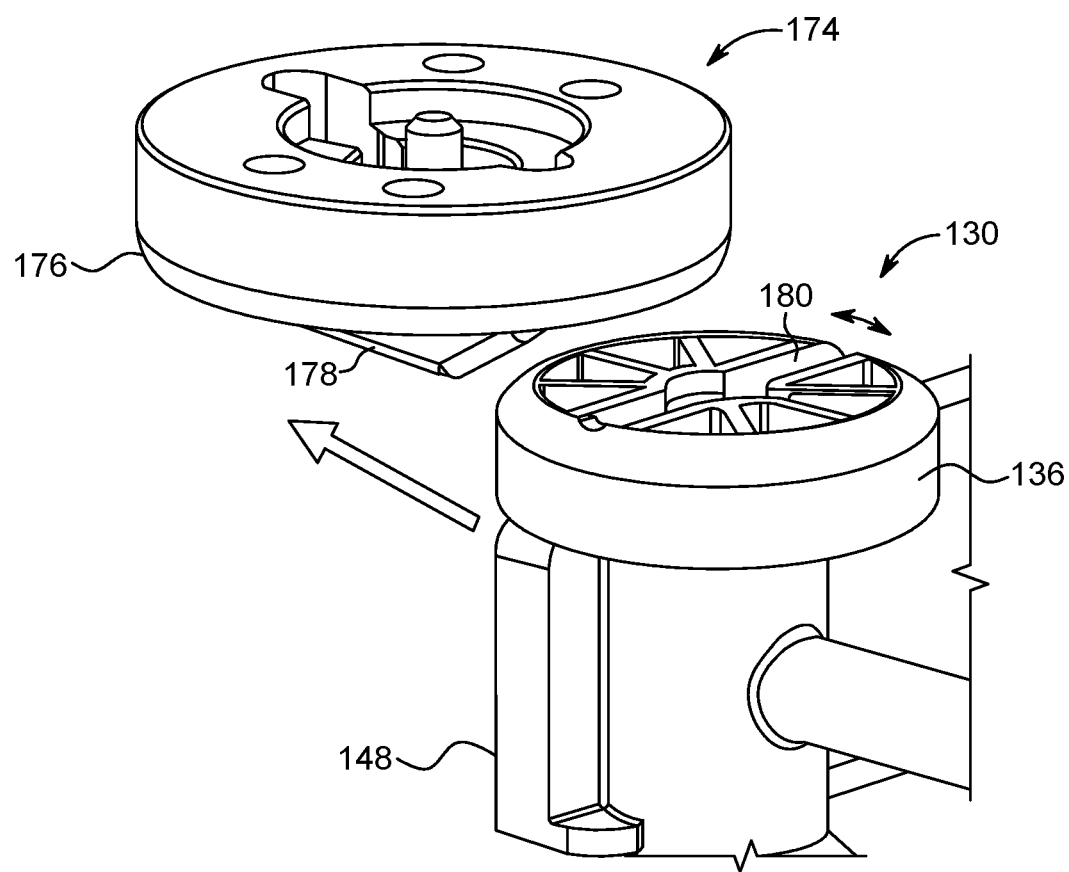
FIG. 6 is a perspective view of a stopcock coupling on a multi-fluid delivery system prior to engagement with a stopcock on a MUDS.

With reference to FIG. 6, in some aspects, the MUDS 130 may have one or more rotatable valves 136 that control fluid flow through the manifold 148. The one or more valves 136 may be rotatable between various positions to effect fluid filling or delivery. In some aspects, a coupling mechanism 174 may be provided to rotate the one or more valves 136 and thereby control the arrangement of the MUDS 130 for fluid filling or delivery. The coupling mechanism 174 may be in the form of a rotatable coupling 176 that engages the at least one rotatable valve 136. In some aspects, the rotatable coupling 176 has a blade 178 that is configured to engage with a slot 180 on the at least one rotatable valve 136. The rotatable coupling 176 may be rotatable using a drive mechanism (not shown) provided on the fluid injector system 100 to rotate coupling 176 by up to 360 degrees until the blade 178 engages slot 180. The coupling mechanism 174 may include a sensor (not shown) that senses when blade 178 engages slot 180 and instructs the coupling mechanism 174 to stop rotating coupling 176. According to various aspects, the coupling mechanism 174 is capable of engaging and coupling to the valve 136 regardless of the initial orientation of the slot 180. Thus, any rotational movement of valve 136, for example during manufacture, shipping, or insertion of MUDS 130, may be compensated for. Once the blade 178 of the rotatable coupling 176 engages the slot 180 on the at least one rotatable valve 136, rotation of the rotatable coupling 176 causes a corresponding rotation of the rotatable valve 136. In this manner, the arrangement of the one or more valves 136 can be switched between a position for filling the one or more syringes 132 (shown in FIG. 3A) and a position for delivering fluid from the one or more syringes 132.

Figure 11:
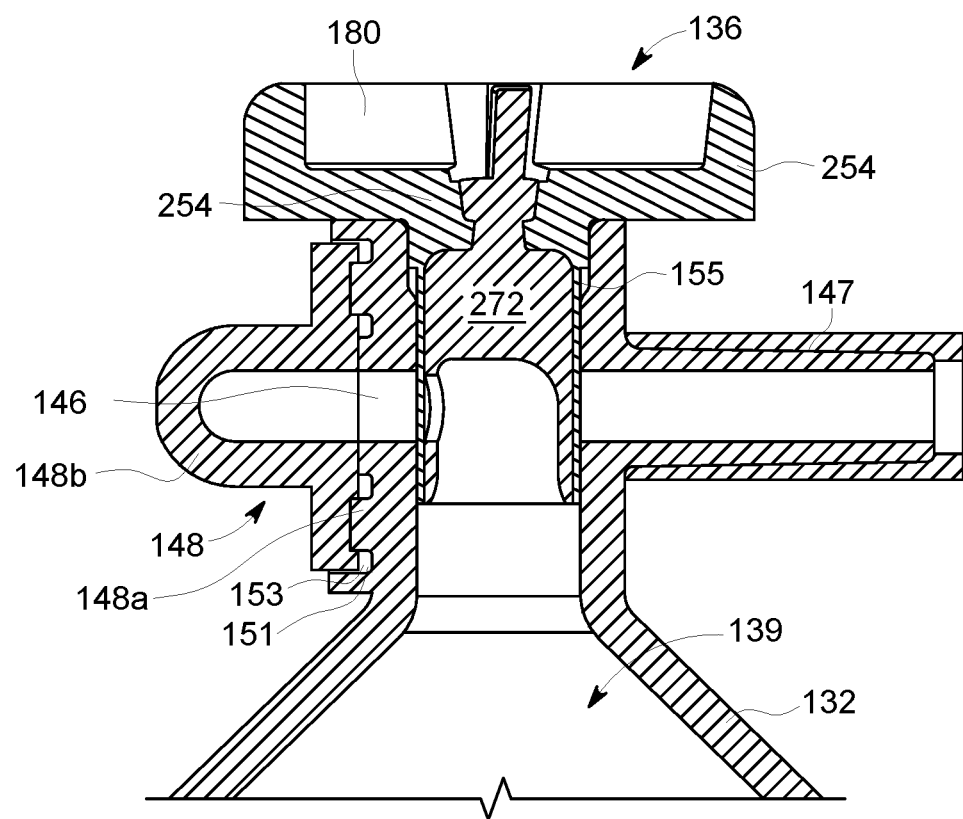
FIG. 11 is a cross-sectional side view of a single syringe of the MUDS.
Figure 12A:
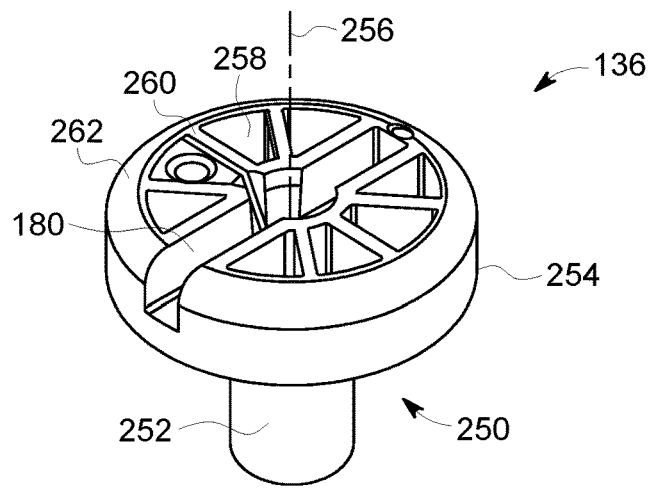
FIG. 12A is a perspective view of a valve for use with the MUDS in accordance with another aspect of the present disclosure.
Figure 12B:
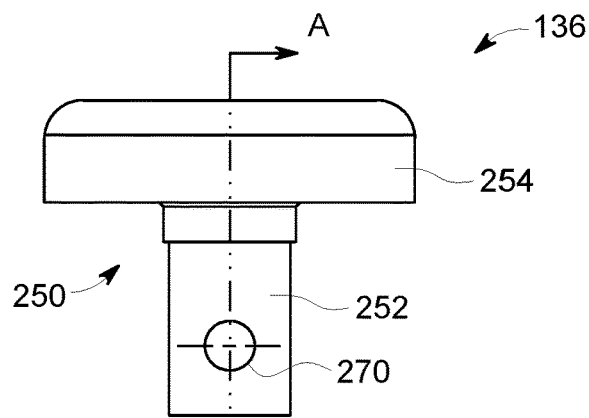
FIG. 12B is a side view of the valve shown in FIG. 12A.
Figure 12C:
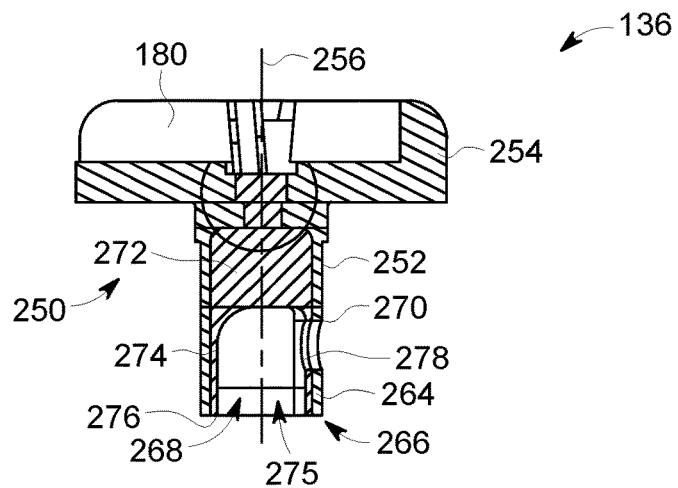
FIG. 12C is a cross-sectional side view of the valve shown in FIG. 12B taken along line A-A.

With reference to FIGS. 12A-12C, the valve 136 has a valve body 250 configured for being rotatably received within at least a portion of the valve receiving cavity 155 (shown in FIG. 11). In some aspects, the valve 136 is configured to be received within the valve receiving cavity 155 in a substantially vertical orientation such that the valve 136 can interface with the coupling mechanism 174 on the injector. The valve body 250 has a valve stem 252 connected to a valve head 254. The valve stem 252 may be shaped to be received within at least a portion of the valve receiving cavity 155. The valve head 254 may be monolithically formed with the valve stem 252, such as by molding. In some aspects, the valve head 254 is formed separately from the valve stem 252 and is removably or non-removably connected to the valve stem 252. The valve stem 252 and the valve head 254 may be formed from same or different materials. In some aspects, the valve stem 252 is formed as a substantially cylindrical member with the valve head 254 monolithically formed with the valve stem 252 such that the valve head 254 extends radially outward relative to the valve stem 252. In various aspects, the valve head 254 may be circular, square, rectangular, or shaped to have any regular or irregular geometric shape having one or more linear or curvilinear edges. The valve stem 252 and the valve head 254 may be aligned or offset relative to a longitudinal axis 256 of the valve 136.

At least a portion of the valve 136 may be made from an elastomeric material to provide sealing against the sidewall of the valve receiving cavity 155. In some aspects, at least a portion of the valve 136 may be made from biocompatible, non-pyrogenic, latex free, and/or DEHP free materials. In other aspects, the valve 136 may be made from a material that is compatible with various medical fluids including, without limitation, various contrast solutions and saline solutions. In other aspects, the valve 136 may be configured for various sterilization techniques, including, without limitation, electron beam sterilization, gamma sterilization, and/or ethylene oxide sterilization. In other aspects, the valve 136 may be configured for use over a predetermined period, such as a period of 24 hours, before the syringe 132, along with the valve 136 must be disposed. In some aspects, the valve 136 may be rated for a maximum operating pressure greater than 350 psi. In other aspects, actuation torque needed to rotate the valve 136 may be less than 3 N-m, with a failure torque greater than 2.5 times the actuation torque. In other aspects, the valve 136 may be configured for rotation at 60 rpm or more. In other aspects, an internal fluid loss of the valve 136 may be less than 0.5% of the total requested volume. In other aspects, the valve 136 may have allowable leakage of less than 0.1 ml for a 200 ml syringe 132.

With reference to FIG. 12A, the valve head 254 has the slot 180 formed as a recess that extends into the valve head 254. In some aspects, the valve head 254 may have a plurality of slots. The slot 180 may extend across at least a portion of an upper surface of the valve head 254. In some aspects, the slot 180 may be aligned with the longitudinal axis 256 of the valve 136 such that the slot 180 extends in a radial direction relative to the longitudinal axis 256. In other aspects, the slot 180 may be offset relative to the longitudinal axis 256 of the valve 136. The slot 180 may have a uniform or non-uniform width along its length. The slot 180 may be surrounded by one or more recesses 258 having one or more ribs 260 extending between the slot 180 and an outer circumference 262 of the valve head 254. The slot 180 may extend at a uniform or non-uniform depth into the valve head 254 along the length of the slot 180. The slot 180 may have a flat bottom, or it may be angled to form a v-shape into the valve head 254.

With reference to FIG. 12C, the valve stem 252 is desirably hollow with a sidewall 264 defining an outer shape of the valve stem 252. The hollow valve stem 252 has an interior 268 with an open bottom end 266. The valve stem 252 has a first side opening 270 extending through the sidewall 264 at a location offset from the bottom end 266. The first side opening 270 is in fluid communication with the interior 268 of the valve stem 252. The first side opening 270 may extend through the sidewall 264 in a direction that is perpendicular or oblique relative to the longitudinal axis 256 of the valve 136. In some aspects, a plurality of first side openings 270 may be provided. In such aspects, the plurality of first side openings 270 may extend circumferentially around an outer circumference of the valve stem 252 and/or axially along the longitudinal axis 256 of the valve 136.

With reference to FIG. 12C, an insert 272 may be received within the interior 268 of the valve stem 252. In some aspects, the insert 272 may be monolithically formed with the valve 136, such as by co-molding the insert 272 with the valve 136. At least a portion of the insert 272 may extend into the recess 258 formed on the valve head 254 to prevent rotation of the insert 272 relative to the valve stem 252. The insert 272 has a hollow body with a circumferential sidewall 274 surrounding an interior 275 having an open bottom end 276. At least one second side opening 278 extends through the sidewall 274 of the hollow body of the insert 272. The second side opening 278 is aligned with the first side opening 270 of the valve stem 252 such that the first side opening 270 and the second side opening 278 are in fluid communication with each other. In this manner, the first side opening 270 is in fluid communication with the interior 275 of the insert 272 by way of an L-shaped fluid path.

Figure 7A:
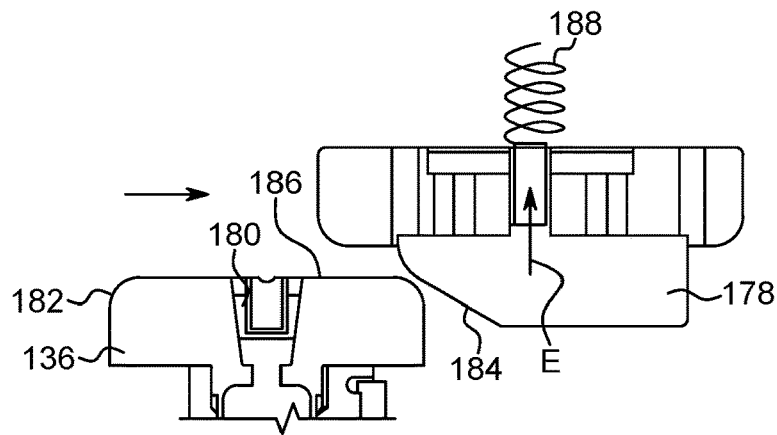
FIG. 7A is a side cross-sectional view of the stopcock coupling prior to engagement with the stopcock shown in FIG. 6.
Figure 7B:
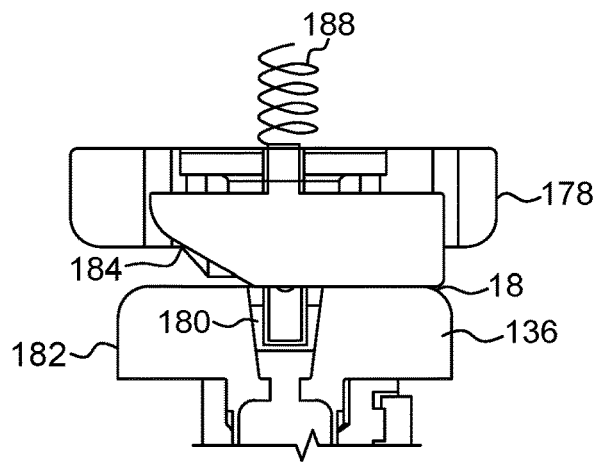
FIG. 7B is a side cross-sectional view of the stopcock coupling during initial engagement with the stopcock shown in FIG. 6.
Figure 7C:
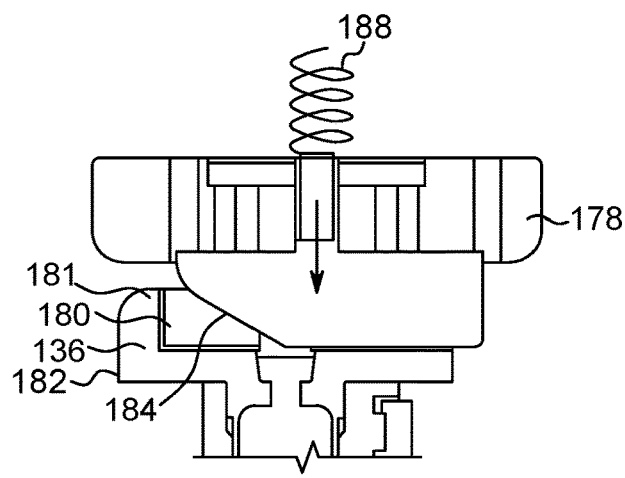
FIG. 7C is a side cross-sectional view of the stopcock coupling during final engagement with the stopcock shown in FIG. 6.

Prior to connection with the fluid injector system 100, the one or more valves 136 may be misaligned relative to the coupling mechanism 174 on the fluid injector system 100. In order to align the one or more valves 136 for rotation with the coupling mechanism 174, the rotatable coupling 176 is rotatable into self-alignment with the at least one valve 136. As the MUDS 130 (shown in FIG. 3A) is loaded into the receiving space 158 of the fluid injector system 100, at least a portion of the valve 136, such as a portion of its outer sidewall 182 (shown in FIG. 7A), engages at least a portion of the rotatable coupling 176. Referring to FIG. 7A, the blade 178 of the rotatable coupling 176 may have an inclined surface 184 that is angled relative to the outer sidewall 182 of the valve 136. Upon contact with the inclined surface 184, the outer sidewall 182 of the valve 136 slides along the inclined surface 184 as the MUDS 130 is moved into the receiving space 158. Valve sidewall 182 may include a beveled, chamfered, or rounded edge 183 on the distal perimeter of the valve side wall 182 which may facilitate engagement between the inclined surface 184 and the valve 136. Such sliding movement causes the rotatable coupling 176 to move vertically in a direction of arrow E in FIG. 7A. In some aspects, the rotatable coupling 176 may be spring-loaded, such that, when the blade 178 is moved in the direction of arrow E, for example when the blade 178 is not correctly aligned with slot 180, a restoring force is stored in an elastically-resilient member 188. As shown in FIG. 7C, slot 180 may have a lip 181 on one end which limits the orientation of the blade 178 to a single orientation for insertion into slot 180, for example when inclined surface 184 of blade 178 is adjacent to the lip 181. When the MUDS 130 is fully inserted into the receiving space, the blade 178 of the rotatable coupling 176 is positioned on an upper surface 186 of the valve 136. To align the valve 136 with the rotatable coupling 176, the rotatable coupling 176 is rotated relative to the valve 136 until the blade 178 is aligned with the slot 180. Once aligned, the blade 178 is lowered into the slot 180. The rotatable coupling 176 may then be urged into the slot 180 under the restoring action of the elastically-resilient member 188. The slot 180 may have sidewalls that narrow starting from the upper surface 186 to facilitate the insertion of the blade 178 into the slot 180. Once the blade 178 is inserted into the slot 180, the rotatable coupling 176 can adjust the orientation of the valve 136 for fluid filling or delivery, as described herein. As there is only one correct orientation between each valve 136 and each rotatable coupling 176, an operating system of the injector can determine the orientation of each valve 136 and determine the correct rotation of each rotatable coupling 176 necessary for filling or delivering fluid from each of the plurality of syringes 132 of the MUDS 130.

Having generally described the components of the fluid injector system 100 and the MUDS 130, the structure and method of use of a SUDS 190 and its interaction with MUDS 130 will now be described.

Figure 8A:
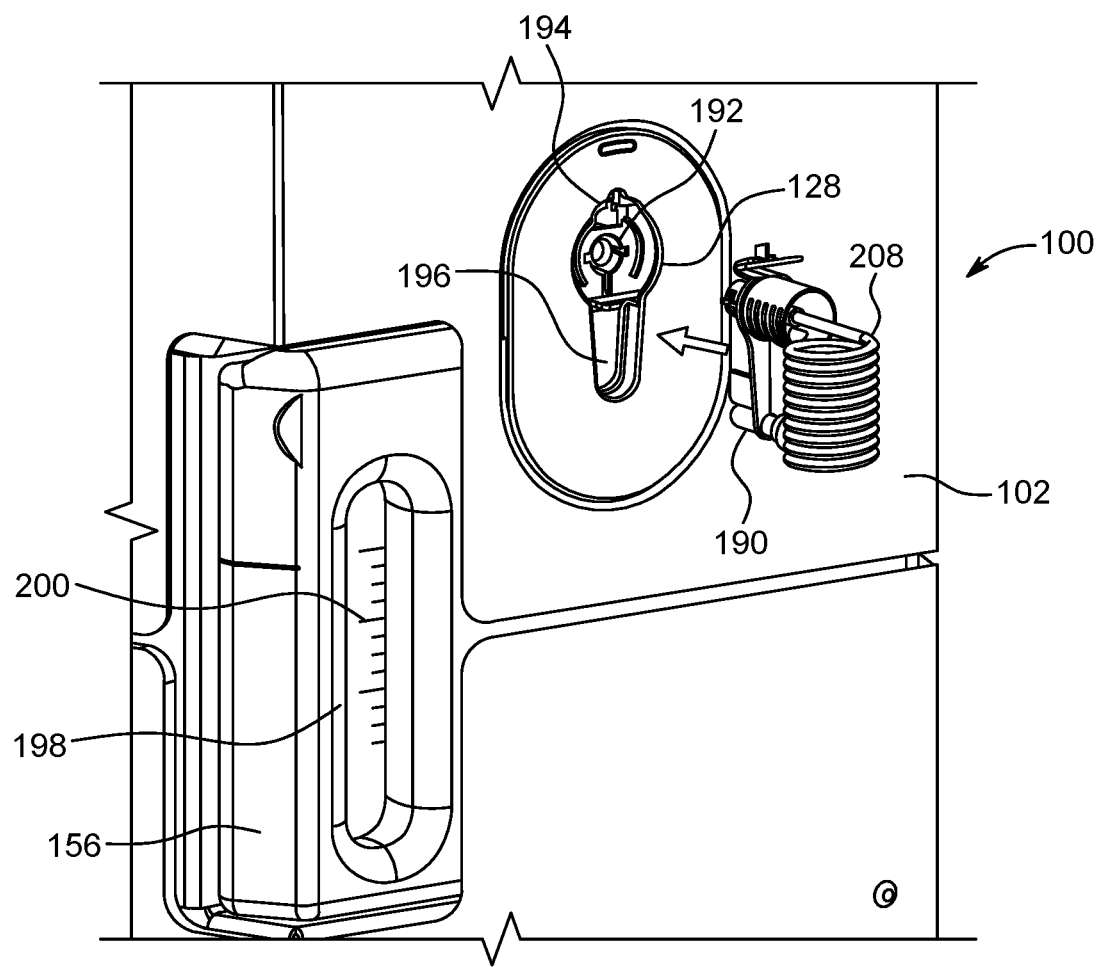
FIG. 8A is a perspective view of a connection interface prior to connecting a SUDS connector with a multi-fluid delivery system.
Figure 8B:
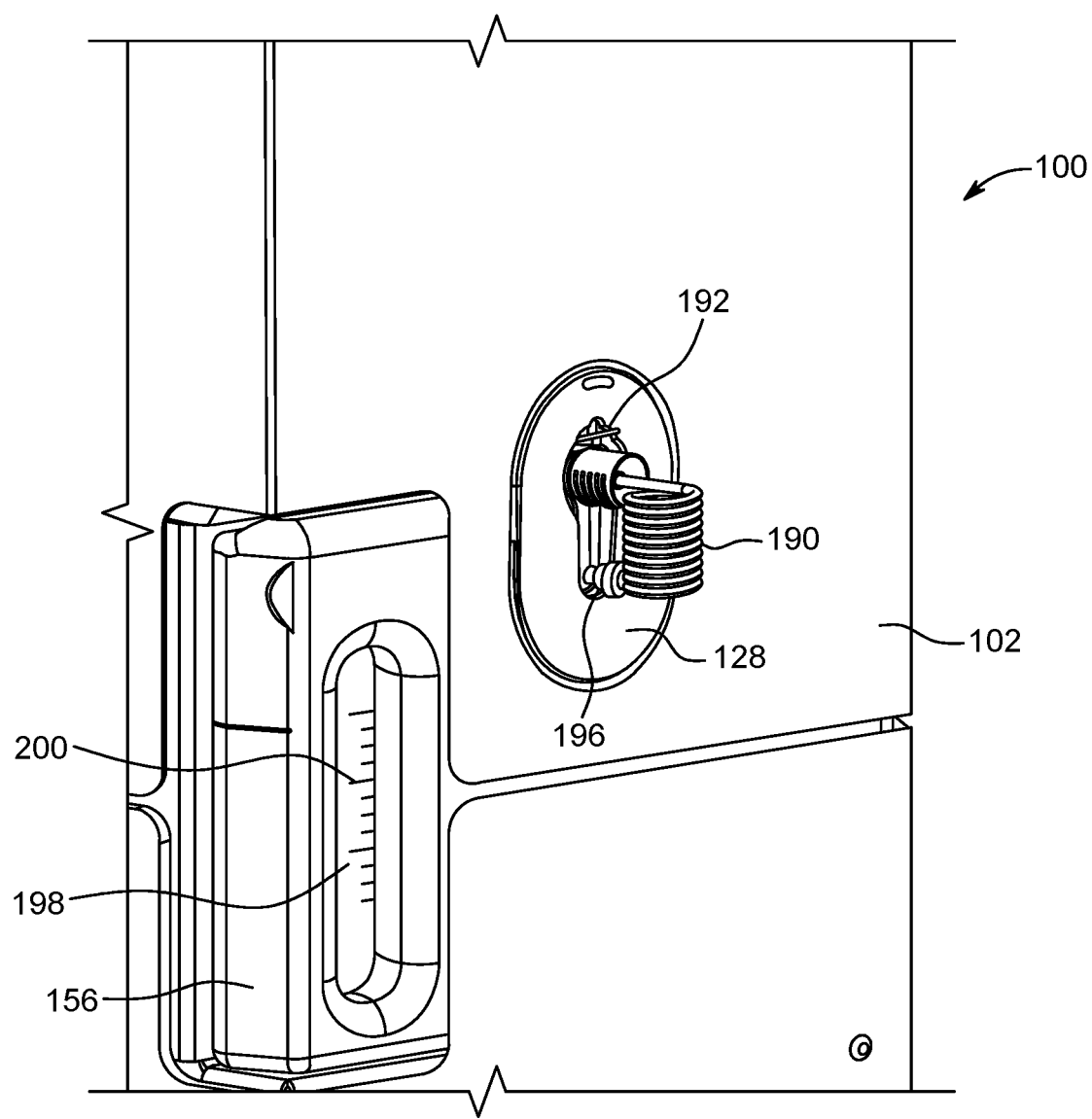
FIG. 8B is a perspective view of the connection interface of FIG. 8A showing the SUDS connector connected with the multi-fluid delivery system.

With reference to FIGS. 8A and 8B, the fluid injector system 100 has a connection port 192 that is configured to form a releasable fluid connection with at least a portion of the SUDS 190. In some aspects, the connection port 192 may be formed on the MUDS 130. The connection port 192 may be shielded by at least a portion of the housing 102 of the fluid injector system 100. For example, recessing the connection port 192 within the interior of the housing 102 may preserve the sterility of the connection port 192 by preventing or limiting a user or patient from touching and contaminating the portions of the connection port 192 that contact the fluid to be injected to the patient. In some aspects, the connection port 192 is recessed within an opening 194 formed on the housing 102 of the fluid injector system 100, or the connection port 192 may have a shielding structure (not shown) that surrounds at least a portion of the connection port 192. In other aspects, the connection port 192 may be formed directly on the housing 102 and connected to the MUDS 130 by a fluid path (not shown). As described herein, the SUDS 190 may be connected to the connection port 192, formed on at least a portion of the MUDS 130 and/or the housing 102. Desirably, the connection between the SUDS 190 and the connection port 192 is a releasable connection to allow the SUDS 190 to be selectively disconnected from the connection port 192 (FIG. 8A) and connected to the connection port 192 (FIG. 8B). In some aspects, the SUDS 190 may be disconnected from the connection port 192 and disposed after each fluid delivery procedure and a new SUDS 190 may be connected to the connection port 192 for a subsequent fluid delivery procedure.

With continued reference to FIGS. 8A and 8B, a waste inlet port 196 may be provided separately from the connection port 192. The waste inlet port 196 is in fluid communication with the waste reservoir 156. In some aspects, the waste reservoir 156 is provided separately from the SUDS 190 such that the fluid from the waste inlet port 196 can be delivered to the waste reservoir 156. At least a portion of the SUDS 190 may be releasably connected to or associated with the waste inlet port 196 for introducing waste fluid into the waste reservoir 156 during, for example, a priming operation that expels air from the SUDS 190. The waste reservoir 156 may have a viewing window 198 with indicia 200, such as graduated markings, that indicate the fill level of the waste reservoir 156.

Figure 9A:
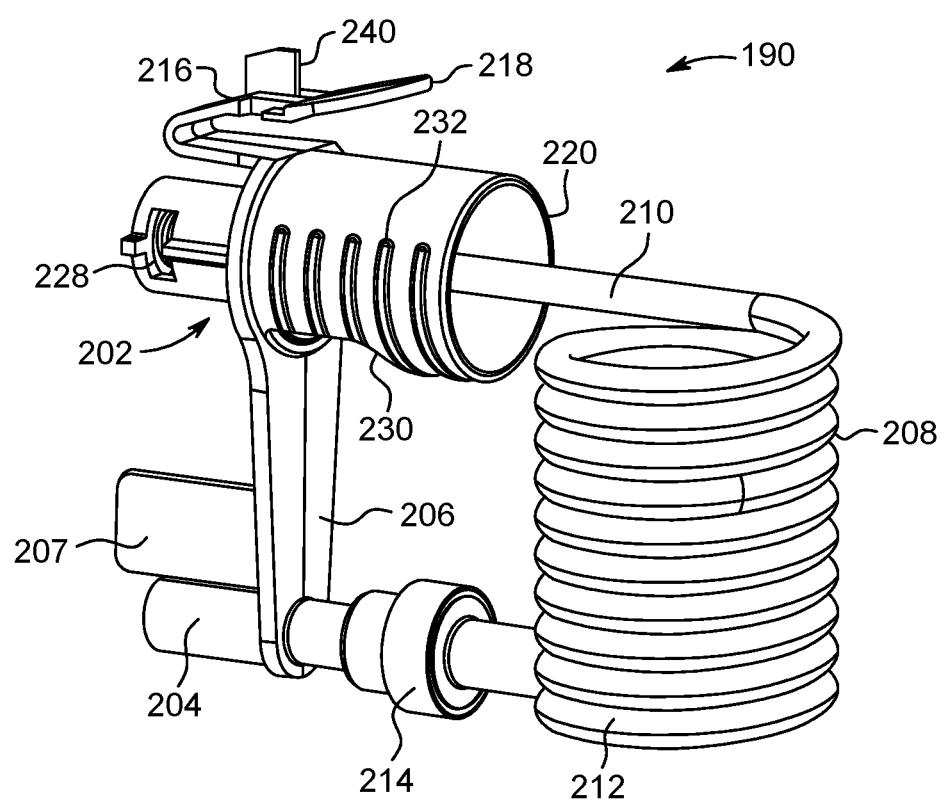
FIG. 9A is a perspective view of a SUDS connector in accordance with one aspect.
Figure 9B:
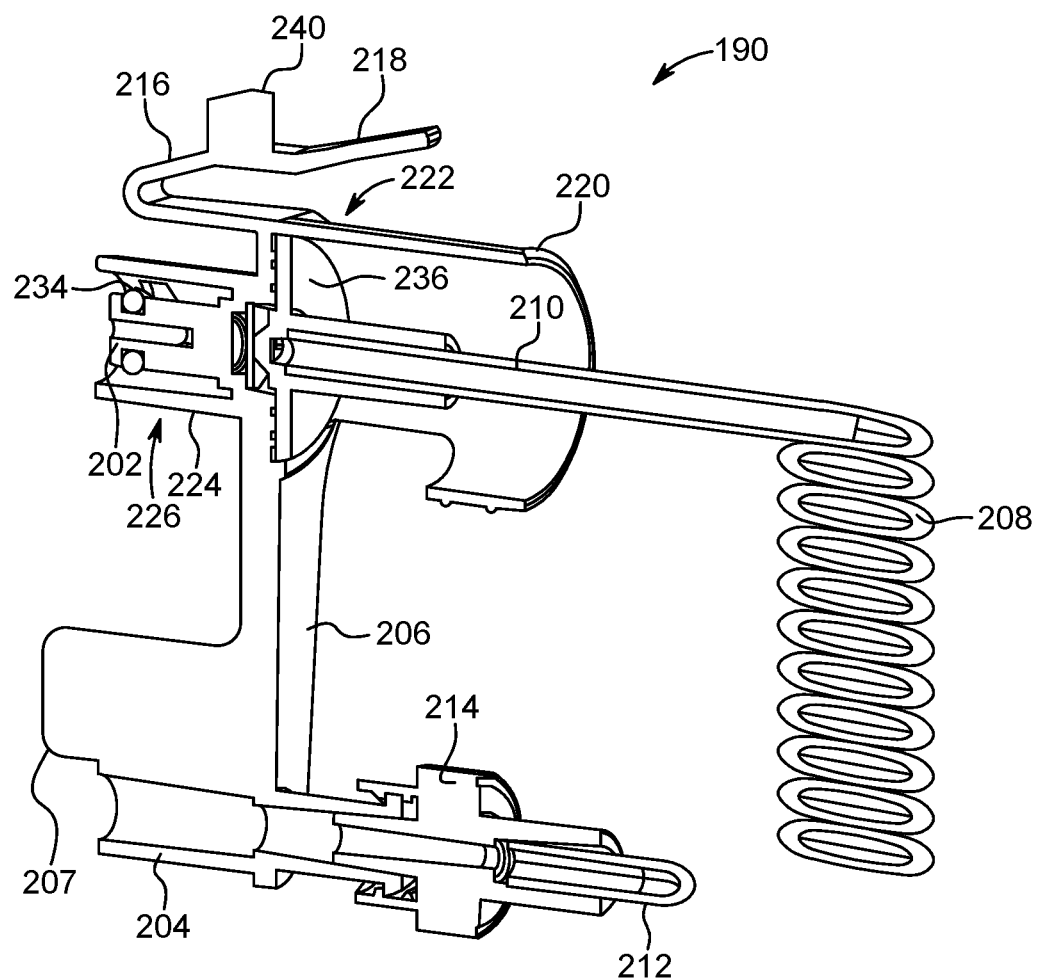
FIG. 9B is a cross-sectional view of the SUDS connector shown in FIG. 9A.

With reference to FIG. 9A, the SUDS 190 has a fluid inlet port 202 that is configured for releasable connection with the connection port 192 (shown in FIG. 8A). The fluid inlet port 202 receives fluid delivered from the fluid injector system 100. The fluid inlet port 202 is desirably a hollow, tubular structure, as shown in FIG. 9B. The SUDS 190 further has a waste outlet port 204 that is configured for releasable connection or association with the waste inlet port 196 (shown in FIG. 8A). The waste outlet port 204 receives waste fluid and delivers such waste fluid to the waste reservoir 156 during, for example, a priming operation of the SUDS 190. The waste outlet port 204 is desirably a hollow, tubular structure, as shown in FIG. 9B. The waste outlet port 204 may be connected to, inserted into, or located in the waste inlet port 202 so that the waste fluid may flow through the waste inlet port 202 and continue into waste reservoir 156. The fluid inlet port 202 and the waste outlet port 204 may be spaced apart from each other by a spacer 206. In some aspects, the spacer 206 is dimensioned to position the fluid inlet port 202 and the waste outlet port 204 for alignment with the connection port 192 and the waste inlet port 196, respectively. It is noted that the SUDS 190 is shown in FIG. 9A in a state after removal from packaging (not shown). Prior to use, the SUDS 190 is desirably packaged in a pre-sterilized, sealed package that protects the SUDS 190 from contamination with air or surface-borne contaminants. Alternatively, the sealed package and SUDS 190 may be sterilized after packaging.

The SUDS 190 desirably has an asymmetrical structure, so that the user can only attach the SUDS 190 to the MUDS 130 in one orientation. In this manner, the user is prevented from attaching the fluid inlet port 202 to the waste inlet port 196. In some aspects, a fin 207 may be provided on at least a portion of the SUDS 190 to prevent erroneous insertion of the SUDS 190 in the connection port 192. In certain aspects, the fin 207 may be formed on the spacer 206 proximate to the waste outlet port 204. In this manner, the fin 207 may interfere with the incorrect insertion of the SUDS 190 into the connection port 192. Structures and shapes other than a fin 207 may be used to prevent erroneous insertion of the SUDS 190 into connection port 192, In some aspects, tubing 208 may be connected at its proximal end 210 to the fluid inlet port 202. The tubing 208 is configured to deliver fluid received from the fluid inlet port 202. The distal end 212 of the tubing 208 may have a connector 214 that is configured for connection with the waste outlet port 204 or a fluid path connected to the patient (not shown). The tubing 208 may be made from a flexible material, such as a medical grade plastic material, that allows the tubing 208 to be coiled. The connector 214 may be a luer-lock connector (either a male luer-lock connector or a female luer-lock connector depending on the desired application) or other medical connector configuration. In some aspects, the connector 214 may have a one-way valve to prevent backflow of fluid. Alternatively, a one-way valve may be located elsewhere in the SUDS 190 between fluid inlet port 202 and connector 214.

With continued reference to FIG. 9A, the SUDS 190 may have a locking tab 216 that is configured for selectively locking the SUDS 190 with the fluid injector system 100 depending on the engagement of the locking tab 216 with at least a portion of the fluid injector system 100. In some aspects, the locking tab 216 may be a flexible tab that is deflectable between an engaged position and a disengaged position by deflecting at least a portion of the locking tab 216. The locking tab 216 may have a pressing surface 218 that, when pressed, causes the locking tab 216 to be deflected from the engaged position to the disengaged position for insertion and removal of the SUDS 190 from the fluid injector system 100. In some aspects, the locking tab 216 may be configured for releasable locking engagement with a receiving slot 217 on the MUDS 130 (shown in FIG. 9C).

With reference to FIG. 9B, the SUDS 190 may have a first annular skirt 224 extending circumferentially around a proximal end 226 of the fluid inlet port 202 and a second annular skirt 220 extending circumferentially around a distal end 222 of the fluid inlet port 202. The first and second annular skirts 224, 220 surround the fluid inlet port 202 to prevent inadvertent contact and contamination. The first annular skirt 224 may have one or more recesses 228 (shown in FIG. 9A) extending through a sidewall thereof. The one or more recesses 228 may provide a locking interface with a corresponding locking element (not shown) on the fluid injector system 100. The second annular skirt 220 may have at least one indentation 230 (shown in FIG. 9A) to facilitate grasping and handling of the SUDS 190. In some aspects, the second annular skirt 220 may have a textured surface having one or more ribs 232 (shown in FIG. 9A) to facilitate gripping and handling of the SUDS 190.

With continued reference to FIG. 9B, at least one annular seal 234 may be provided around the proximal end 226 of the fluid inlet port 202. The at least one annular seal 234 may seal the fluid inlet port 202 to prevent fluid from leaking through the SUDS 190. The at least one annular seal 234 may provide a fluid seal between the SUDS 190 and the MUDS 130 when they are fluidly connected with one another to allow fluid to flow from the MUDS 130 to the SUDS 190 without leaking. A one-way valve 236 may be provided within a lumen of the fluid inlet port 202 to prevent fluid from flowing in a reverse direction from the SUDS 190 into the MUDS 130.

Figure 9C:
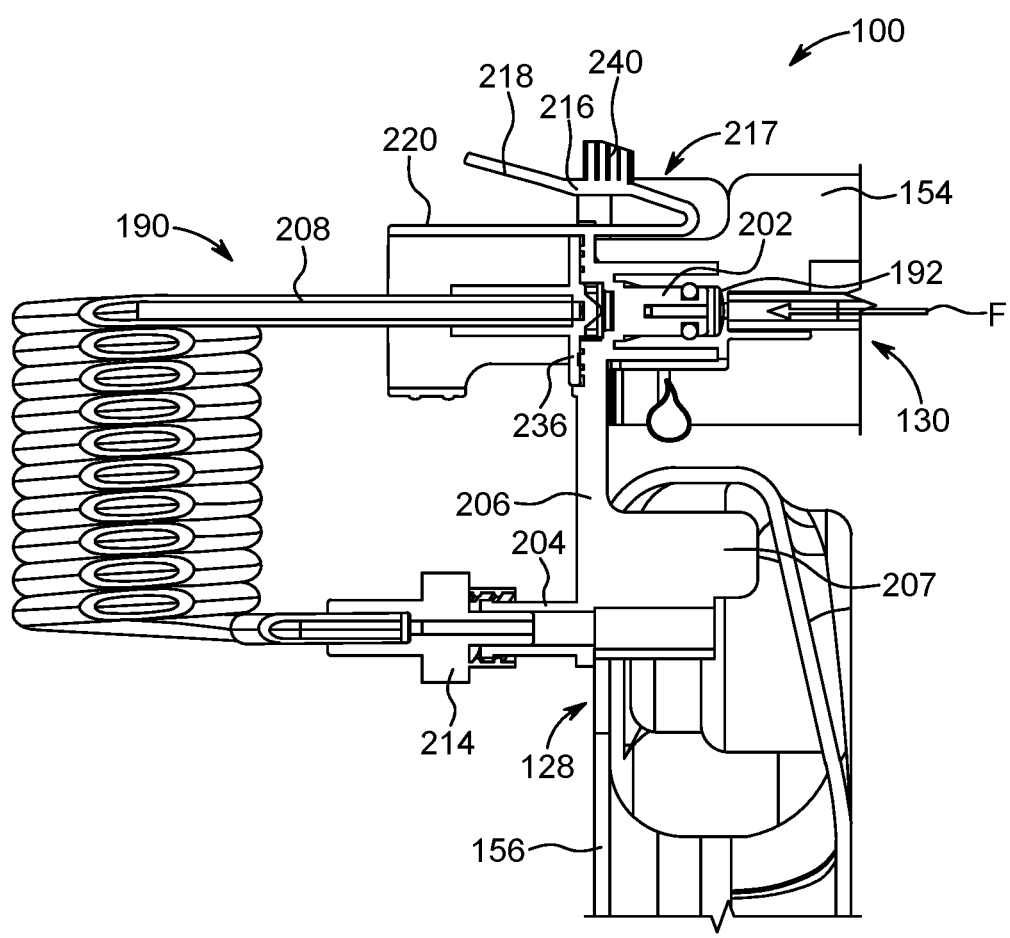
FIG. 9C is a cross-sectional view of the SUDS connector shown in FIG. 9A connected to a port of a multi-fluid delivery system.

With reference to FIG. 9C, the SUDS 190 shown in FIG. 9A is shown connected to the fluid injector system 100. While FIG. 9C illustrates the connection port 192 formed on the MUDS 130, in other aspects, the connection port 192 may be formed on a portion of the housing 102 (shown in FIG. 1). The fluid inlet port 202 of the SUDS 190 is connected to the connection port 192 to establish a fluid path in a direction of arrow F shown in FIG. 9C. Fluid passing through the fluid inlet port 202 flows through the one-way valve 236 and into tubing 208. Any fluid that may drip from the interface between the fluid inlet port 202 and the connection port 192 is collected in the waste reservoir 156. The waste reservoir 156 may be shaped to collect any fluid that may drip from the SUDS 190 when it is removed from the MUDS 130. Additionally, when the SUDS 190 is connected to the connection port 192, the outlet of the waste outlet port 204 is positioned within the waste inlet port 196 such that waste fluid from the tubing 208 may be discharged into the waste reservoir 156. The spacer 206 may define an insertion stop surface to define the depth of insertion of the SUDS 190 into the connection port 192.

FIGS. 13-24 illustrate various connection configurations between the terminal end of the apex or cone point or distal conical end 145 of the one or more syringes 132 and the manifold 148 including at least one manifold conduit, wherein the manifold conduit 148*a* is in fluid connection with a main fluid channel 148*b* and a conduit syringe attachment end, wherein the conduit syringe attachment end is in fluid communication with the syringe fluid port of the at least one syringe 132. According to these aspects, the at least one manifold conduit 148*a* comprises a filling port 147 configured for fluid communication with a MUDS fluid line 134, a discharge outlet 146 in fluid communication with the main fluid channel 148*b*, and a valve receiving cavity 155, wherein the discharge outlet 146 and the filling port 147 are in fluid communication with an interior 139 of the at least one syringe 132 through a valve assembly 272 in a valve receiving cavity 155.

With reference to FIGS. 13A-C, one aspect of a syringe/manifold connection configuration including a swivel nut connection is shown. The distal conical end 1346 of the at least one syringe 132 includes a male luer tip and a circumferential groove 1390. Circumferential groove 1390 is configured to receive an inward radial flange 1385 of threaded swivel nut 1380 including internal threads 1382. Conduit syringe attachment end 1372 of manifold conduit 1370 includes a female luer tip configured for fluid tight connection with male luer tip of distal conical end 1346. Internal threads 1382 threadibly interact with complementary threads 1375 on the conduit syringe attachment end 1372 of manifold conduit 1370 to connect the manifold conduit 1370 with distal conical end 1346.

Figure 14B:
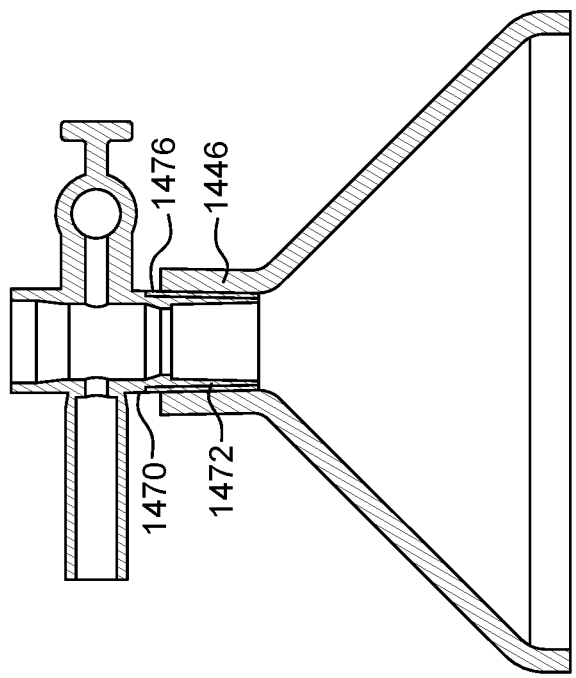
FIGS. 14A and 14B illustrate an aspect of a syringe/manifold connection configuration.
Figure 14A:
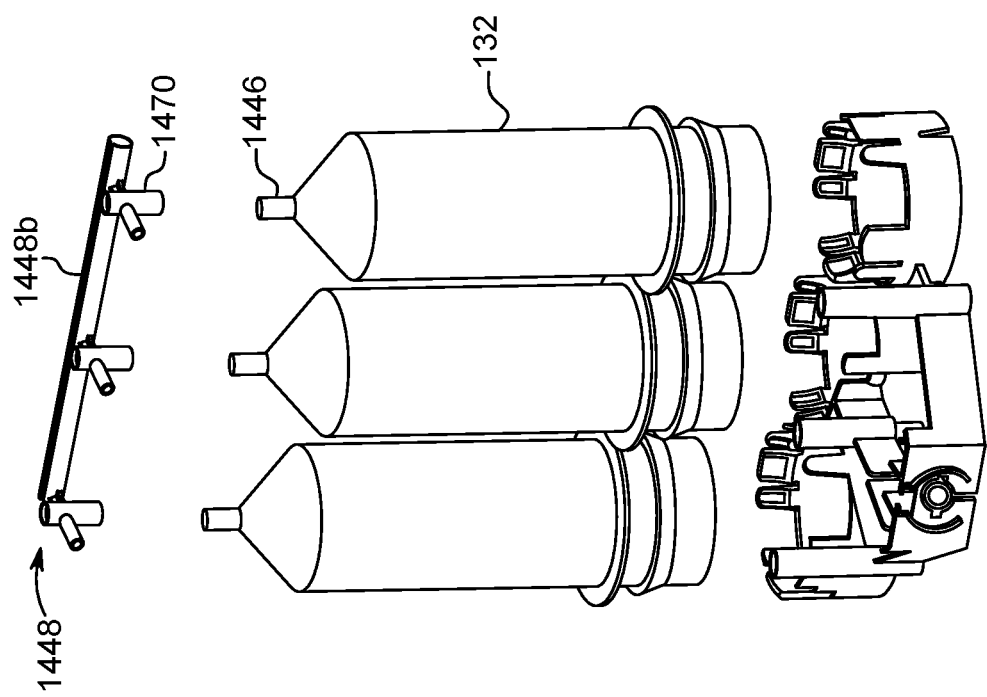
Figure 15B:
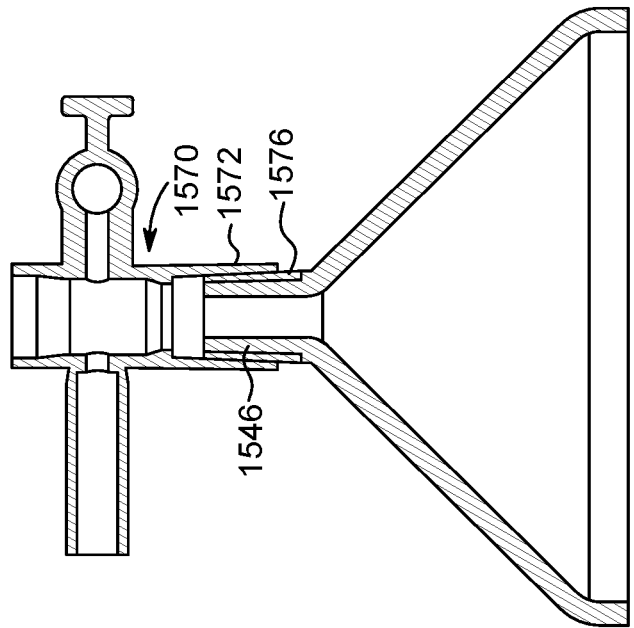
FIGS. 15A and 15B illustrate an aspect of a syringe/manifold connection configuration.
Figure 15A:
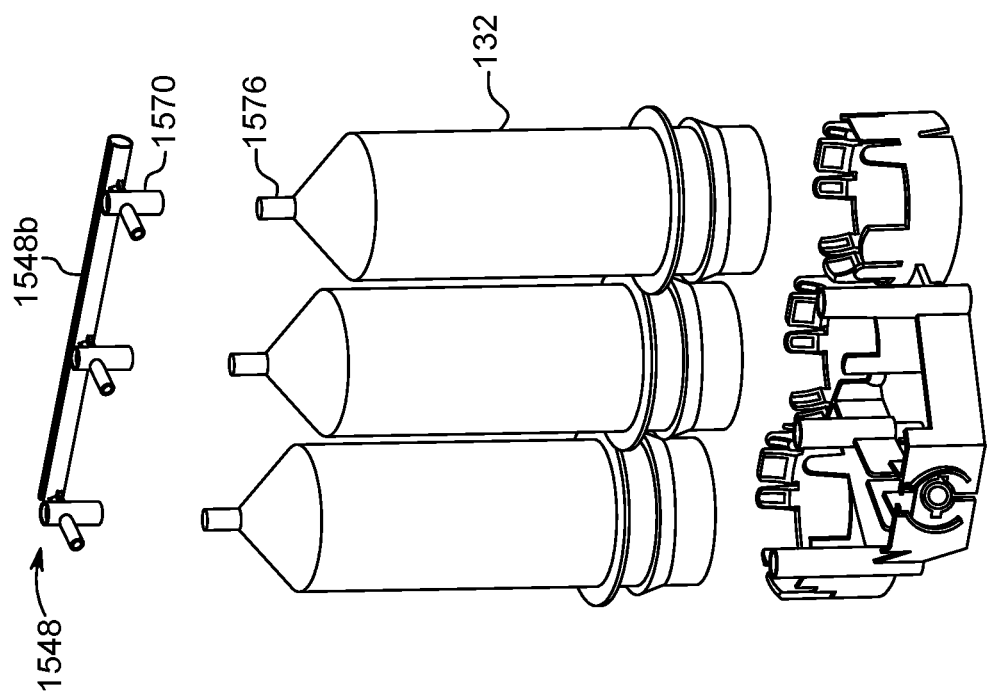

With reference to FIGS. 14A-B, one aspect of a syringe/manifold connection configuration including an overmolded manifold connection with solvent bond is shown. The conduit syringe attachment end 1472 of the at least one manifold conduit 1470 comprises an overmolded polymer sheath 1476 that forms a fluid tight connection by a solvent bond between an outer surface of the conduit syringe attachment end 1472 and an inner surface of the syringe fluid port 1446. In certain aspects the at least one syringe and/or manifold conduit 1470 may be made of a first polymeric material, such as, for example polycarbonate, and the overmolded polymer sheath 1476 may be made of a second polymeric material, such as polyurethane, that may be overmolded on the conduit syringe attachment end 1472 during manufacture. The polymeric sheath 1476 may then be treated with a solvent, such as but not limited to cyclohexanone, methyl ethyl ketone or other suitable solvent, that at least partially dissolves the second polymeric material, forming a solvent bond with between the two surfaces upon setting. According to another aspect illustrated in FIGS. 15A and 15B, the syringe fluid port 1546 may comprise the overmolded polymer sheath 1576 that has been overmolded on an outer surface of the syringe fluid port 1546, which then forms a fluid tight connection and seal with the inner surface of the conduit syringe attachment end 1572 of the at least one manifold conduit 1570.

Figure 16C:
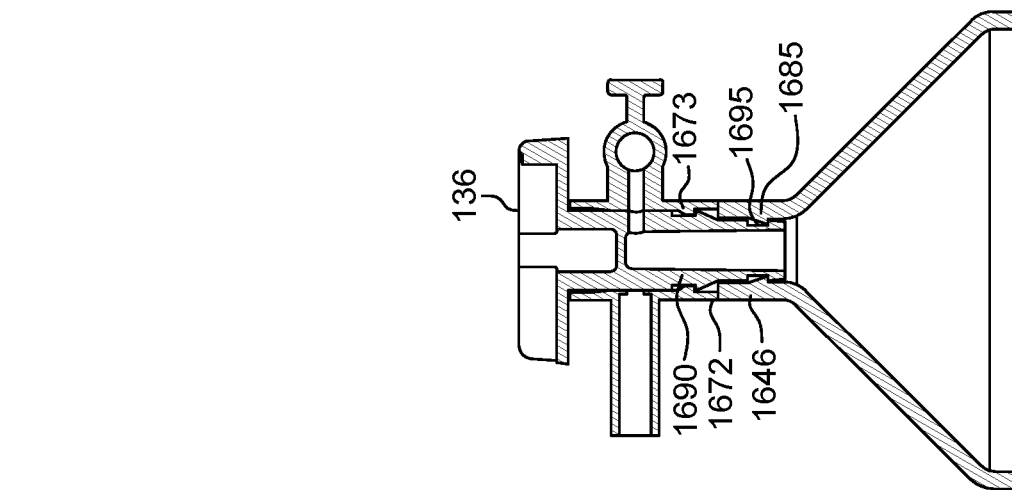
FIGS. 16A-C illustrate an aspect of a syringe/manifold connection configuration.
Figure 16B:
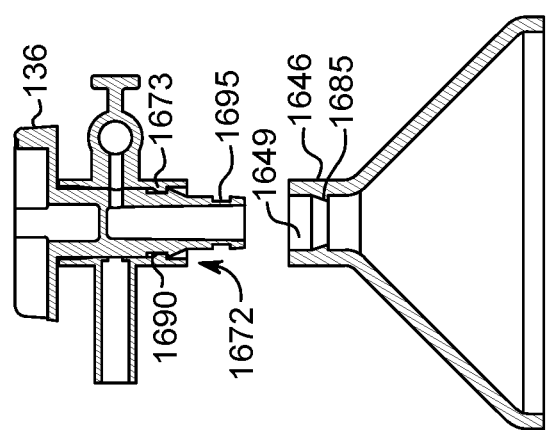
Figure 16A:
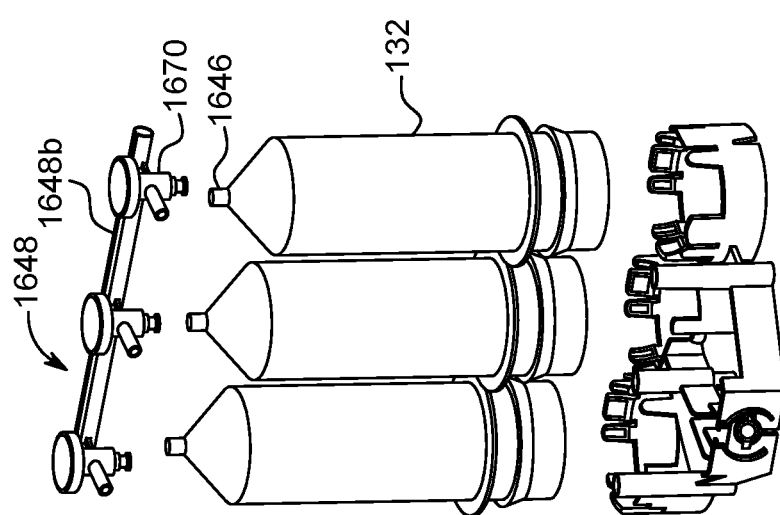

With reference to FIGS. 16A-C, one aspect of a syringe/manifold connection configuration including a stem lock configuration using the stem of the valve assembly 136 to connect the syringe and manifold is shown. According to this aspect, an inner surface 1649 of the syringe fluid port 1646 comprises a locking flange 1685 extending radially inward and the inner surface of the conduit syringe attachment end 1672 comprises a locking flange 1673 extending radially inward. Valve assembly 136 comprises a syringe locking groove 1695 and a manifold locking groove 1690 configured to form locking engagements with the locking flanges 1685, 1673 of the syringe fluid port 1646 and conduit syringe attachment end 1672. Certain aspects may further include one or more o-rings between the valve assembly and one or both of the syringe fluid port 1646 and conduit syringe attachment end 1672.

With reference to FIGS. 17A-C, one aspect of a syringe/manifold connection configuration including a UV activated adhesive. According to this aspect, the outer circumferential surface of the conduit syringe attachment end 1772 is bonded to an inner circumferential surface of the syringe fluid port 1746 by a UV activated adhesive. To accommodate for potential swelling of the UV activated adhesive during cure, the syringe fill port 1746 may comprise a plurality of lateral slots 1790 to allow for expansion of the UV activated adhesive during the curing process, where excess adhesive may expand through the lateral slots 1790. In another aspect (not shown), the conduit syringe attachment end 1772 may comprise a plurality of lateral slots to allow for expansion of the UV activated adhesive during the curing process, where excess adhesive may expand through the lateral slots.

With reference to FIGS. 18A-C, one aspect of a syringe/manifold connection configuration including a plurality of flexible clip elements is shown. According to one aspect the conical distal end 145 may comprise a plurality of distally facing flexible clips 1890 configured to engage a radial flange 1875 on an outer circumference of the conduit syringe attachment end 1872 of the manifold conduit 1870. The syringe fluid port 1846 may include a male luer tip that sealably engages a female luer tip on the conduit syringe attachment end 1872. In other aspect (not shown), the flexible clips may be located on the conduit syringe attachment end 1872 and project proximally to engage a corresponding flange on the syringe fluid port 1846.

With reference to FIGS. 19A-D, one aspect of a syringe/manifold connection configuration including a C-clip locking feature is shown. According to this aspect, syringe fluid port 1946 includes a longitudinal slot 1995 and the conduit syringe attachment end 1972 comprises a radial flange 1975. The conduit syringe attachment end 1972 is inserted into the syringe fluid port 1946 to a point where the radial flange 1975 is immediately proximal to the longitudinal slot 1995. Connection between the conduit syringe attachment end 1972 and the syringe fluid port 1746 is maintained by a C-clip 1990 inserted into longitudinal slot 1995 immediately distal to the radial flange. The conduit syringe attachment end 1972 may further comprise one or more O-rings 1999 configured to form a fluid tight seal between the conduit syringe attachment end 1972 and the syringe fluid port 1946.

Figure 20B:
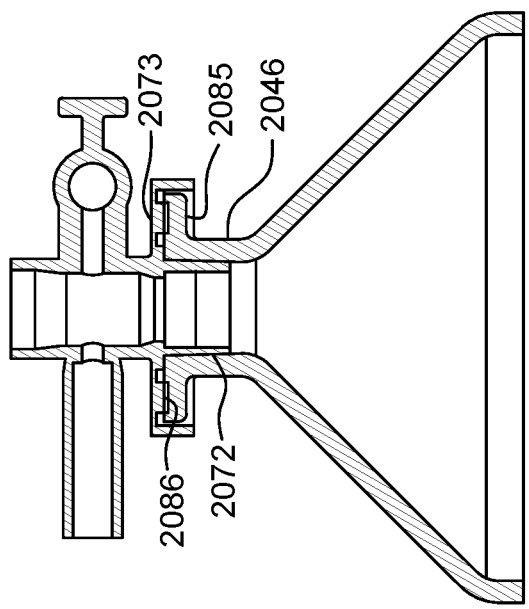
FIGS. 20A and 20B illustrate an aspect of a syringe/manifold connection configuration.
Figure 20A:
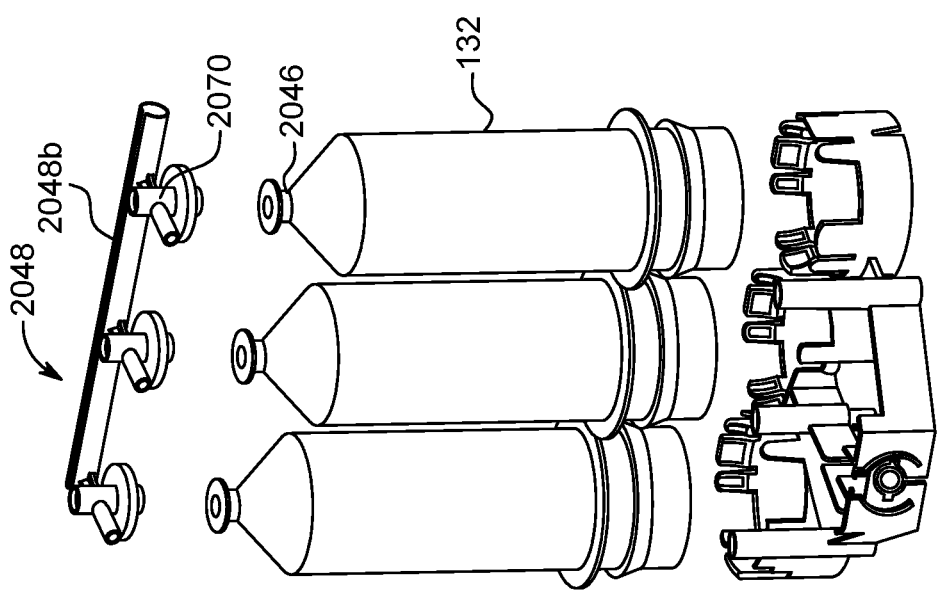

With reference to FIGS. 20A-B, one aspect of a syringe/manifold connection configuration including a laser weld feature is shown. According to this aspect, one of the syringe fluid port 2046 and the conduit syringe attachment end 2072 comprises a radial flange 2085 with a surface configured for laser welding and the other of the syringe fluid port 2046 and the conduit syringe attachment end 2072 comprises a complementary radial receiving flange 2073 that receives the radial flange 2085 and has a complementary surface configured for laser welding. The radial flange 2085 and the complimentary radial receiving flange 2073 are connected by a laser weld 2086 therebetween.

Figure 21B:
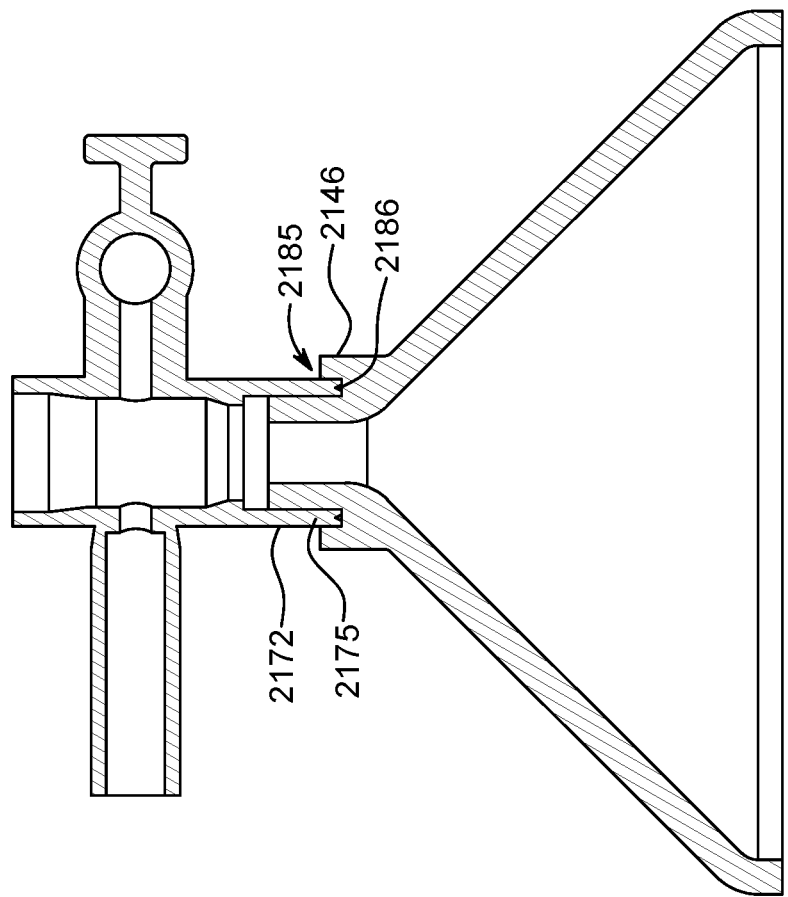
FIGS. 21A and 21B illustrate an aspect of a syringe/manifold connection configuration.
Figure 21A:
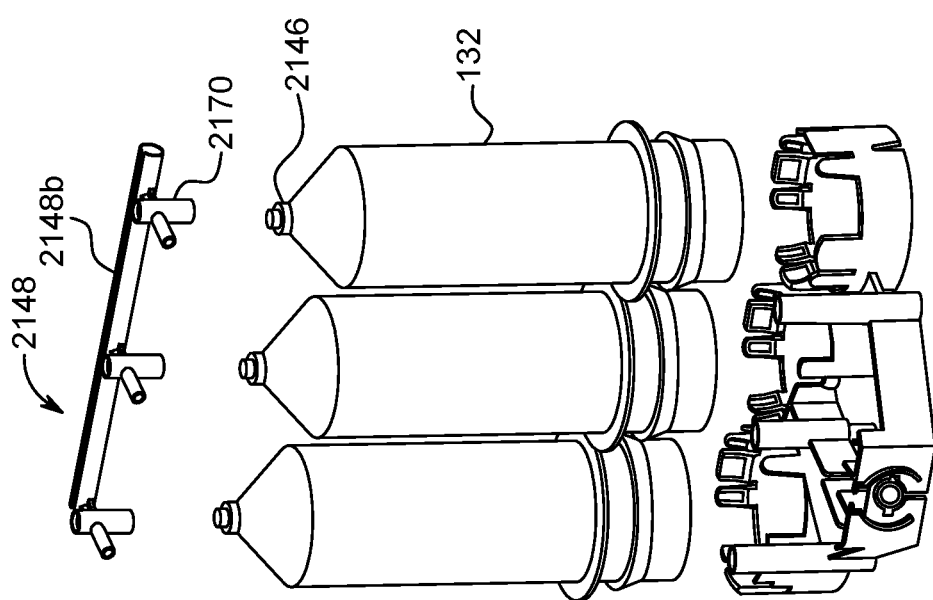

With reference to FIGS. 21A-B, one aspect of a syringe/manifold connection configuration including an ultrasonic weld feature is shown. According to this aspect, one of the syringe fluid port 2146 and the conduit syringe attachment end 2172 comprises a circumferential receiving slot 2185 including an energy director 2186 and the other of the syringe fluid port 2146 and the conduit syringe attachment end 2172 comprises a terminal portion 2175 that engages and is received in the circumferential receiving slot 2185. The terminal portion 2175 and the circumferential receiving slog 2185 are connected by an ultrasonic weld therebetween by exposure to ultrasonic vibrations, which may be directed by energy director 2186.

Figure 22B:
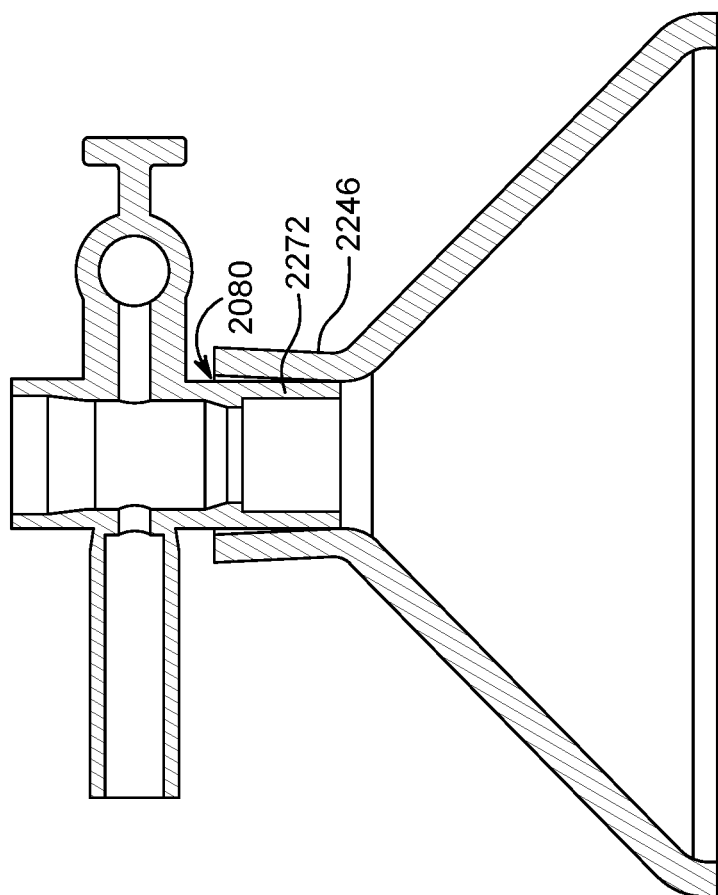
FIGS. 22A and 22B illustrate an aspect of a syringe/manifold connection configuration.
Figure 22A:
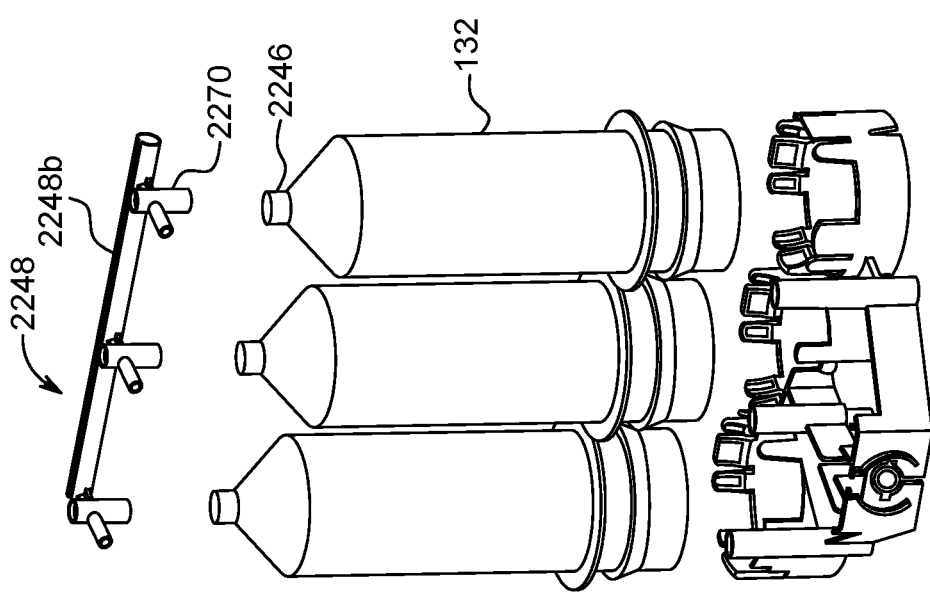

With reference to FIGS. 22A-B, one aspect of a syringe/manifold connection configuration including luer seal with UV adhesive bond is shown. According to this aspect, the syringe fluid port 2246 may comprise a female luer connector which forms a liquid tight connection with a male luer connector on the conduit syringe attachment end 2272. When assembling the luer connection, a distal circumferential slot 2080 is formed between the syringe fluid port 2246 and the conduit syringe attachment end 2272. The distal circumferential slot 2080 is configured for receiving a UV activated adhesive which forms an adhesive connection between the syringe fluid port 2246 and the conduit syringe attachment end 2272 upon irradiation with UV radiation. Reversal of the luer connections between the syringe fluid port 2246 and the conduit syringe attachment end 2272 is also contemplated.

Figure 23B:
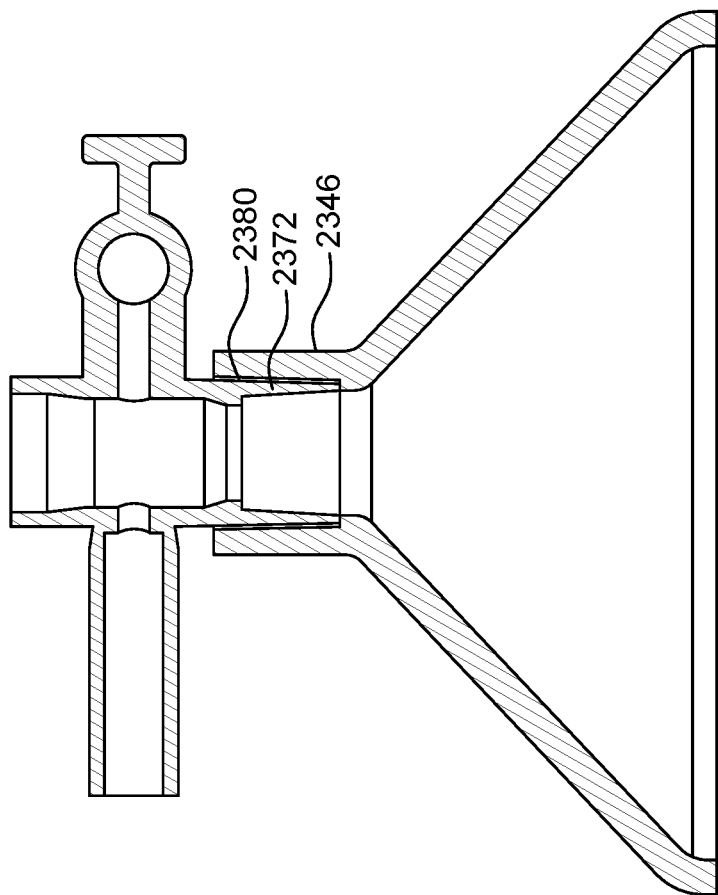
FIGS. 23A and 23B illustrate an aspect of a syringe/manifold connection configuration.
Figure 23A:
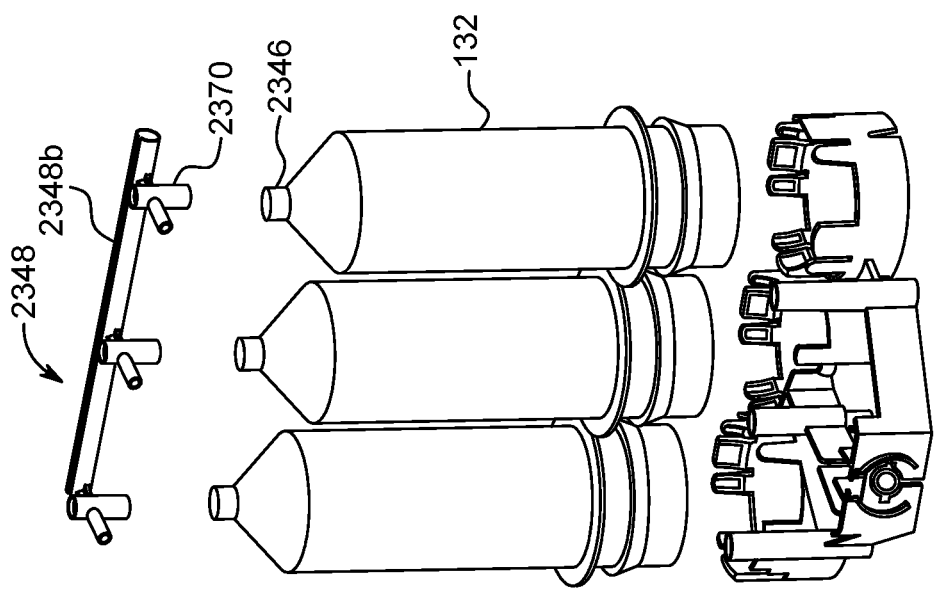

With reference to FIGS. 23A-B, one aspect of a syringe/manifold connection configuration including a UV adhesive bond between the syringe fluid port 2346 and the manifold conduit 2370 is shown. According to this aspect, engagement between the syringe fluid port 2346 and the conduit syringe attachment end 2372 defines a tubular space 2380 between an inner surface of the syringe fluid port 2346 and an outer surface of the conduit syringe attachment end 2372. When assembling the connection, a UV activated adhesive is received within the tubular space 2380 which forms an adhesive connection between the syringe fluid port 2346 and the conduit syringe attachment end 2372 upon irradiation with UV radiation. Reversal of the connections between the syringe fluid port 2346 and the conduit syringe attachment end 2372 is also contemplated.

Figure 24B:
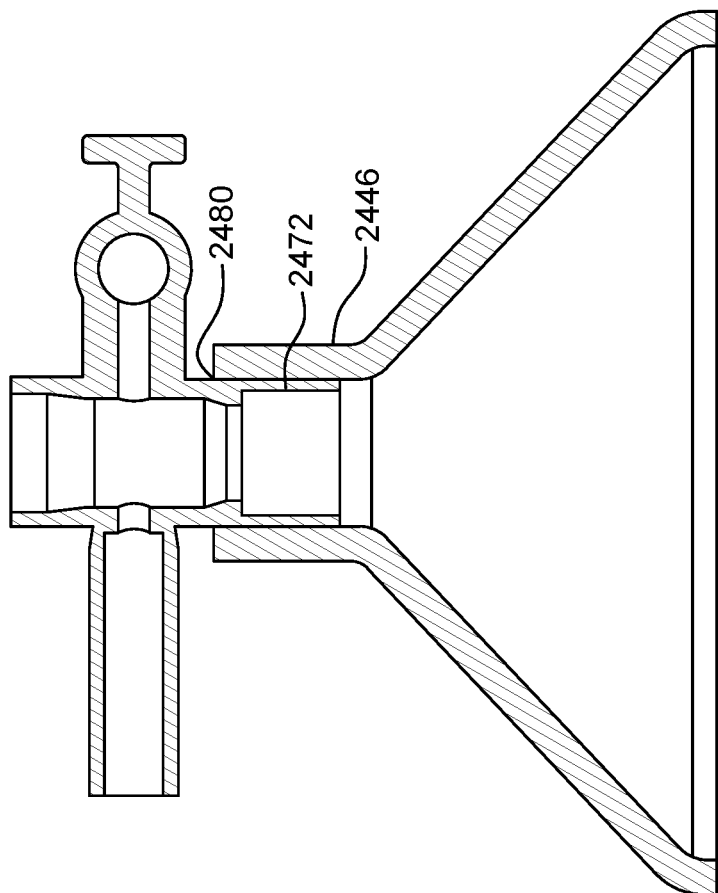
FIGS. 24A and 24B illustrate an aspect of a syringe/manifold connection configuration.
Figure 24A:
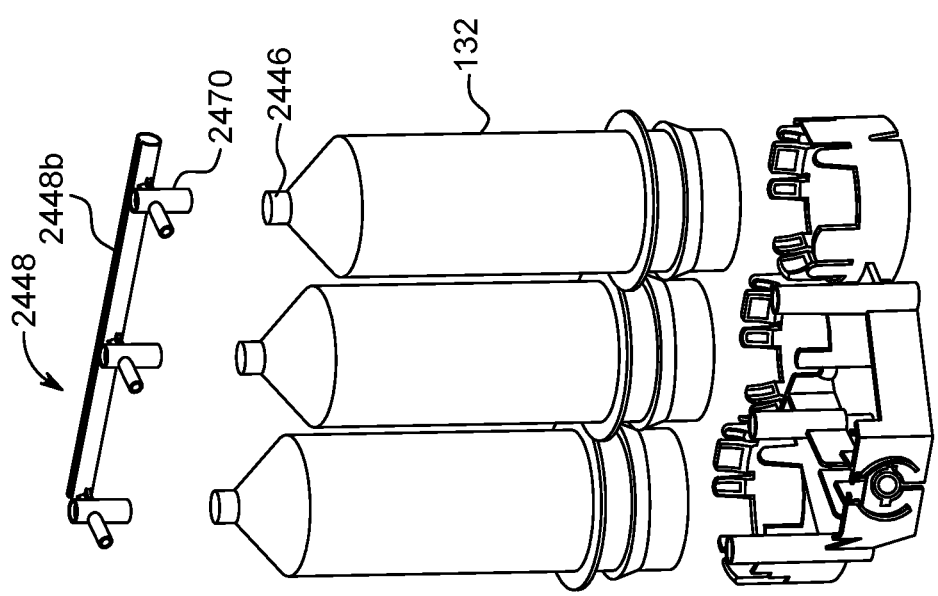

With reference to FIGS. 24A-B, one aspect of a syringe/manifold connection configuration including luer seal with a laser tack weld is shown. According to this aspect, the syringe fluid port 2446 may comprise a female luer connector which forms a liquid tight connection with a male luer connector on the conduit syringe attachment end 2472. Upon assembling the luer connection, a laser tack weld 2480 is formed at the interface between the syringe fluid port 2446 and the conduit syringe attachment end 2472. Reversal of the luer connections between the syringe fluid port 2246 and the conduit syringe attachment end 2272 is also contemplated.

Figure 25A:
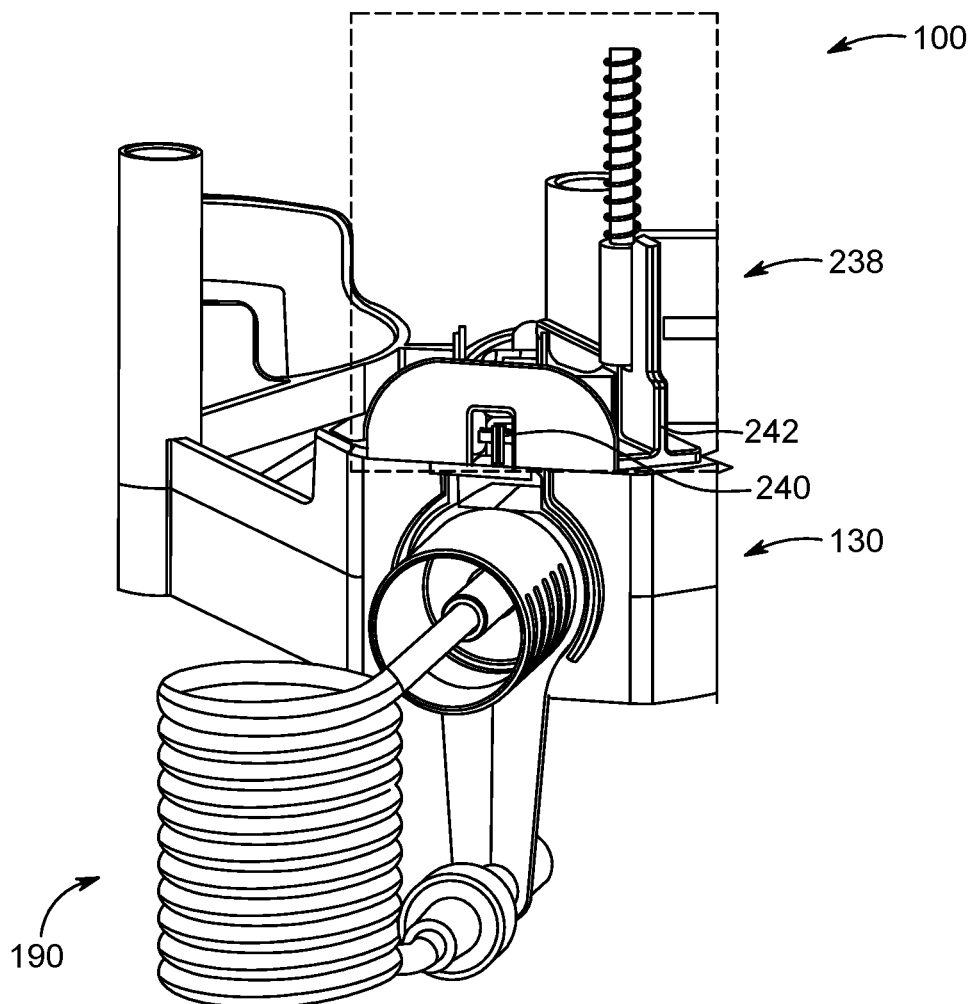
FIG. 25A is a perspective view of the SUDS connector shown in FIG. 9C with a portion of the multi-fluid delivery system and the MUDS cut away.
Figure 25B:
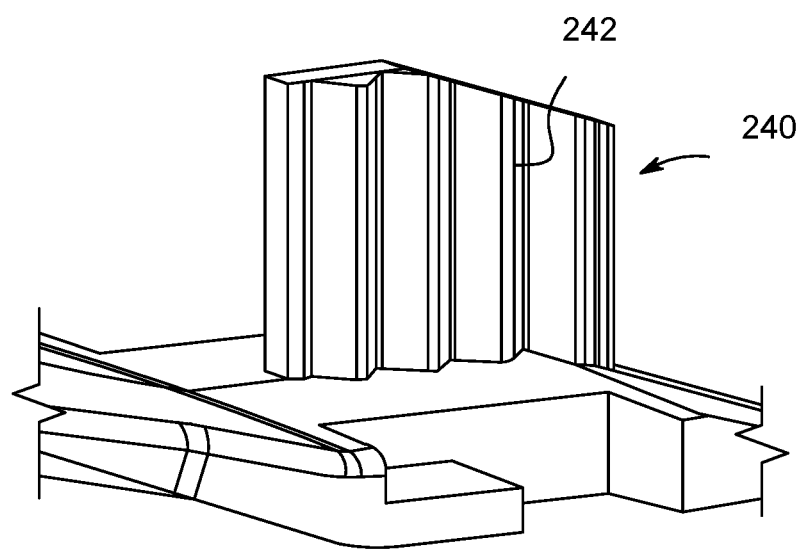
FIG. 25B is a detailed perspective view of a sensor rib of the SUDS connector shown in FIG. 25A.

With reference to FIGS. 25A and B, the fluid injector system 100 may have a sensor system 238 adapted to identify when the SUDS 190 is in fluid communication with the MUDS 130. The sensor system 238 may include at least one sensing element, such as sensor fin 240 on the SUDS 190 and a corresponding sensor 242 on the fluid injector system 100 or MUDS 130. The sensor 242 may be configured to detect the presence and absence of the at least one sensor fin 240, or other sensing element. In some aspects, the sensing element, such as the at least one sensor fin 240 is formed on the locking tab 216 of the SUDS 190, such as shown in FIG. 9A. In other aspects, the sensing element, such as the at least one sensor fin 240 may be formed on any portion of the SUDS 190. The sensor 242 may be an optical sensor that is seated and secured within a respective mount formed on the housing 102 of the fluid injector system 100. As will be appreciated by those versed in the field of powered medical fluid injectors, the sensor 242 may be electronically coupled to an electronic control device used to discretely control operation of the fluid injector system, such as the operation of the one or more piston elements, based, at least in part, on input from the sensor 242. The sensing element, such as the sensor fin 240 may have one or more reflective surfaces that reflect visible or infrared light to be detected by the sensor 242. In other aspects, mechanical interaction between the sensing element and the sensor 242 may be used.

In some aspects, the SUDS 190 may further include reuse prevention features (not shown). For example, the SUDS 190 may include one or more breakable, sensor elements, tabs or structures that fold or break when the SUDS 190 is removed from the MUDS 130. Absence of these features may prevent reinsertion and reuse of the SUDS 190 after removal. In this manner, it can be assured that the SUDS 190 is only used for one fluid delivery procedure.

Having generally described the components of the fluid injector system 100, the MUDS 130, and the SUDS 190, a method of operation of using the SUDS 190 will now be described in detail. In use, a medical technician or user removes the disposable SUDS 190 from its packaging (not shown) and inserts the fluid inlet port 202 into the connection port 192 on the MUDS 130. As described above, the SUDS 190 must be inserted in the correct orientation, such that the fluid inlet port 202 is aligned for connection with the connection port 192, and the waste outlet port 204 is aligned for connection with the waste inlet port 196. The SUDS 190 may be secured to the MUDS 130 by inserting the locking tab 216 into the receiving slot 217 on the MUDS 130. Once the SUDS 190 is securely connected to the MUDS 130, for example as sensed by the sensor 242, the fluid injector system 100 (shown in FIGS. 1A and 1B) draws fluid into one or more of the plurality of syringes 132 of the MUDS 130 and performs an automatic priming operation for removing air from the MUDS 130 and the SUDS 190. During such priming operation, fluid from the MUDS 130 is injected through the connection port 192 and into the tubing 208 of the SUDS 190. The fluid flows through the tubing 208 and through the waste outlet port 204 and into the waste reservoir 156. Once the automatic priming operation is completed, the medical technician disconnects the connector 214 from the waste outlet port 204. The connector 214 may then be connected to the patient through a catheter, vascular access device, needle, or additional fluid path set to facilitate fluid delivery to the patient. Once the fluid delivery is completed, the SUDS 190 is disconnected from the patient and the MUDS 130 by disengaging the locking tab 216 of the SUDS 190 from the receiving slot 217 on the MUDS 130. The medical technician may then dispose of the SUDS 190. In certain aspects, removing the SUDS 190 from the MUDS 130 causes reuse prevention features (not shown) to activate, thereby preventing reinsertion and reuse of the SUDS 190.

Figure 26:
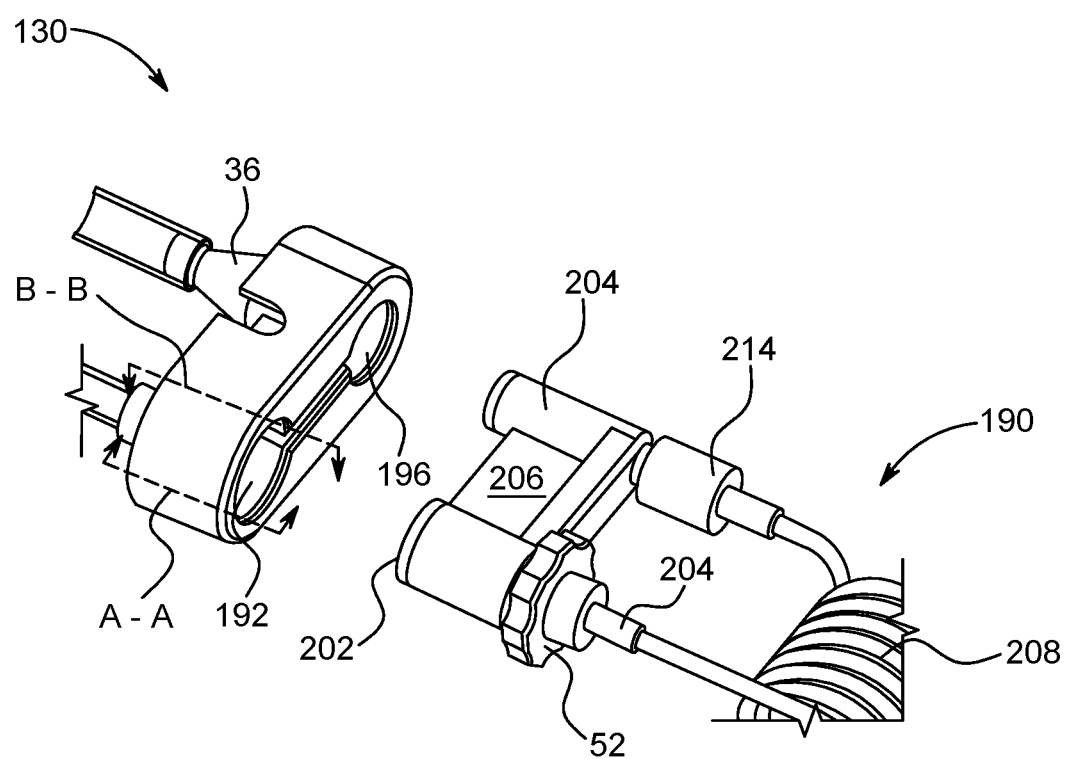
FIG. 26 is a perspective view of a SUDS connector in accordance with another aspect.
Figure 27A:
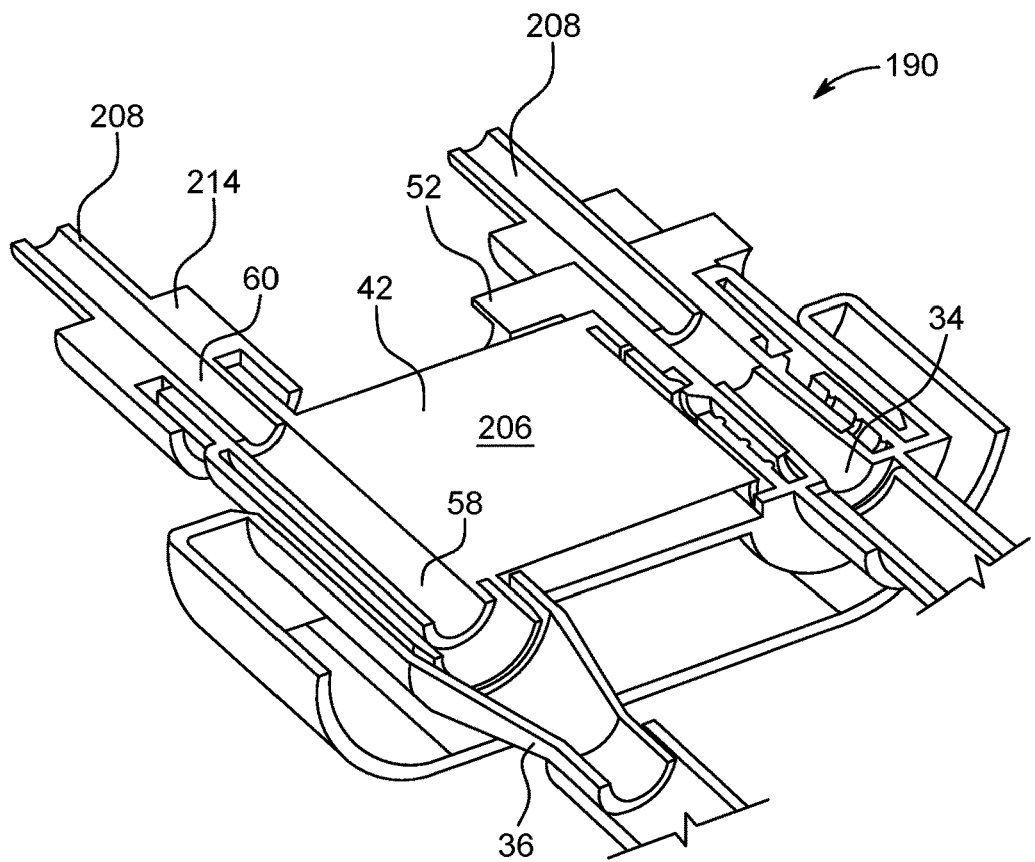
FIG. 27A is an enlarged cross-sectional view of the SUDS connector shown in FIG. 26, taken along line A-A.
Figure 27B:
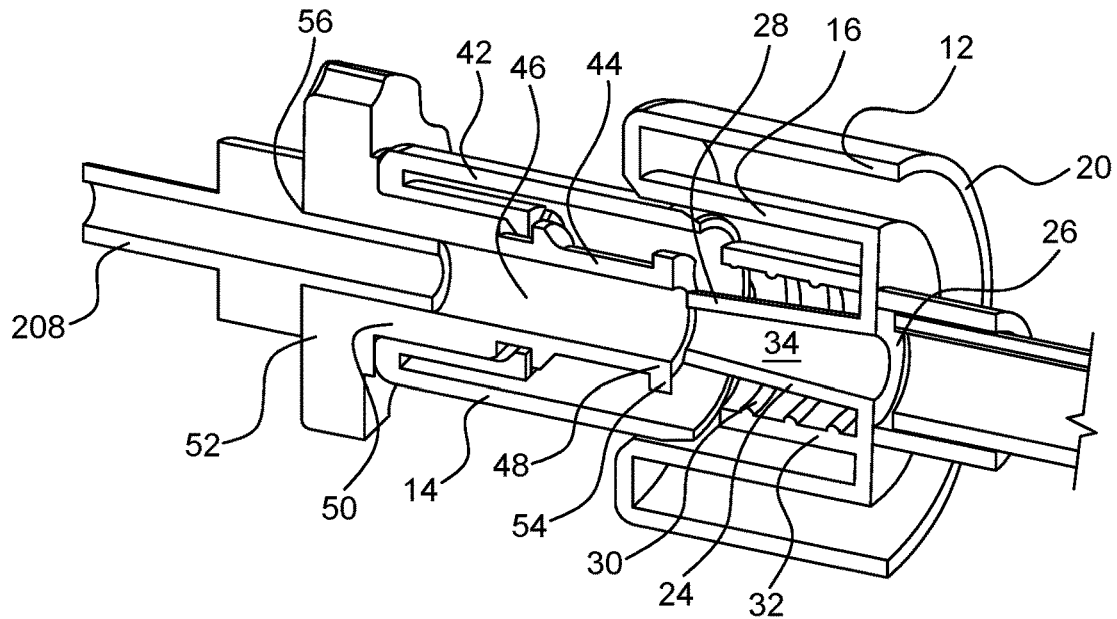
FIG. 27B is an enlarged cross-sectional view of the SUDS connector shown in FIG. 26, taken along line B-B.

With reference to FIG. 26, a connection interface between the SUDS 190 and the MUDS 130 is shown in accordance with another aspect. The MUDS 130 has a connection port 192 that may be configured as a hollow, tubular structure having a luer lock connector 24 (either a male luer lock connector or a female luer lock connector depending on the desired application), extending from a distal end of the port 192 into an interior of the port 192. Accordingly, the proximal opening of the luer lock connector 24 is recessed within the interior of the port 192. The luer lock connector 24 may include screw threads 30 (shown in FIG. 27B) for securing the MUDS 130 to the SUDS 190. For example, the screw threads 30 may be positioned on an outer shroud 32 surrounding the luer lock connector 24, as shown in FIGS. 27A and 27B. Screw threads 30 may also be positioned on the luer lock connector 24 itself. The luer lock connector 24 defines a fluid passageway 34 (shown in FIG. 27B) extending therethrough, from the proximal end of the connection port 192 to the distal opening thereof. While the connection port 192 is depicted as including a luer lock connector 24, other styles of connectors, including, but not limited to, clip-in connectors, bayonet connectors, press fit connectors, and the like, may be used within the scope of the present disclosure. Additionally, in certain aspects, the connector 24 for the connection port 192 is desirably a non-standard connector (e.g. a connector with an unusual size or shape) so that connectors produced by third parties cannot be attached.

The MUDS 130 has a waste inlet port 196 (shown in FIG. 26) that may also be configured as a hollow, tubular structure. The waste inlet port 196 includes a tapered distal nozzle 36 attached to a fluid conduit, such as flexible tubing that connects the waste inlet port 196 to the waste reservoir 156 (shown in FIG. 2).

With reference again to FIG. 26, as described in detail herein, the MUDS 130 is adapted for connecting to the SUDS 190, which is disposed of after a single use. It is noted that the SUDS 190 is shown in FIG. 26 in a state after removal from packaging (not shown). Prior to use, the SUDS 190 is desirably packaged in a pre-sterilized, sealed package that protects the SUDS 190 from contamination with air or surface-borne contaminants.

The SUDS 190 may have two or more ports, corresponding to the connection port 192 and waste inlet port 196 of the MUDS 130. For convenience, the ports of the SUDS 190 are equivalent to the fluid inlet port 202 and the waste outlet port 204 of the SUDS 190 described with reference to FIGS. 9A-9B. The ports 202, 204 may be provided in an enclosure 42 suitable for receipt within the housing 20 of the MUDS 130, as shown in FIG. 27B. The enclosure 42 desirably has an asymmetrical structure, so that the user can only attach the SUDS 190 to the MUDS 130 in one orientation only. Thus, for example, the user is prevented from attaching the connection port 192 of the MUDS 130 to the SUDS 190 waste outlet port 204. The ports 202, 204 and enclosure 42 of the SUDS 190 may be made from a material suitable for medical applications, such as medical grade plastic. The tubing 208 of the SUDS 190 is connected between the proximal end of the fluid inlet port 202 and the end of the waste outlet port 204 through check valves. The tubing 208 may be provided in a wound or coiled configuration for easy packaging and maneuverability.

With reference to FIGS. 27A and 27B, the SUDS 190 fluid inlet port 202 is a hollow, tubular structure configured for insertion in the connection port 192 of the MUDS 130. The SUDS 190 fluid inlet port 202 includes a tubular conduit, such as a luer lock connector 44, defining a fluid passageway 46 extending from a proximal end of the port 202, located adjacent to the MUDS 130, and the distal end of the port 204, connected to the tubing 208. The luer lock connector 44 is adapted to connect to the luer lock connector 24 of the MUDS 130. When securely connected, the connection port 192 of the MUDS 130 is in fluid communication with the fluid inlet port 202 of the SUDS 190. The luer lock connector 44 may include a thumbwheel 52 for securing the connection port 192 of the MUDS 130 to the SUDS 190 fluid inlet port 202. The thumbwheel 52 may be integrally formed with the luer lock connector 44 or may be a separate structure fixedly connected to the luer lock connector 44 by conventional means. The thumbwheel 52 rotates the luer lock connector 44 causing tabs 54, extending therefrom, to engage the corresponding screw threads 30 in the connection port 192. The tubing 208 is connected to the fluid inlet port 202 through an opening 56 on the thumbwheel 52, such that a continuous fluid connection is established from the MUDS 130 to the tubing 208.

With continued reference to FIGS. 27A and 27B, the SUDS 190 also includes the SUDS 190 waste outlet port 204. The SUDS waste outlet port 204 has a fluid passageway 58, defined by a tubular conduit 60, extending between the waste inlet port 196 of the MUDS 130, and the tubing 208. The tubing 208 may not be directly connected to the waste inlet port 196 of the MUDS 130. Instead, the tubular conduit 60 of the SUDS 190 may separate the tubing 208 from the MUDS 130, thereby ensuring that the tubing 208 and the connector 214 are isolated from the waste inlet port 196 of the MUDS 130. The tubular conduit 60 may be recessed from the waste inlet port 196 of the MUDS 130 by a portion of the single-use connector enclosure 42, to reduce the likelihood of contamination. The tubular conduit 60 may also be angled, relative to the horizontal, to facilitate fluid flow through the SUDS 190 waste outlet port 204 and into the waste inlet port 196 of the MUDS 130. In some aspects, the SUDS 190 may further include reuse prevention features (not shown). For example, the SUDS 190 may include breakable tabs or structures that fold or break when the SUDS 190 is removed from the MUDS 130. In this manner, it can be assured that the SUDS 190 is only used for one fluid delivery procedure.

Figure 28A:
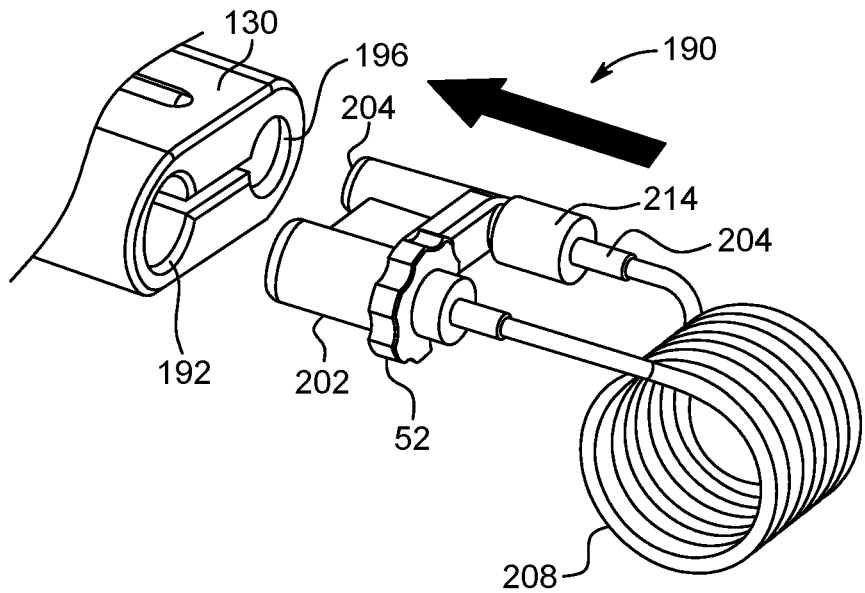
FIGS. 28A-28F are perspective views of various stages of connecting a SUDS connector to a MUDS connector.
Figure 28B:
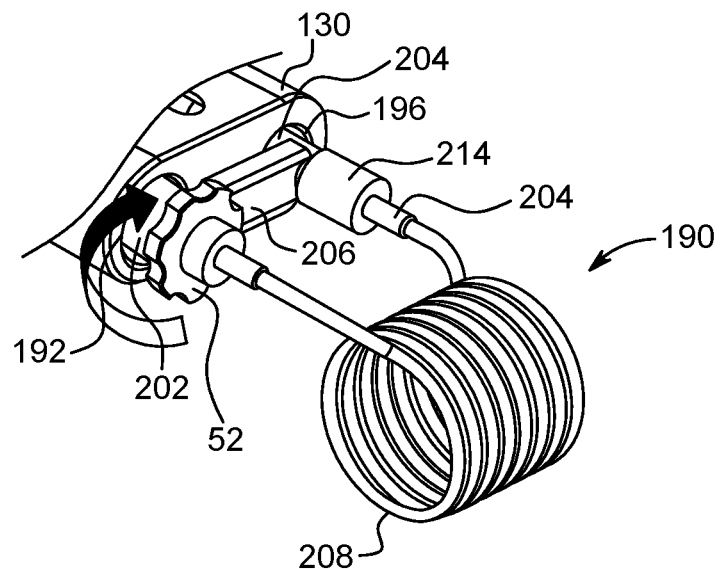
Figure 28C:
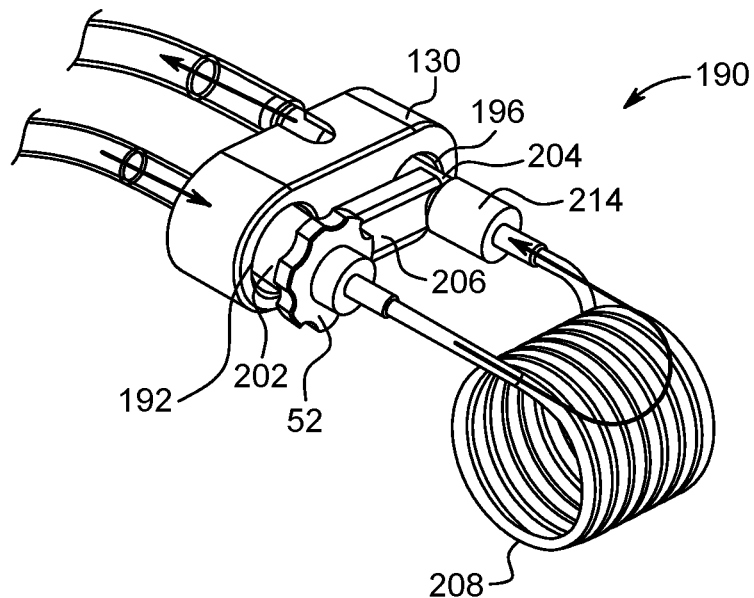
Figure 28D:
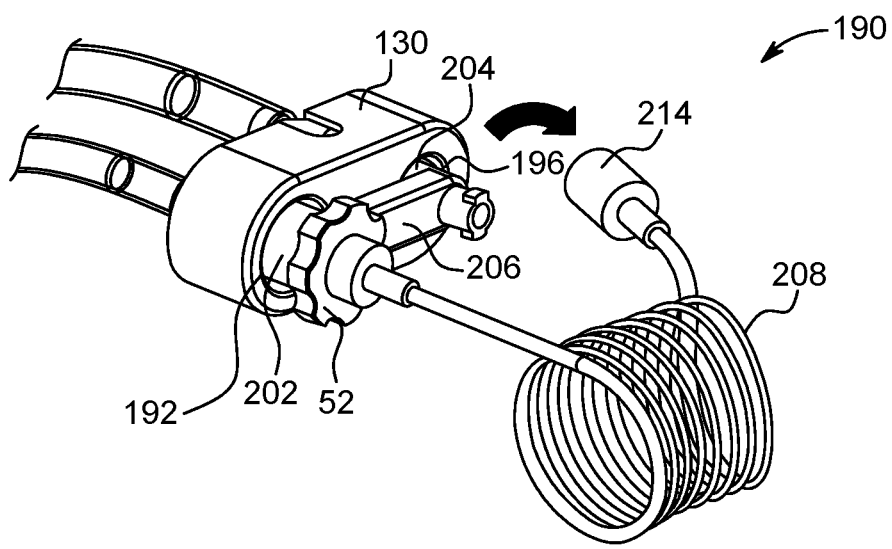
Figure 28E:
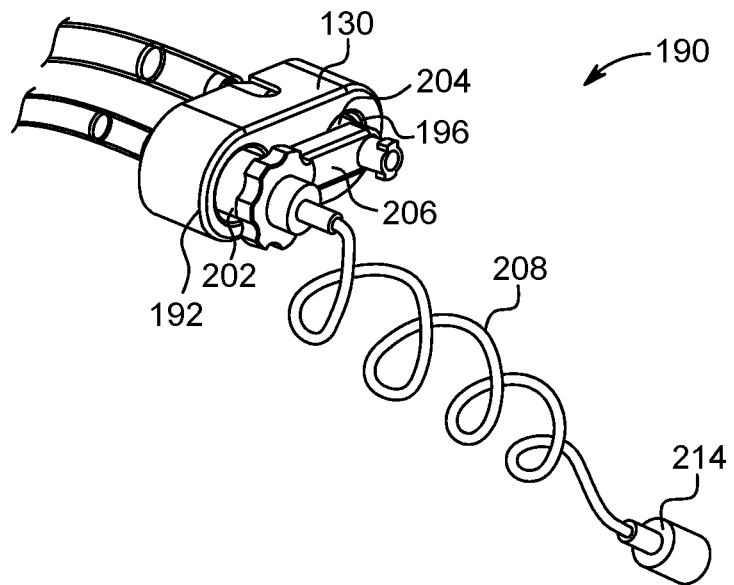
Figure 28F:
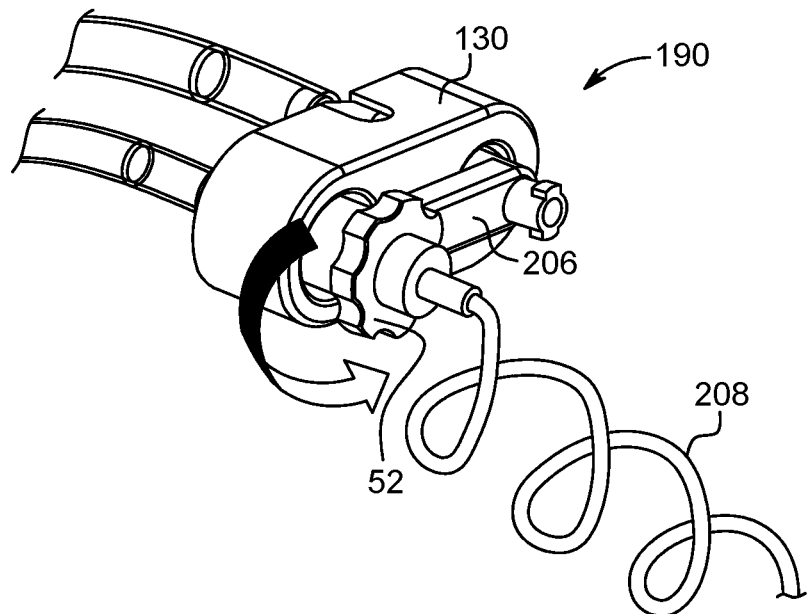

With reference to FIGS. 28A-28F, a method of operation of the aspect of the connection assembly between the SUDS 190 and MUDS 130 depicted in FIGS. 26-27B will now be described in detail. In use, a medical technician or user removes the disposable SUDS 190 from its packaging and inserts the SUDS 190 into the corresponding MUDS 130. As described above, the SUDS 190 must be inserted in the correct orientation, such that the connection port 192 of the MUDS 130 engages the SUDS 190 fluid inlet port 202, and the waste inlet port 196 of the MUDS 130 engages the SUDS 190 waste outlet port 204. As shown in FIG. 28B, the medical technician then rotates the thumbwheel 52 to secure the SUDS 190 to the MUDS 130. Once the SUDS 190 is securely connected to the MUDS 130, the fluid injector system 100 (shown in FIGS. 1A and 1B) draws fluid into one or more of the plurality of syringes 132 of the MUDS 130 and performs an automatic priming operation (FIG. 28C) for removing air from the MUDS 130 and the SUDS 190. During such priming operation, fluid from the MUDS 130 is injected through the connection port 192 and into the tubing 208 of the SUDS 190. The fluid flows through the tubing 208 and through the waste outlet port 204 and into the waste reservoir 156. Once the automatic priming operation is completed, the medical technician disconnects the connector 214 from the waste outlet port 204 (FIG. 28D). The connector 214 may then be connected to the patient through a catheter, vascular access device, or additional fluid path set to facilitate fluid delivery to the patient (FIG. 28E). Once the fluid delivery is completed, the user the connector 214 from the patient and rotates the thumbwheel 52 to remove the SUDS 190 from the MUDS 130 (FIG. 28F). The medical technician may then dispose of the SUDS 190. In certain aspects, removing the SUDS 190 from the MUDS 130 causes reuse prevention features (not shown), such as tabs extending from a portion of the SUDS 190, to fold or break, preventing reinsertion of the SUDS 190.

Figure 29:
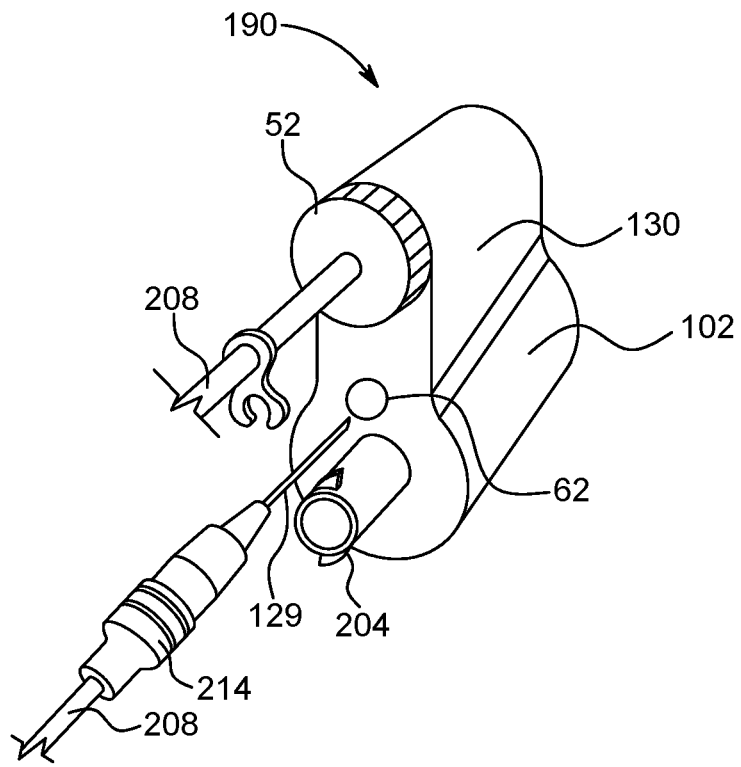
FIG. 29 is a perspective view of a SUDS connector in accordance with another aspect.

With reference to FIG. 29, a further aspect of a connector assembly having a SUDS 190 and a MUDS 130 is illustrated. In this aspect of the assembly, the SUDS 190 includes a cannula port 62 for receiving a needle cannula 129 connected to a connector 214. The cannula 129, used for fluid delivery to a patient, can be inserted into the cannula port 62 after being removed from the patient. The cannula port 62 may cover a contaminated end of the cannula 129 during disposal of the cannula 129. In this aspect, the single-use enclosure 42 is desirably long enough so that the entire length of the needle cannula 129 may be inserted in the enclosure 42 for a safe disposal.

Figure 30A:
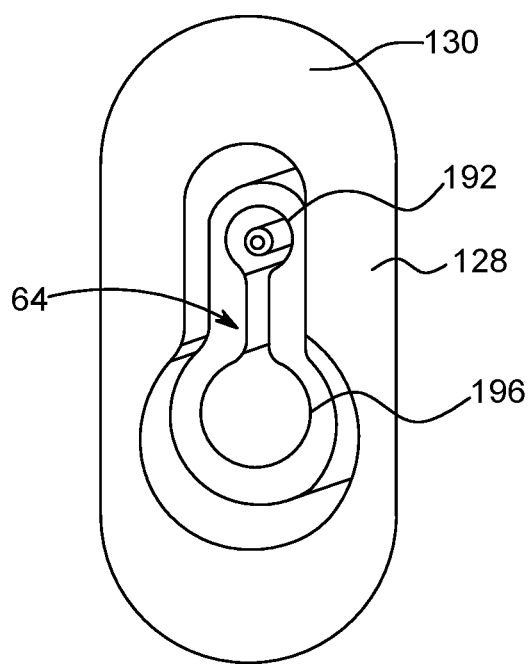
FIG. 30A is a perspective view of a port of a MUDS connector in accordance with one aspect.
Figure 30B:
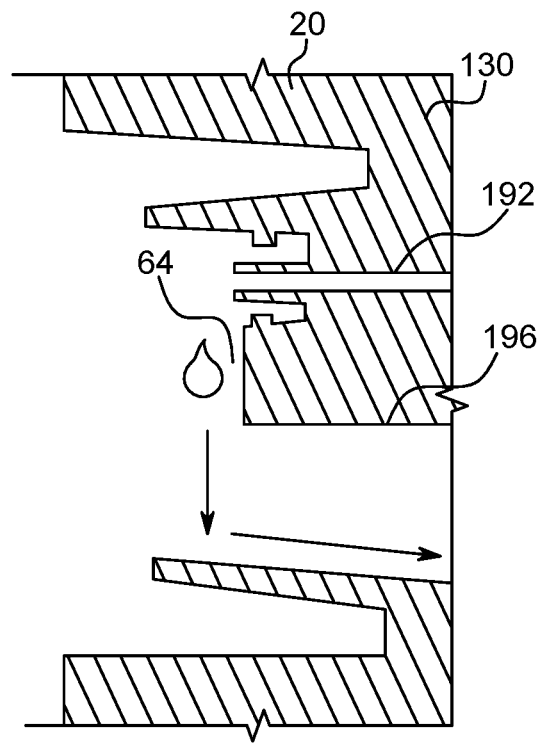
FIG. 30B is a schematic drawing of a cross-sectional view of the MUDS connector of FIG. 30A.
Figure 30C:
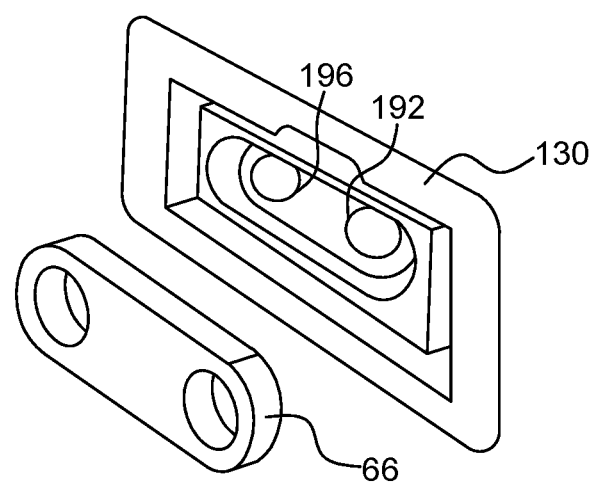
FIG. 30C is a schematic drawing of a MUDS connector having an absorbent pad attached thereto, according to another aspect.

With reference to FIGS. 30A and 30B, a further aspect of a connector assembly having a SUDS 190 and a MUDS 130 is illustrated. The connector assembly is provided in a vertical orientation with the connection port 192 of the MUDS 130 positioned above the waste inlet port 196. The MUDS 130 includes a drip channel 64 extending between the connection port 192 and waste inlet port 196. Any fluid leaking from the connection port 192 is directed downward through the drip channel 64 by gravity. The drip channel 64 exits into the waste inlet port 196. Accordingly, any fluid expelled from the drip channel 64 is directed through the waste inlet port 196 and is collected in the waste reservoir 156. Alternatively, the MUDS 130 may be provided with an absorbent material, such as an absorbent pad 66 shown in FIG. 30C, surrounding a portion of the connection port 192 and the waste inlet port 196. The absorbent material is provided to absorb any fluid drips during removal of the SUDS 190 for improved drip management.

Figure 31A:
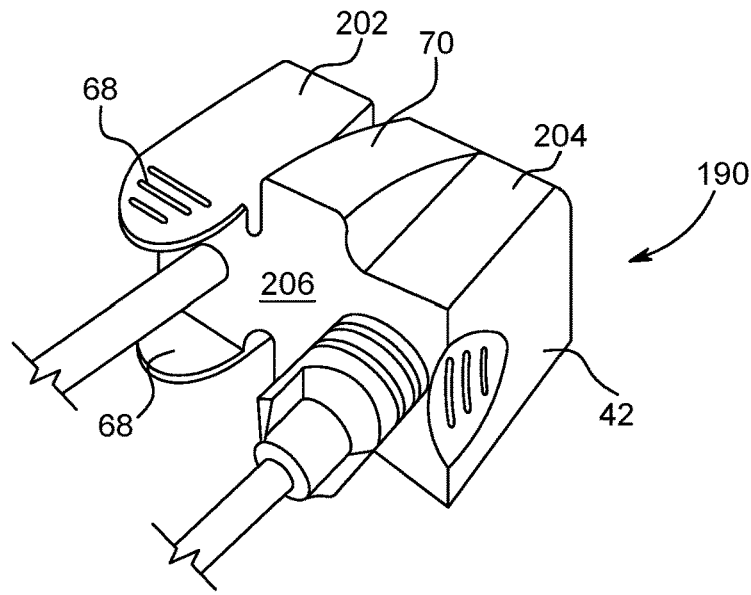
FIG. 31A is a perspective view of a SUDS connector in accordance with another aspect.
Figure 31B:
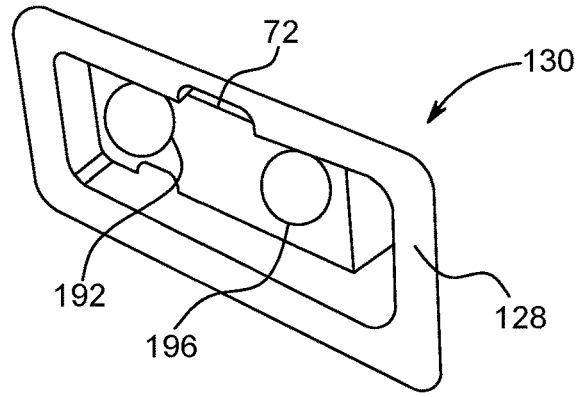
FIG. 31B is a perspective view of a MUDS connector in accordance with another aspect.
Figure 31C:
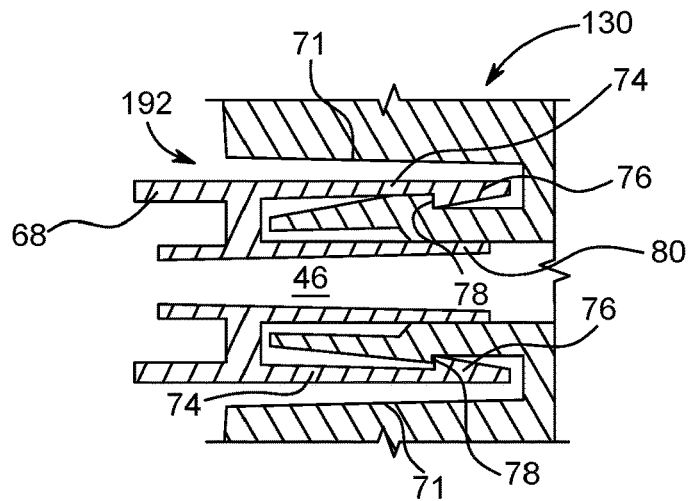
FIG. 31C is a cross-sectional view of a medical connector assembly, with the SUDS connector of FIG. 31A inserted to the MUDS connector of FIG. 31B.

With reference to FIGS. 31A-31C, a further aspect of the connector assembly having a SUDS 190 and a MUDS 130 having a plurality of press-fit connectors is illustrated. As shown in FIG. 31A, the SUDS 190 includes a fluid inlet port 202 and waste outlet port 204. The SUDS 190 includes disconnection tabs 68, rather than a thumbwheel. The SUDS 190 also includes an alignment structure 70 extending from the enclosure 42 of the SUDS 190 and is configured for insertion in a corresponding slot 72 of the MUDS 130 (shown in FIG. 31B).

Figure 32:
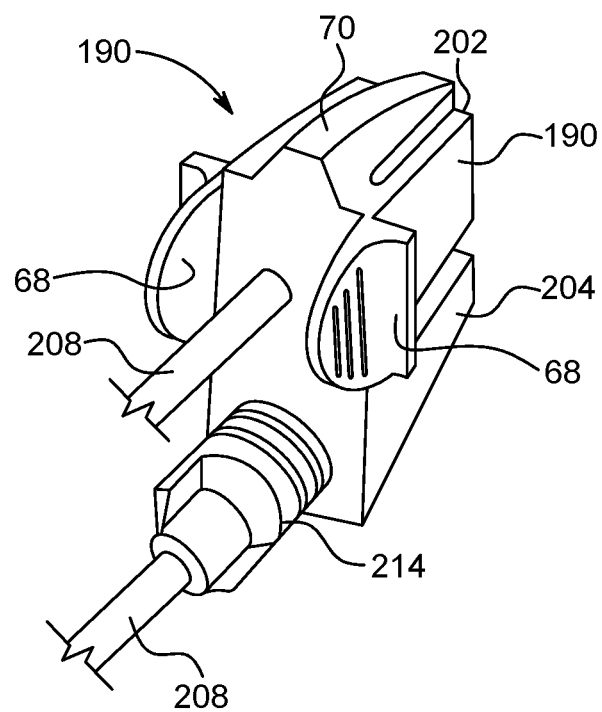
FIG. 32 is a front perspective view of a SUDS connector in accordance with another aspect.

As shown in the cross-sectional view depicted in FIG. 31C, the SUDS 190 is inserted into and aligned with the MUDS 130 by alignment channels 71. The disconnection tabs 68 are integrally formed with a tubular shroud 74 having an inwardly extending flange 76 at one end thereof. The shroud 74 surrounds a tubular conduit 80 on the SUDS 190. When the SUDS 190 is inserted into the MUDS 130, the flange 76 forms an interference engagement with a corresponding ridge 78 extending from a portion of the connection port 192 of the MUDS 130. The interference engagement creates a substantially fluid-tight connection between the MUDS 130 and the SUDS 190. Pressing the disconnection tabs 68 of the SUDS 190 disengages the flange 76 from the ridge 78 to allow a user to remove the SUDS 190 from the MUDS 130. With reference to FIG. 32, the connection assembly, having a MUDS 130 and SUDS 190 with disconnection tabs 68 described above, may also be provided in a vertical configuration.

Figure 33A:
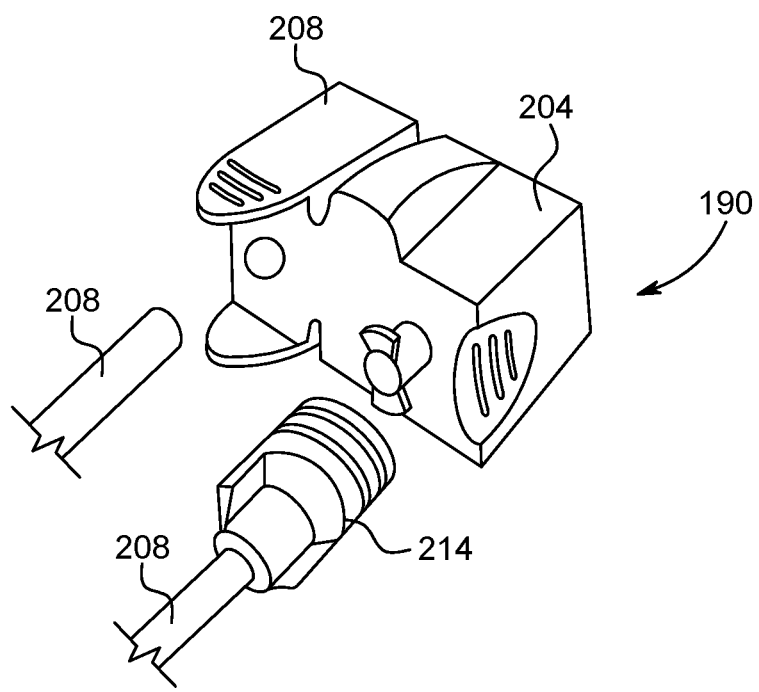
FIG. 33A is a perspective view of a SUDS connector in accordance with another aspect.
Figure 33B:
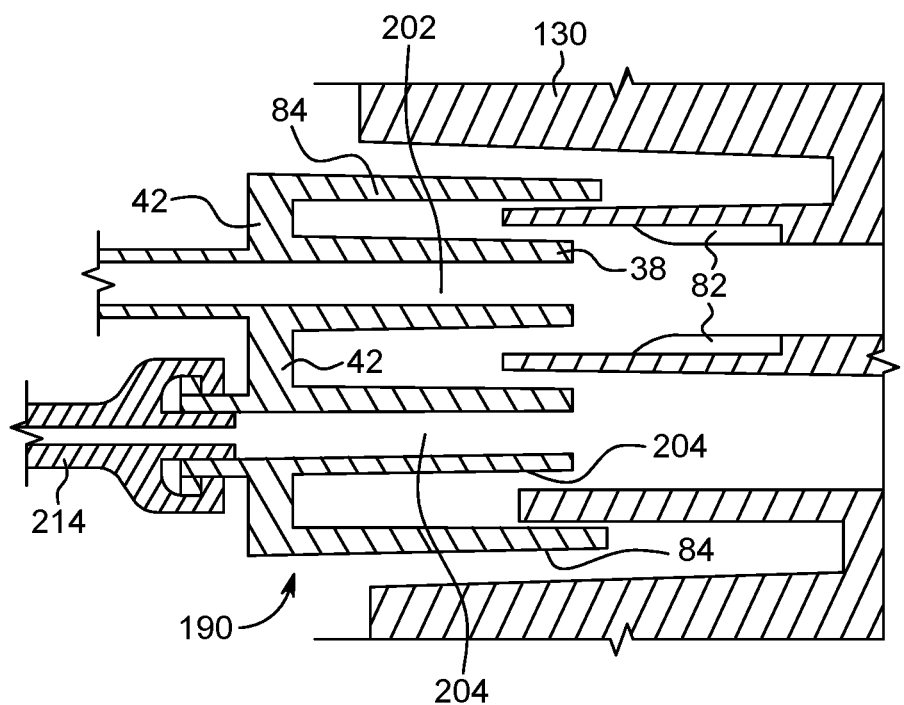
FIG. 33B is a cross-sectional view of a medical connection assembly including the SUDS connector of FIG. 33A.
Figure 34A:
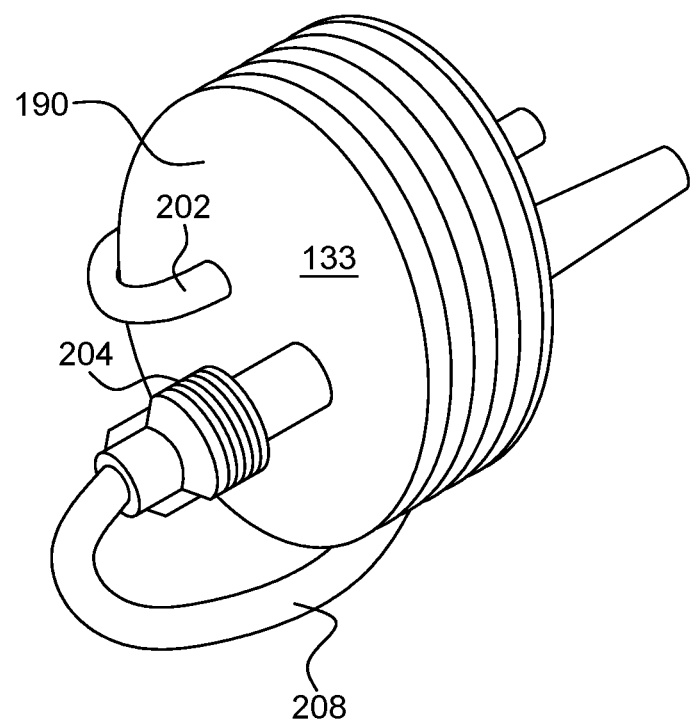
FIG. 34A is a perspective view of a SUDS connector in accordance with another aspect.
Figure 34B:
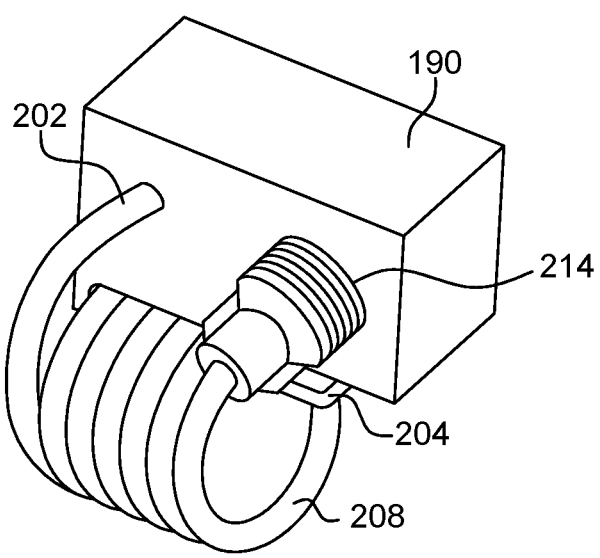
FIG. 34B is a perspective view of a SUDS connector in accordance with another aspect.
Figure 35A:
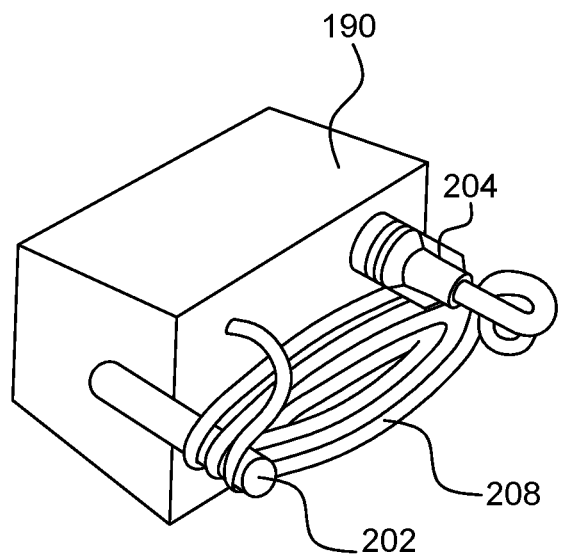
FIG. 35A is a perspective view of a SUDS connector in accordance with another aspect.
Figure 35B:
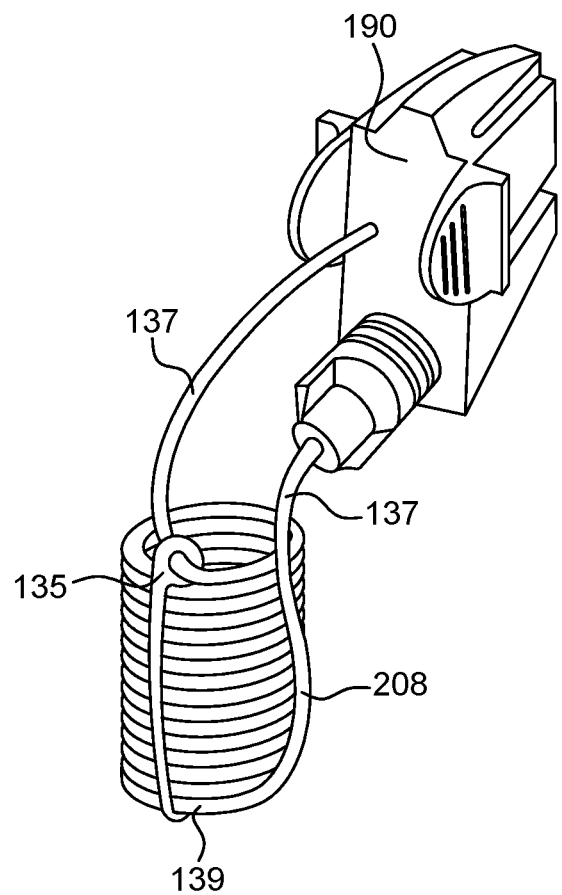
FIG. 35B is a perspective view of a SUDS connector in accordance with another aspect.
Figure 36A:
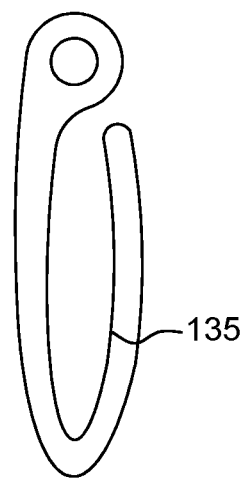
FIG. 36A is a side view of an external clip of the SUDS connector of FIG. 35A.
Figure 36B:
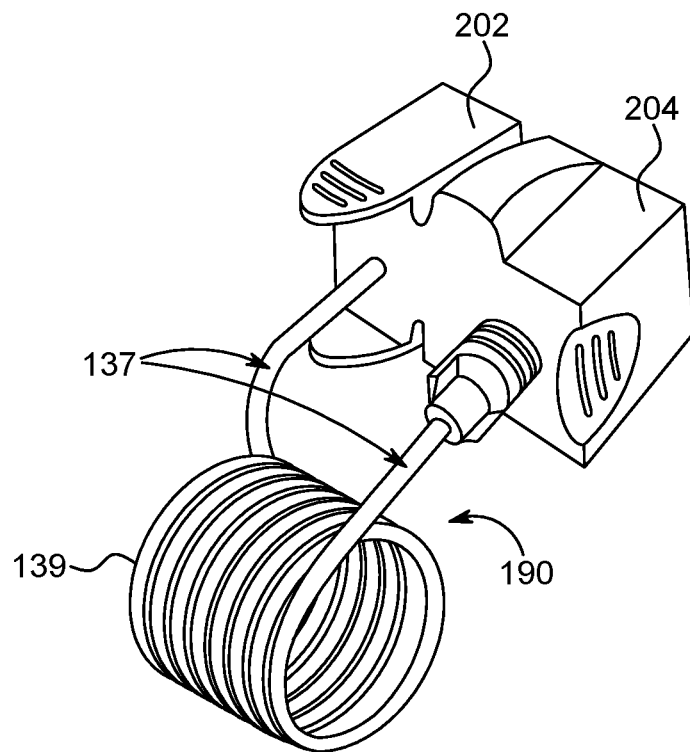
FIG. 36B is a perspective view of a SUDS of a medical connector assembly, according to another aspect.

With reference to FIGS. 33A and 33B, a further aspect of the connector assembly having a SUDS 190 and a MUDS 130 is illustrated. The MUDS 130 includes the connection port 192 and waste inlet port 196, as described in previous aspects. The connection port 192 includes a co-molded sealing surface 82 for enhancing the connection between the SUDS 190 and the MUDS 130. The SUDS 190 includes external alignment surfaces 84, integrally formed with the enclosure 42, for correctly aligning the SUDS 190 and the MUDS 130. The alignment surfaces 84 also recess the fluid inlet port 202 and the waste outlet port 204 of the SUDS 190 to reduce the possibility of contamination prior to use.

With reference to FIGS. 34A-36B, various aspects of the tubing 208 are illustrated. For example, the tubing 208 may be wound about a holding structure 133, such as a spool or frame member, for ensuring that the tubing 208 does not unwind while being removed from its packaging or when the SUDS 190 is being connected to the MUDS 130. With reference to FIG. 36A, the tubing 208 may further include a removable external clip 135. The clip 135 connects about the wound tubing 208 to prevent the tubing 208 from unwinding during removal from packaging or auto-priming With reference to FIG. 36B, in a further aspect, the tubing 208 is provided with uncoiled portions 137 to keep the tubing 208 away from the SUDS 190. A coiled portion 139 of the tubing 208 hangs below the un-coiled portions 137, when the SUDS 190 is connected to the MUDS 130.

Figure 37:
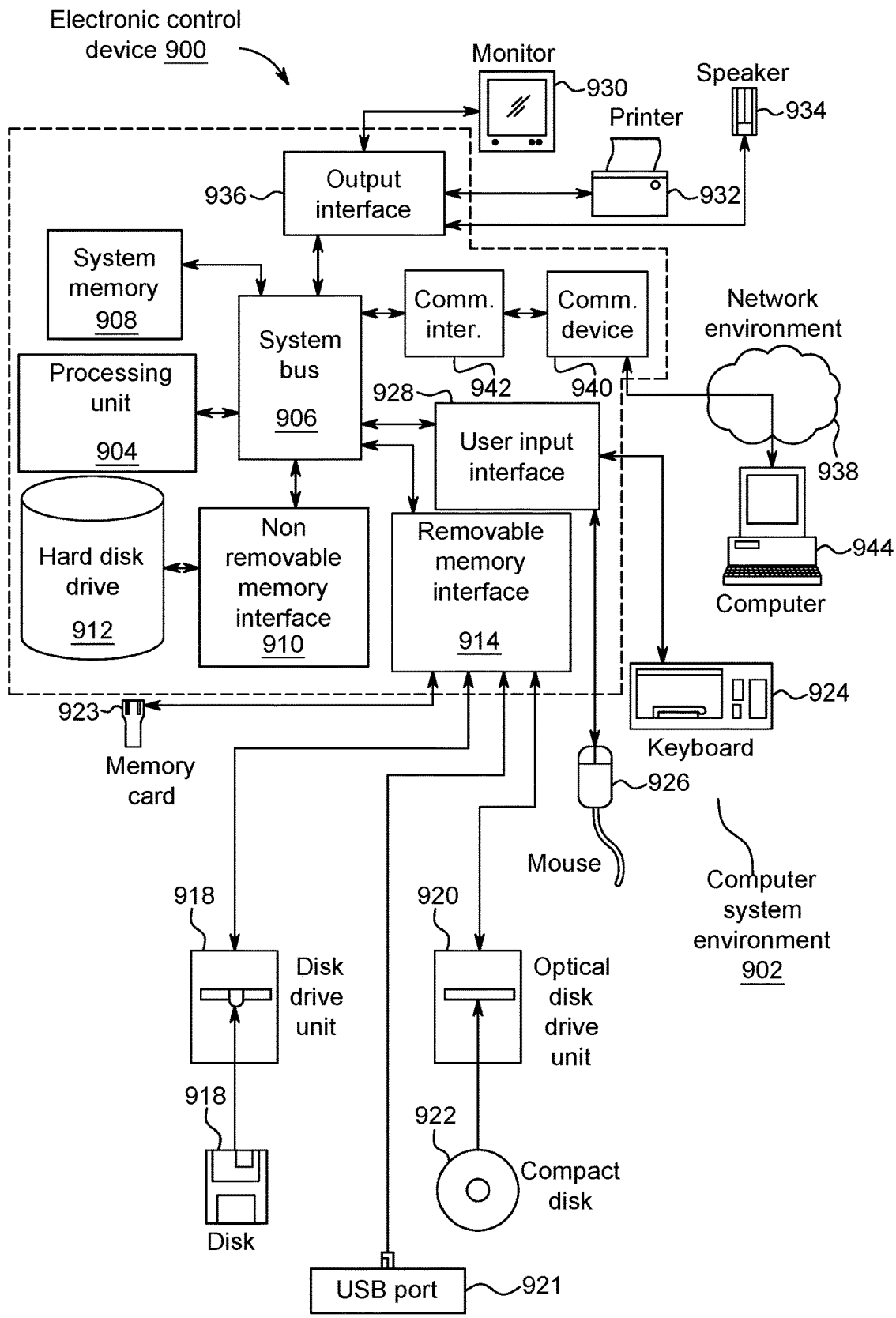
FIG. 37 is a schematic view of an electronic control system of a multi-fluid fluid injection system in accordance with another aspect.

With reference to FIG. 37, an electronic control device 900 may be associated with fluid injector system 100 to control the filling and delivery operations. In some aspects, the electronic control device 900 may control the operation of various valves, piston members, and other elements to effect a desired filling or delivery procedure. For example, the electronic control device 900 may include a variety of discrete computer-readable media components. For example, this computer-readable media may include any media that can be accessed by the electronic control device 900, such as volatile media, non-volatile media, removable media, non-removable media, transitory media, non-transitory media, etc. As a further example, this computer-readable media may include computer storage media, such as media implemented in any method or technology for storage of information, such as computer-readable instructions, data structures, program modules, or other data; random access memory (RAM), read only memory (ROM), electrically erasable programmable read only memory (EEPROM), flash memory, or other memory technology; CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic control device 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic control device 900 further includes a system memory 908 with computer storage media in the form of volatile and non-volatile memory, such as ROM and RAM. A basic input/output system (BIOS) with appropriate computer-based routines assists in transferring information between components within the electronic control device 900 and is normally stored in ROM. The RAM portion of the system memory 908 typically contains data and program modules that are immediately accessible to or presently being operated on by the processing unit 904, e.g., an operating system, application programming interfaces, application programs, program modules, program data, and other instruction-based computer-readable codes.

With continued reference to FIG. 37, the electronic control device 900 may also include other removable or non-removable, volatile or non-volatile, transitory or non-transitory computer storage media products. For example, the electronic control device 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in the exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the electronic control device 900 via the system bus 906. The drives and their associated computer storage media, discussed above and illustrated in FIG. 37, provide storage of operating systems, computer-readable instructions, application programs, data structures, program modules, program data, and other instruction-based, computer-readable code for the electronic control device 900 (whether duplicative or not of this information and data in the system memory 908).

A user may enter commands, information, and data into the electronic control device 900 through certain attachable or operable input devices, such as the user interface 124 shown in FIG. 1A, via a user input interface 928. Of course, a variety of such input devices may be utilized, e.g., a microphone, a trackball, a joystick, a touchpad, a touchscreen, a scanner, etc., including any arrangement that facilitates the input of data, and information to the electronic control device 900 from an outside source. As discussed, these and other input devices are often connected to the processing unit 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic control device 900 through an output interface 936 coupled to the system bus 906. It is envisioned that any such peripheral output devices be used to provide information and data to the user.

The electronic control device 900 may operate in a network environment 938 through the use of a communications device 940, which is integral to the electronic control device 900 or remote therefrom. This communications device 940 is operable by and in communication with the other components of the electronic control device 900 through a communications interface 942. Using such an arrangement, the electronic control device 900 may connect with or otherwise communicate with one or more remote computers, such as a remote computer 944, which may be a personal computer, a server, a router, a network personal computer, a peer device, or other common network nodes, and typically includes many or all of the components described above in connection with the electronic control device 900. Using appropriate communication devices 940, e.g., a modem, a network interface or adapter, etc., the computer 944 may operate within and communicate through a local area network (LAN) and a wide area network (WAN), but may also include other networks such as a virtual private network (VPN), an office network, an enterprise network, an intranet, the Internet, etc.

As used herein, the electronic control device 900 includes, or is operable to execute appropriate custom-designed or conventional software to perform and implement the processing steps of the method and system of the present disclosure, thereby forming a specialized and particular computing system. Accordingly, the presently-disclosed method and system may include one or more electronic control devices 900 or similar computing devices having a computer-readable storage medium capable of storing computer-readable program code or instructions that cause the processing unit 904 to execute, configure, or otherwise implement the methods, processes, and transformational data manipulations discussed hereinafter in connection with the present disclosure. Still further, the electronic control device 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-disclosed computer-implemented method and system.

It will be apparent to one skilled in the relevant arts that the system may utilize databases physically located on one or more computers which may or may not be the same as their respective servers. For example, programming software on electronic control device 900 can control a database physically stored on a separate processor of the network or otherwise.

In some aspects, the electronic control device 900 may be programmed so that automatic refill occurs based upon a preprogrammed trigger minimum volume in the respective syringes 132. For example, when the volume of fluid remaining in at least one of the syringes 132 is less than a programmed volume, a syringe refill procedure is automatically initiated by the electronic control device 900. The electronic control device 900 associated with the fluid injector system 100 may determine that the preprogrammed trigger minimum volume has been reached by tracking the fluid volume dispensed from the respective syringes 132 during operation of the fluid injector system 100. Alternatively, fluid level sensors may be incorporated into the fluid injector system 100 and inputs from these fluid level sensors may be provided to the electronic control device 900 so that the electronic control device 900 may determine when the preprogrammed trigger minimum volume has been reached in at least one of the syringes 132. The fill volume and rate of refill can be preprogrammed in the electronic control device 900. The automatic refill procedure can be stopped either automatically by the electronic control device 900 or may be manually interrupted. In addition, an automatic refill procedure may be initiated when, at the completion of a fluid injection procedure, there is not enough fluid in at least one of the syringes 132 to perform the next programmed fluid injection procedure.

During a refill procedure it is possible that one or more of the bulk fluid sources 120 associated with the respective syringes 132 may become empty, (e.g., initially lack sufficient fluid to complete a full refill of the one or more syringes 132). A replacement bulk fluid source 120 is, therefore, necessary and replacement of such bulk fluid source 120 is desirably made quickly. The fluid injector system 100 may have an indicator, such as an audible and/or visual indicator, to indicate to the operator that a change of the bulk fluid source 120 is necessary before the fluid injector system 100 may be used.

While several aspects of multi-fluid delivery systems and multi- and SUDS connectors therefor are shown in the accompanying figures and described hereinabove in detail, other aspects will be apparent to, and readily made by, those skilled in the art without departing from the scope and spirit of the disclosure. For example, it is to be understood that this disclosure contemplates that, to the extent possible, one or more features of any aspect can be combined with one or more features of any other aspect. Accordingly, the foregoing description is intended to be illustrative rather than restrictive.

We claim:

1. A multi-fluid injector system, comprising:
   a powered injector comprising a housing enclosing a plurality of reciprocally operable piston elements;
   a receiving space configured for removably receiving a plurality of syringes of a multi-use disposable set (MUDS), the receiving space comprising a bottom plate and a top plate spaced apart from the bottom plate by a rear sidewall such that the plurality of syringes of the MUDS are supported axially between the top plate and the bottom plate; and
   at least one guide associated with the receiving space,
   wherein the at least one guide narrows in an insertion direction toward the rear sidewall to guide the MUDS into the receiving space, and
   wherein the top plate defines a plurality of slots configured for receiving at least one of the plurality of syringes of the MUDS, and wherein each of the plurality of slots defines a mating recess for receiving a conical distal end of the at least one syringe such that the conical distal end engages the mating recess when the MUDS is received in the receiving space.

2. The multi-fluid injector system of claim 1, wherein the MUDS is configured for connecting with a plurality of bulk fluid sources.

3. The multi-fluid injector system of claim 1, wherein the top plate is movable between a first position configured for insertion and removal of the MUDS within the receiving space and a second position configured for locking the MUDS within the receiving space.

4. The multi-fluid injector system of claim 3, wherein the top plate comprises at least one latch for locking the top plate in the second position.

5. The multi-fluid injector system of claim 1, further comprising at least one coupling configured for engaging at least one valve on the MUDS.

6. The multi-fluid injector system of claim 5, wherein the at least one coupling is a rotatable coupling having a blade configured for self-alignment with a slot formed on the at least one valve on the MUDS.

* * * * *

UNITED STATES PATENT AND TRADEMARK OFFICE
CERTIFICATE OF CORRECTION

| | |
|---|---|
| PATENT NO. | : 11,491,318 B2 |
| APPLICATION NO. | : 16/713299 |
| DATED | : November 8, 2022 |
| INVENTOR(S) | : Haury et al. |

It is certified that error appears in the above-identified patent and that said Letters Patent is hereby corrected as shown below:

On the Title Page

Item (72), under "Inventors", in Column 1, Line 1, delete "Sewickly," and insert -- Sewickley, --, therefor.

In the Specification

In Column 1, Line 10, delete "2017," and insert -- 2017, now U.S. Pat. No. 10,507,319, --, therefor.

In Column 26, Line 13, delete "valve assembly 272" and insert -- valve assembly 136 --, therefor.

Signed and Sealed this
Twentieth Day of June, 2023

Katherine Kelly Vidal
*Director of the United States Patent and Trademark Office*